US008192741B2

(12) United States Patent
Radin et al.

(10) Patent No.: US 8,192,741 B2
(45) Date of Patent: *Jun. 5, 2012

(54) METHOD OF TREATING RHEUMATOID ARTHRITIS WITH AN ANTI-IL-6R ANTIBODY

(75) Inventors: Allen Radin, New York, NY (US); Sean Stevens, San Francisco, CA (US); Tammy T. Huang, Goldens Bridge, NY (US); Joel H. Martin, Putnam Valley, NY (US); Jeanette L. Fairhurst, White Plains, NY (US); Ashique Rafique, Yonkers, NY (US); Eric Smith, New York, NY (US); Kevin J. Pobursky, Beacon, NY (US); Nicholas J. Papadopoulos, LaGrangeville, NY (US); James P. Fandl, LaGrangeville, NY (US); Gang Chen, Yorktown Heights, NY (US); Margaret Karow, Santa Rosa Valley, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/286,261

(22) Filed: Nov. 1, 2011

(65) Prior Publication Data

US 2012/0045440 A1 Feb. 23, 2012

Related U.S. Application Data

(60) Division of application No. 12/780,006, filed on May 14, 2010, now Pat. No. 8,080,248, which is a continuation-in-part of application No. 12/501,657, filed on Jul. 13, 2009, now Pat. No. 8,043,617, which is a division of application No. 11/809,482, filed on Jun. 1, 2007, now Pat. No. 7,582,298.

(60) Provisional application No. 60/810,664, filed on Jun. 2, 2006, provisional application No. 60/843,232, filed on Sep. 8, 2006, provisional application No. 61/181,749, filed on May 28, 2009, provisional application No. 61/262,661, filed on Nov. 19, 2009, provisional application No. 61/297,302, filed on Jan. 22, 2010.

(51) Int. Cl.
*A61K 39/395* (2006.01)

(52) U.S. Cl. ............... 424/143.1; 424/130.1; 424/141.1; 424/142.1; 424/144.1; 514/885

(58) Field of Classification Search ........................ None
See application file for complete search history.

(56) References Cited

U.S. PATENT DOCUMENTS

| | | |
|---|---|---|
| 5,480,796 A | 1/1996 | Kishimoto |
| 5,670,373 A | 9/1997 | Kishimoto |
| 5,723,120 A | 3/1998 | Brakenhoff et al. |
| 5,795,965 A | 8/1998 | Tsuchiya et al. |
| 5,817,790 A | 10/1998 | Tsuchiya et al. |
| 5,888,510 A | 3/1999 | Kishimoto et al. |
| 5,888,511 A | 3/1999 | Skurkovich et al. |
| 6,086,874 A | 7/2000 | Yoshida et al. |
| 6,261,560 B1 | 7/2001 | Tsujinaka et al. |
| 6,410,691 B1 | 6/2002 | Kishimoto |
| 6,692,742 B1 | 2/2004 | Nakamura et al. |
| 6,723,319 B1 | 4/2004 | Ito et al. |
| 7,320,792 B2 | 1/2008 | Ito et al. |
| 7,479,543 B2 | 1/2009 | Tsuchiya et al. |
| 7,582,298 B2 | 9/2009 | Stevens et al. |
| 2002/0187150 A1 | 12/2002 | Mihara et al. |
| 2004/0071706 A1 | 4/2004 | Ito et al. |
| 2004/0115197 A1 | 6/2004 | Yoshizaki et al. |
| 2004/0219156 A1 | 11/2004 | Goldenberg et al. |
| 2005/0142635 A1 | 6/2005 | Tsuchiya et al. |
| 2005/0238644 A1 | 10/2005 | Mihara et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0177436 A1 | 8/2006 | Ghilardi et al. |
| 2006/0251653 A1 | 11/2006 | Okuda et al. |
| 2006/0275294 A1 | 12/2006 | Omoigui |
| 2006/0292147 A1 | 12/2006 | Yoshizaki et al. |
| 2007/0036785 A1 | 2/2007 | Kishimoto et al. |
| 2007/0036788 A1 | 2/2007 | Sheriff et al. |
| 2007/0098714 A1 | 5/2007 | Nishimoto et al. |
| 2007/0148169 A1 | 6/2007 | Yoshizaki et al. |
| 2007/0280945 A1 | 12/2007 | Stevens et al. |
| 2008/0124325 A1 | 5/2008 | Ito et al. |
| 2008/0145367 A1 | 6/2008 | Bove et al. |

FOREIGN PATENT DOCUMENTS

EP 0628639 A1 12/1994
(Continued)

OTHER PUBLICATIONS

Mihara et al., "Tocilizumab inhibits signal transduction mediated by both mIL-6R and sIL-6R . . . ", International Immunopharmacol., 2005, 5:1731-1740, Elsevier, Netherlands. Paul-Pletzer, "Tocilizumab: Blockade of interleukin-6 signaling pathway as a therapeutic strategy . . . ", Drugs of Today, 2006, 42(9):559-576, Prous Science, Barcelona, Spain.

*Primary Examiner* — Prema Mertz

(74) *Attorney, Agent, or Firm* — Izumi Yokoyama; Frank R. Cottingham; Valeta Gregg

(57) ABSTRACT

The present invention provides methods of preventing or treating rheumatoid arthritis using a fully human antibody or antigen-binding fragment thereof that specifically binds human interleukin-6 receptor (hIL-6R). The methods of the present invention may include administration of a second therapeutic agent, such as one or more of a non-steroidal anti-inflammatory drug (NSAID), a glucocorticoid, a disease-modifying anti-rheumatic drug (DMARD), or a TNF-alpha antagonist, T-cell blocker, anti-CD20 antibody, an IL-1, JAK or IL-17 antagonist, or any combination thereof.

10 Claims, No Drawings

FOREIGN PATENT DOCUMENTS

| | | |
|---|---|---|
| EP | 0409607 B1 | 10/1996 |
| EP | 0783893 A1 | 7/1997 |
| EP | 0800829 A1 | 10/1997 |
| EP | 0811384 A1 | 12/1997 |
| EP | 0628639 B1 | 6/1999 |
| EP | 0923941 A2 | 6/1999 |
| EP | 1004315 A1 | 5/2000 |
| EP | 1074268 A1 | 2/2001 |
| EP | 1108435 A1 | 6/2001 |
| EP | 1314437 A1 | 5/2003 |
| EP | 1327681 A1 | 7/2003 |
| EP | 1334731 A1 | 8/2003 |
| EP | 1475100 A1 | 11/2004 |
| EP | 1475101 A1 | 11/2004 |
| EP | 0413908 B2 | 8/2005 |
| EP | 0923941 B1 | 5/2006 |
| EP | 0811384 B1 | 6/2006 |
| EP | 1108435 B1 | 1/2007 |
| EP | 1810980 A1 | 7/2007 |
| EP | 1074268 B1 | 1/2008 |
| EP | 1334731 B1 | 2/2008 |
| EP | 1004315 B1 | 5/2008 |
| FR | 2694767 A1 | 2/1994 |
| WO | 95/09873 A1 | 4/1995 |
| WO | 2004/096273 A1 | 11/2004 |
| WO | 2005/028514 A1 | 3/2005 |
| WO | 2007/143168 A2 | 12/2007 |
| WO | 2008/020079 A1 | 2/2008 |
| WO | 2008/049897 A1 | 5/2008 |
| WO | 2008/145142 A1 | 12/2008 |
| WO | 2009/095489 A2 | 8/2009 |
| WO | 2009/109584 A1 | 9/2009 |

SEQUENCE LISTING

```
<160> NUMBER OF SEQ ID NOS: 251

<210> SEQ ID NO 1
<211> LENGTH: 358
<212> TYPE: PRT
<213> ORGANISM: Homo sapiens
<220> FEATURE:

<400> SEQUENCE: 1
```

Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
             20                  25                  30

Gly Val Leu Thr Ser Leu Pro Gly Asp Ser Val Thr Leu Thr Cys Pro
         35                  40                  45

Gly Val Glu Pro Glu Asp Asn Ala Thr Val His Trp Val Leu Arg Lys
     50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp

```
                225                 230                 235                 240
Pro His Ser Trp Asn Ser Ser Phe Tyr Arg Leu Arg Phe Glu Leu Arg
                            245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp
            355

<210> SEQ ID NO 2
<211> LENGTH: 379
<212> TYPE: DNA
<213> ORGANISM: Artificial Sequence
<220> FEATURE:
<223> OTHER INFORMATION: Synthetic

<400> SEQUENCE: 2
gaagtgcagc tggtggagtc tgggggaaac ttggtacagc ctggcaggtc cctgagactc      60
tcctgtgcag cctctggatt catctttgat gattatgcca tgcactgggt ccggcaagct     120
ccagggaagg gcctggagtg gtctcaggt attagttgga atagtggtag cataggctat      180
gcggactctg tgaagggccg attcaccatc tccagagaca cgccaagaa ctccctgtat      240 ctgcaaatga acagtctgag agctgaggac acggccttgt attactgtgc aaaagatgga     300
ggcagcagct ggttaccgtt cgtctactac tacggtatgg acgtctgggg ccaagggacc     360
acggtcaccg tctcgtcag                                                  379

<210> SEQ ID NO 3
<211> LENGTH: 126
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110
```

```
Met Asp Val Trp Gly Gln Gly Thr Thr Val Thr Val Ser Ser
        115                 120                 125
```

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ggattcatct ttgatgatta tgcc                                        24

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

```
Gly Phe Ile Phe Asp Asp Tyr Ala
 1               5
```

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
attagttgga atagtggtag cata                                        24

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

```
Ile Ser Trp Asn Ser Gly Ser Ile
 1               5
```

<210> SEQ ID NO 8
<211> LENGTH: 57
<212> TYPE: DNA
<213> ORGANISM: Artificial Sequence
<220> FEATURE:
<223> OTHER INFORMATION: Synthetic

<400> SEQUENCE: 8
gcaaaagatg gaggcagcag ctggttaccg ttcgtctact actacggtat ggacgtc    57

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

```
Ala Lys Asp Gly Gly Ser Ser Trp Leu Pro Phe Val Tyr Tyr Tyr Gly
 1               5                  10                  15

Met Asp Val
```

<210> SEQ ID NO 10
<211> LENGTH: 325
<212> TYPE: DNA
<213> ORGANISM: Artificial Sequence
<220> FEATURE:
<223> OTHER INFORMATION: Synthetic

<400> SEQUENCE: 10

```
gaaatagtga tgacgcagtc tccagccacc ctgtctgtgt ctcccgggga aagagccacc      60
ctctcctgca gggccagtca gagtattagc agcaactttg cctggtacca gcagaaacct     120
ggccaggctc ccaggctcct catctatggt gcatccacca gggccactgg tatcccagcc     180
aggttcagtg gcagtgggtc tgggacagac ttcactctca ccatcagcag cctgcagtct     240
gaagattttg cagtttatta ctgtcagcag tatagtagct ggcctccgta cacttttggc     300
caggggacca agctggagat caaac                                           325
```

<210> SEQ ID NO 11
<211> LENGTH: 108
<212> TYPE: PRT
<213> ORGANISM: Artificial Sequence
<220> FEATURE:
<223> OTHER INFORMATION: Synthetic

<400> SEQUENCE: 11

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Ser Asn
            20                  25                  30

Phe Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105
```

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12

```
cagagtatta gcagcaac                                                    18
```

<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

```
Gln Ser Ile Ser Ser Asn
 1               5
```

```
<210> SEQ ID NO 14
<211> LENGTH: 9
<212> TYPE: DNA
<213> ORGANISM: Artificial Sequence
<220> FEATURE:
<223> OTHER INFORMATION: Synthetic

<400> SEQUENCE: 14 ggtgcatcc                                                                  9

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Gly Ala Ser
 1

<210> SEQ ID NO 16
<211> LENGTH: 30
<212> TYPE: DNA
<213> ORGANISM: Artificial Sequence
<220> FEATURE:
<223> OTHER INFORMATION: Synthetic

<400> SEQUENCE: 16
cagcagtata gtagctggcc tccgtacact                                           30

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gln Gln Tyr Ser Ser Trp Pro Pro Tyr Thr
 1               5                  10

<210> SEQ ID NO 18
<211> LENGTH: 349
<212> TYPE: DNA
<213> ORGANISM: Artificial Sequence
<220> FEATURE:
<223> OTHER INFORMATION: Synthetic

<400> SEQUENCE: 18
gaagtgcagc tggtggagtc tgggggaggc ttggttcagc ctggcaggtc cctgagactc          60
tcctgtgcag cctctagatt tacctttgat gattatgcca tgcactgggt ccggcaagct         120
ccagggaagg gcctggagtg ggtctcaggt attagttgga atagtggtag aataggttat         180
gcggactctg tgaagggccg attcaccatc tccagagaca acgccgagaa ctccctcttt         240
ctgcaaatga acgtctgag agcagaggac acggccttgt attactgtgc aaaaggccga         300
gattcttttg atatctgggg ccaagggaca atggtcaccg tctcttcag                    349

<210> SEQ ID NO 19
<211> LENGTH: 116
<212> TYPE: PRT
<213> ORGANISM: Artificial Sequence
<220> FEATURE:
<223> OTHER INFORMATION: Synthetic

<400> SEQUENCE: 19
```

```
Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Glu Asn Ser Leu Phe
65              70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
                100                 105                 110

Thr Val Ser Ser
            115
```

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
agatttacct ttgatgatta tgcc                                  24

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

```
Arg Phe Thr Phe Asp Asp Tyr Ala
1               5
```

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
attagttgga atagtggtag aata                                  24

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

```
Ile Ser Trp Asn Ser Gly Arg Ile
1               5
```

<210> SEQ ID NO 24
<211> LENGTH: 27
<212> TYPE: DNA
<213> ORGANISM: Artificial Sequence
<220> FEATURE:
<223> OTHER INFORMATION: Synthetic

<400> SEQUENCE: 24
gcaaaaggcc gagattcttt tgatatc    27

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ala Lys Gly Arg Asp Ser Phe Asp Ile
 1               5

<210> SEQ ID NO 26
<211> LENGTH: 322
<212> TYPE: DNA
<213> ORGANISM: Artificial Sequence
<220> FEATURE:
<223> OTHER INFORMATION: Synthetic

<400> SEQUENCE: 26
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt tggaaagtgg ggtcccatca   180
aggttcagcg gcagtggatc tgggacagat ttcactctca ccatcagcag cctgcagcct   240
gaagattttg caagttatta ttgtcaacag gctaacagtt tcccgtacac ttttggccag   300
gggaccaagc tggagatcaa ac                                             322

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Gly Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Ser Tyr Tyr Cys Gln Gln Ala Asn Ser Phe Pro Tyr
                 85                  90                  95

Thr Phe Gly Gln Gly Thr Lys Leu Glu Ile Lys
            100                 105

<210> SEQ ID NO 28
<211> LENGTH: 18
<212> TYPE: DNA
<213> ORGANISM: Artificial Sequence
<220> FEATURE:
<223> OTHER INFORMATION: Synthetic

```
<400> SEQUENCE: 28
cagggtatta gcagctgg                                                    18

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Gln Gly Ile Ser Ser Trp
 1               5

<210> SEQ ID NO 30
<211> LENGTH: 9
<212> TYPE: DNA
<213> ORGANISM: Artificial Sequence
<220> FEATURE:
<223> OTHER INFORMATION: Synthetic

<400> SEQUENCE: 30 ggtgcatcc                                                               9

<210> SEQ ID NO 31
<211> LENGTH: 3
<212> TYPE: PRT
<213> ORGANISM: Artificial Sequence
<220> FEATURE:
<223> OTHER INFORMATION: Synthetic

<400> SEQUENCE: 31

Gly Ala Ser
 1

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
caacaggcta acagtttccc gtacact                                          27

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gln Gln Ala Asn Ser Phe Pro Tyr Thr
 1               5

<210> SEQ ID NO 34
<211> LENGTH: 370
<212> TYPE: DNA
<213> ORGANISM: Artificial Sequence
<220> FEATURE:
<223> OTHER INFORMATION: Synthetic

<400> SEQUENCE: 34
caggttcagc tggtgcagtc tggagctgag ctgaagaagc ctggggcctc agtgaaggtc      60
```

```
tcctgcaagg cttctggtta cacttttacc cattatggta tcagctgggt gcgacaggcc    120
cctggacaag ggcttgagtg gatgggatgg atcagcgctt acaatgatga cacaaactat    180
gcacagaagt tccaggggag agtcaccatg accacagaca catccacgag cacagcctac    240
atggagctga ggagcctgag atctgacgac acggccgttt attactgtgc gagagaagcg    300
cagctcgtcc tctactacta ctacggtatg gacgtctggg gccaaggac  acacggtcacc    360 gtctcctcag                                                           370
```

<210> SEQ ID NO 35
<211> LENGTH: 123
<212> TYPE: PRT
<213> ORGANISM: Artificial Sequence
<220> FEATURE:
<223> OTHER INFORMATION: Synthetic

<400> SEQUENCE: 35

```
Gln Val Gln Leu Val Gln Ser Gly Ala Glu Leu Lys Lys Pro Gly Ala
 1               5                  10                  15

Ser Val Lys Val Ser Cys Lys Ala Ser Gly Tyr Thr Phe Thr His Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Tyr Gly Met Asp Val
            100                 105                 110

Trp Gly Gln Gly Thr Thr Val Thr Val Ser Ser
        115                 120
```

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36

```
ggttacactt ttacccatta tggt                                            24
```

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

```
Gly Tyr Thr Phe Thr His Tyr Gly
 1               5
```

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
atcagcgctt acaatgatga caca                                              24

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Ile Ser Ala Tyr Asn Asp Asp Thr
 1               5

<210> SEQ ID NO 40
<211> LENGTH: 48
<212> TYPE: DNA
<213> ORGANISM: Artificial Sequence
<220> FEATURE:
<223> OTHER INFORMATION: Synthetic

<400> SEQUENCE: 40
gcgagagaag cgcagctcgt cctctactac tactacggta tggacgtc                    48

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Ala Arg Glu Ala Gln Leu Val Leu Tyr Tyr Tyr Tyr Gly Met Asp Val
 1               5                  10                  15

<210> SEQ ID NO 42
<211> LENGTH: 322
<212> TYPE: DNA
<213> ORGANISM: Artificial Sequence
<220> FEATURE:
<223> OTHER INFORMATION: Synthetic

<400> SEQUENCE: 42
gaaattgtgt tgacacagtc tccagccacc ctgtctttgt ctccagggga aagagccacc        60
ctctcctgca gggccagtca gagtgttagc agcttcttag cctggaacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgccagcag cgtaacaatt ggccgtacat ttttggccag       300
gggaccaagc tggagatcag ac                                               322

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile

```
                 35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Pro Tyr
                 85                  90                  95

Ile Phe Gly Gln Gly Thr Lys Leu Glu Ile Arg
            100                 105

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
cagagtgtta gcagcttc                                                       18

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Gln Ser Val Ser Ser Phe
 1               5

<210> SEQ ID NO 46
<211> LENGTH: 9
<212> TYPE: DNA
<213> ORGANISM: Artificial Sequence
<220> FEATURE:
<223> OTHER INFORMATION: Synthetic

<400> SEQUENCE: 46 gatgcatcc                                                                  9

<210> SEQ ID NO 47
<211> LENGTH: 3
<212> TYPE: PRT
<213> ORGANISM: Artificial Sequence
<220> FEATURE:
<223> OTHER INFORMATION: Synthetic

<400> SEQUENCE: 47

Asp Ala Ser
 1

<210> SEQ ID NO 48
<211> LENGTH: 27
<212> TYPE: DNA
<213> ORGANISM: Artificial Sequence
<220> FEATURE:
<223> OTHER INFORMATION: Synthetic

<400> SEQUENCE: 48
cagcagcgta acaattggcc gtacatt                                             27

<210> SEQ ID NO 49
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 49

Gln Gln Arg Asn Asn Trp Pro Tyr Ile
  1               5

<210> SEQ ID NO 50
<211> LENGTH: 370
<212> TYPE: DNA
<213> ORGANISM: Artificial Sequence
<220> FEATURE:
<223> OTHER INFORMATION: Synthetic

<400> SEQUENCE: 50
caggttcagc tggtgcagtc tggagctgag gtgaagaagc ctggggcctc agtgaaggtc      60
tcctgcaagg cttctggtta cacctttacc agttatggta tcagctgggt gcgacaggcc    120
cctggacaag gcttgagtg gatgggatgg atcagcgctt acaatgatga cacaaactat     180
gcacagaagt tccaggggag agtcaccatg accacagaca catccacgag cacagcctac    240
atggagctga ggagcctgag atctgacgac acggccgttt attactgtgc gagagaagcg    300
cagctcgtcc tctactacta ctacggtatg gacgtctggg gccaaggaca cacggtcacc    360
gtctcctcag                                                            370

<210> SEQ ID NO 51
<211> LENGTH: 123
<212> TYPE: PRT
<213> ORGANISM: Artificial Sequence
<220> FEATURE:
<223> OTHER INFORMATION: Synthetic

<400> SEQUENCE: 51

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Asp Asp Thr Asn Tyr Ala Gln Lys Phe
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ala Gln Leu Val Leu Tyr Tyr Tyr Tyr Gly Met Asp Val
            100                 105                 110

Trp Gly Gln Gly Thr Thr Val Thr Val Ser Ser
        115                 120

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
ggttacacct ttaccagtta tggt                                             24
```

```
<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Gly Tyr Thr Phe Thr Ser Tyr Gly
 1               5

<210> SEQ ID NO 54
<211> LENGTH: 24
<212> TYPE: DNA
<213> ORGANISM: Artificial Sequence
<220> FEATURE:
<223> OTHER INFORMATION: Synthetic

<400> SEQUENCE: 54
atcagcgctt acaatgatga caca                                                24

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Ile Ser Ala Tyr Asn Asp Asp Thr
 1               5

<210> SEQ ID NO 56
<211> LENGTH: 48
<212> TYPE: DNA
<213> ORGANISM: Artificial Sequence
<220> FEATURE:
<223> OTHER INFORMATION: Synthetic

<400> SEQUENCE: 56
gcgagagaag cgcagctcgt cctctactac tactacggta tggacgtc                      48

<210> SEQ ID NO 57
<211> LENGTH: 16
<212> TYPE: PRT
<213> ORGANISM: Artificial Sequence
<220> FEATURE:
<223> OTHER INFORMATION: Synthetic

<400> SEQUENCE: 57

Ala Arg Glu Ala Gln Leu Val Leu Tyr Tyr Tyr Tyr Gly Met Asp Val
 1               5                  10                  15

<210> SEQ ID NO 58
<211> LENGTH: 322
<212> TYPE: DNA
<213> ORGANISM: Artificial Sequence
<220> FEATURE:
<223> OTHER INFORMATION: Synthetic

<400> SEQUENCE: 58
gaaattgtgt tgacacagtc tccagccacc ctgtctttgt ctccagggga aagagccacc          60
ctctcctgca gggccagtca gagtgttagc agcttcttag cctggaacca acagaaacct         120
ggccaggctc ccaggctcct catctatgat gcatccaaca gggccactgg catcccagcc         180
aggttcagtg gcagtgggtc tgggacagac ttcactctca ccatcagcag cctagagcct         240
```

```
gaagattttg cagtttatta ctgccagcag cgtagcaatt ggccgtacat ttttggccag    300
gggaccaagc tggagatcaa ac                                             322
```

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Phe
             20                  25                  30

Leu Ala Trp Asn Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Tyr
                 85                  90                  95

Ile Phe Gly Gln Gly Thr Lys Leu Glu Ile Lys
            100                 105
```

<210> SEQ ID NO 60
<211> LENGTH: 18
<212> TYPE: DNA
<213> ORGANISM: Artificial Sequence
<220> FEATURE:
<223> OTHER INFORMATION: Synthetic

<400> SEQUENCE: 60

```
cagagtgtta gcagcttc                                                   18
```

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

```
Gln Ser Val Ser Ser Phe
  1               5
```

<210> SEQ ID NO 62
<211> LENGTH: 9
<212> TYPE: DNA
<213> ORGANISM: Artificial Sequence
<220> FEATURE:
<223> OTHER INFORMATION: Synthetic

<400> SEQUENCE: 62

```
gatgcatcc                                                              9
```

<210> SEQ ID NO 63
<211> LENGTH: 3
<212> TYPE: PRT
<213> ORGANISM: Artificial Sequence
<220> FEATURE:
<223> OTHER INFORMATION: Synthetic

<400> SEQUENCE: 63

Asp Ala Ser
1

<210> SEQ ID NO 64
<211> LENGTH: 27
<212> TYPE: DNA
<213> ORGANISM: Artificial Sequence
<220> FEATURE:
<223> OTHER INFORMATION: Synthetic

<400> SEQUENCE: 64
cagcagcgta gcaattggcc gtacatt                                          27

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Gln Gln Arg Ser Asn Trp Pro Tyr Ile
1               5

<210> SEQ ID NO 66
<211> LENGTH: 349
<212> TYPE: DNA
<213> ORGANISM: Artificial Sequence
<220> FEATURE:
<223> OTHER INFORMATION: Synthetic

<400> SEQUENCE: 66
gaagtgcagc tggtggagtc tgggggaggc ttggtacagc ctggcaggtc cctgagactc        60
tcctgtgcag cctctggatt cacctttgat gattatgccc tgcactgggt ccggcaagct       120
ccagggaagg gcctggagtg ggtctcaggt gttagttgga atggtggtag aataggctat       180
gcggactctg tgaaaggccg attcaccatc tccagagaca acgccaagaa ctccctcttt       240
ctgcaaatga acagtctgag agttgaggac acggccttgt attattgtgc aaaaggccgg       300
gatgcttttg atatctgggg ccaagggaca ttggtcaccg tctcttcag                   349

<210> SEQ ID NO 67
<211> LENGTH: 116
<212> TYPE: PRT
<213> ORGANISM: Artificial Sequence
<220> FEATURE:
<223> OTHER INFORMATION: Synthetic

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

```
Ala Lys Gly Arg Asp Ala Phe Asp Ile Trp Gly Gln Gly Thr Leu Val
            100                 105                 110
Thr Val Ser Ser
        115

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
ggattcacct ttgatgatta tgcc                                          24

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Gly Phe Thr Phe Asp Asp Tyr Ala
1               5

<210> SEQ ID NO 70
<211> LENGTH: 24
<212> TYPE: DNA
<213> ORGANISM: Artificial Sequence
<220> FEATURE:
<223> OTHER INFORMATION: Synthetic

<400> SEQUENCE: 70
gttagttgga atggtggtag aata                                          24

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Val Ser Trp Asn Gly Gly Arg Ile
1               5

<210> SEQ ID NO 72
<211> LENGTH: 27
<212> TYPE: DNA
<213> ORGANISM: Artificial Sequence
<220> FEATURE:
<223> OTHER INFORMATION: Synthetic

<400> SEQUENCE: 72
gcaaaaggcc gggatgcttt tgatatc                                       27

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Ala Lys Gly Arg Asp Ala Phe Asp Ile
1               5
```

<210> SEQ ID NO 74
<211> LENGTH: 325
<212> TYPE: DNA
<213> ORGANISM: Artificial Sequence
<220> FEATURE:
<223> OTHER INFORMATION: Synthetic

<400> SEQUENCE: 74

```
gaaattgtgt tgacacagtc tccagccacc ctgtctttgt ctccagggga aagagccacc    60
ctctcctgca gggccagtca gagtgttagc agttacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg catttattat ctgtcagcag cgtaacaacc ggcctccatt cactttcggc   300
cctgggacca aagtggatgt cagac                                         325
```

<210> SEQ ID NO 75
<211> LENGTH: 108
<212> TYPE: PRT
<213> ORGANISM: Artificial Sequence
<220> FEATURE:
<223> OTHER INFORMATION: Synthetic

<400> SEQUENCE: 75

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105
```

<210> SEQ ID NO 76
<211> LENGTH: 18
<212> TYPE: DNA
<213> ORGANISM: Artificial Sequence
<220> FEATURE:
<223> OTHER INFORMATION: Synthetic

<400> SEQUENCE: 76

```
cagagtgtta gcagttac                                                   18
```

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

```
Gln Ser Val Ser Ser Tyr
 1               5
```

<210> SEQ ID NO 78
<211> LENGTH: 9
<212> TYPE: DNA
<213> ORGANISM: Artificial Sequence
<220> FEATURE:
<223> OTHER INFORMATION: Synthetic

<400> SEQUENCE: 78 gatgcatcc                                                                 9

<210> SEQ ID NO 79
<211> LENGTH: 3
<212> TYPE: PRT
<213> ORGANISM: Artificial Sequence
<220> FEATURE:
<223> OTHER INFORMATION: Synthetic

<400> SEQUENCE: 79

Asp Ala Ser
 1

<210> SEQ ID NO 80
<211> LENGTH: 30
<212> TYPE: DNA
<213> ORGANISM: Artificial Sequence
<220> FEATURE:
<223> OTHER INFORMATION: Synthetic

<400> SEQUENCE: 80
cagcagcgta acaaccggcc tccattcact                                         30

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gln Gln Arg Asn Asn Arg Pro Pro Phe Thr
 1               5                  10

<210> SEQ ID NO 82
<211> LENGTH: 370
<212> TYPE: DNA
<213> ORGANISM: Artificial Sequence
<220> FEATURE:
<223> OTHER INFORMATION: Synthetic

<400> SEQUENCE: 82
caggttcagc tggtgcagtc tggagctgag gtgaagaagc ctggggcctc agtgaaggtc         60
tcctgtaagg cttctggttt caacttcttt cattatggta tcacctgggt gcgacaggcc        120
cctggacaag ggcttgagtg gatgggatgg atcagcactt acaatggtga cacaatctat        180
gcacagaagg tccagggcag agtcaccatg accacagaca cagccacgag cacggcctat        240
atggaactga ggagcctgag atctgacgac acggccgtgt attactgtgc gagatcggaa        300
cagcaggtgg actactactt ctacggtatg gacgtctggg gccaagggac cacggtcacc        360
gtttcctcag                                                              370

<210> SEQ ID NO 83
<211> LENGTH: 123
<212> TYPE: PRT
<213> ORGANISM: Artificial Sequence
<220> FEATURE:
<223> OTHER INFORMATION: Synthetic

<400> SEQUENCE: 83

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Asn Phe Phe His Tyr
            20                  25                  30
Gly Ile Thr Trp Val Arg Gln Ala Pro Gly Gln Gly Leu Glu Trp Met
        35                  40                  45
Gly Trp Ile Ser Thr Tyr Asn Gly Asp Thr Ile Tyr Ala Gln Lys Val
    50                  55                  60
Gln Gly Arg Val Thr Met Thr Thr Asp Thr Ala Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Ser Glu Gln Gln Val Asp Tyr Tyr Phe Tyr Gly Met Asp Val
            100                 105                 110
Trp Gly Gln Gly Thr Thr Val Thr Val Ser Ser
        115                 120
```

<210> SEQ ID NO 84
<211> LENGTH: 24
<212> TYPE: DNA
<213> ORGANISM: Artificial Sequence
<220> FEATURE:
<223> OTHER INFORMATION: Synthetic

<400> SEQUENCE: 84
ggtttcaact tctttcatta tggt                                          24

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

```
Gly Phe Asn Phe Phe His Tyr Gly
1               5
```

<210> SEQ ID NO 86
<211> LENGTH: 24
<212> TYPE: DNA
<213> ORGANISM: Artificial Sequence
<220> FEATURE:
<223> OTHER INFORMATION: Synthetic

<400> SEQUENCE: 86
atcagcactt acaatggtga caca                                          24

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

```
Ile Ser Thr Tyr Asn Gly Asp Thr
1               5
```

<210> SEQ ID NO 88
<211> LENGTH: 48

```
<212> TYPE: DNA
<213> ORGANISM: Artificial Sequence
<220> FEATURE:
<223> OTHER INFORMATION: Synthetic

<400> SEQUENCE: 88
gcgagatcgg aacagcaggt ggactactac ttctacggta tggacgtc                    48

<210> SEQ ID NO 89
<211> LENGTH: 16
<212> TYPE: PRT
<213> ORGANISM: Artificial Sequence
<220> FEATURE:
<223> OTHER INFORMATION: Synthetic

<400> SEQUENCE: 89

Ala Arg Ser Glu Gln Gln Val Asp Tyr Tyr Phe Tyr Gly Met Asp Val
 1               5                  10                  15

<210> SEQ ID NO 90
<211> LENGTH: 325
<212> TYPE: DNA
<213> ORGANISM: Artificial Sequence
<220> FEATURE:
<223> OTHER INFORMATION: Synthetic

<400> SEQUENCE: 90
gaaattgtgt tgacacagtc tccagccacc ctgtctttgt ctccagggga aagagccacc        60
ctctcctgca gggccagtca gagtgttagc agttacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg catttattac tgtcagcag cgtaacaacc ggcctccatt cactttcggc       300
cctgggacca agtggatgt cagac                                              325

<210> SEQ ID NO 91
<211> LENGTH: 108
<212> TYPE: PRT
<213> ORGANISM: Artificial Sequence
<220> FEATURE:
<223> OTHER INFORMATION: Synthetic

<400> SEQUENCE: 91

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105

<210> SEQ ID NO 92
<211> LENGTH: 18
<212> TYPE: DNA
<213> ORGANISM: Artificial Sequence
```

```
<220> FEATURE:
<223> OTHER INFORMATION: Synthetic

<400> SEQUENCE: 92
cagagtgtta gcagttac                                                   18

<210> SEQ ID NO 93
<211> LENGTH: 6
<212> TYPE: PRT
<213> ORGANISM: Artificial Sequence
<220> FEATURE:
<223> OTHER INFORMATION: Synthetic

<400> SEQUENCE: 93

Gln Ser Val Ser Ser Tyr
 1               5

<210> SEQ ID NO 94
<211> LENGTH: 9
<212> TYPE: DNA
<213> ORGANISM: Artificial Sequence
<220> FEATURE:
<223> OTHER INFORMATION: Synthetic

<400> SEQUENCE: 94 gatgcatcc                                                              9

<210> SEQ ID NO 95
<211> LENGTH: 3
<212> TYPE: PRT
<213> ORGANISM: Artificial Sequence
<220> FEATURE:
<223> OTHER INFORMATION: Synthetic

<400> SEQUENCE: 95

Asp Ala Ser
 1

<210> SEQ ID NO 96
<211> LENGTH: 30
<212> TYPE: DNA
<213> ORGANISM: Artificial Sequence
<220> FEATURE:
<223> OTHER INFORMATION: Synthetic

<400> SEQUENCE: 96
cagcagcgta acaaccggcc tccattcact                                       30

<210> SEQ ID NO 97
<211> LENGTH: 10
<212> TYPE: PRT
<213> ORGANISM: Artificial Sequence
<220> FEATURE:
<223> OTHER INFORMATION: Synthetic

<400> SEQUENCE: 97

Gln Gln Arg Asn Asn Arg Pro Pro Phe Thr
 1               5                  10

<210> SEQ ID NO 98
<211> LENGTH: 370
<212> TYPE: DNA
<213> ORGANISM: Artificial Sequence
<220> FEATURE:
<223> OTHER INFORMATION: Synthetic

<400> SEQUENCE: 98
```

```
caggttcagc tggtgcagtc tggagctgag gtgaagaagc ctggggcctc agtgaaggtc      60
tcctgtaagg cttctggttt caacttcttt cattatggta tcacctgggt gcgacaggcc     120
cctggacaag gcttgagtg gatgggatgg atcagcactt acaatggtga cacaatctat      180
gcacagaagt tccagggcag agtcaccatg accacagaca cagccacgag cacggcctat     240
atggaactga ggagcctgag atctgacgac acggccgtgt attactgtgc gagatcggaa     300
cagcaggtgg actactactt ctacggtatg gacgtctggg gccaagggac cacggtcacc     360
gtttcctcag                                                           370
```

<210> SEQ ID NO 99
<211> LENGTH: 123
<212> TYPE: PRT
<213> ORGANISM: Artificial Sequence
<220> FEATURE:
<223> OTHER INFORMATION: Synthetic

<400> SEQUENCE: 99

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Phe Phe His Tyr
             20                  25                  30

Gly Ile Thr Trp Val Arg Gln Ala Pro Gly Gln Gly Leu Glu Trp Met
         35                  40                  45

Gly Trp Ile Ser Thr Tyr Asn Gly Asp Thr Ile Tyr Ala Gln Lys Val
     50                  55                  60

Gln Gly Arg Val Thr Met Thr Thr Asp Thr Ala Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Glu Gln Gln Val Asp Tyr Tyr Phe Tyr Gly Met Asp Val
            100                 105                 110

Trp Gly Gln Gly Thr Thr Val Thr Val Ser Ser
        115                 120
```

<210> SEQ ID NO 100
<211> LENGTH: 24
<212> TYPE: DNA
<213> ORGANISM: Artificial Sequence
<220> FEATURE:
<223> OTHER INFORMATION: Synthetic

<400> SEQUENCE: 100

```
ggtttcaact tctttcatta tggt                                            24
```

<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

```
Gly Phe Asn Phe Phe His Tyr Gly
 1               5
```

<210> SEQ ID NO 102
<211> LENGTH: 24
<212> TYPE: DNA
<213> ORGANISM: Artificial Sequence
<220> FEATURE:
<223> OTHER INFORMATION: Synthetic

<400> SEQUENCE: 102
atcagcactt acaatggtga caca    24

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Ile Ser Thr Tyr Asn Gly Asp Thr
1               5

<210> SEQ ID NO 104
<211> LENGTH: 48
<212> TYPE: DNA
<213> ORGANISM: Artificial Sequence
<220> FEATURE:
<223> OTHER INFORMATION: Synthetic

<400> SEQUENCE: 104
gcgagatcgg aacagcaggt ggactactac ttctacggta tggacgtc    48

<210> SEQ ID NO 105
<211> LENGTH: 16
<212> TYPE: PRT
<213> ORGANISM: Artificial Sequence
<220> FEATURE:
<223> OTHER INFORMATION: Synthetic

<400> SEQUENCE: 105

Ala Arg Ser Glu Gln Gln Val Asp Tyr Tyr Phe Tyr Gly Met Asp Val
1               5                   10                  15

<210> SEQ ID NO 106
<211> LENGTH: 325
<212> TYPE: DNA
<213> ORGANISM: Artificial Sequence
<220> FEATURE:
<223> OTHER INFORMATION: Synthetic

<400> SEQUENCE: 106
gaaattgtgt tgacacagtc tccagccacc ctgtctttgt ctccagggga aagagccacc    60
ctctcctgca gggccagtca gagtgttagc agttacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg catttattc tgtcagcag cgtaacaacc ggcctccatt cactttcggc    300
cctgggacca agtggatgt cagac    325

<210> SEQ ID NO 107
<211> LENGTH: 108
<212> TYPE: PRT
<213> ORGANISM: Artificial Sequence
<220> FEATURE:
<223> OTHER INFORMATION: Synthetic

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
                100                 105
```

<210> SEQ ID NO 108
<211> LENGTH: 18
<212> TYPE: DNA
<213> ORGANISM: Artificial Sequence
<220> FEATURE:
<223> OTHER INFORMATION: Synthetic

<400> SEQUENCE: 108
cagagtgtta gcagttac                                                 18

<210> SEQ ID NO 109
<211> LENGTH: 6
<212> TYPE: PRT
<213> ORGANISM: Artificial Sequence
<220> FEATURE:
<223> OTHER INFORMATION: Synthetic

<400> SEQUENCE: 109

```
Gln Ser Val Ser Ser Tyr
 1               5
```

<210> SEQ ID NO 110
<211> LENGTH: 9
<212> TYPE: DNA
<213> ORGANISM: Artificial Sequence
<220> FEATURE:
<223> OTHER INFORMATION: Synthetic

<400> SEQUENCE: 110 gatgcatcc                                                            9

<210> SEQ ID NO 111
<211> LENGTH: 3
<212> TYPE: PRT
<213> ORGANISM: Artificial Sequence
<220> FEATURE:
<223> OTHER INFORMATION: Synthetic

<400> SEQUENCE: 111

```
Asp Ala Ser
 1
```

<210> SEQ ID NO 112
<211> LENGTH: 30
<212> TYPE: DNA
<213> ORGANISM: Artificial Sequence
<220> FEATURE:
<223> OTHER INFORMATION: Synthetic

<400> SEQUENCE: 112
cagcagcgta acaaccggcc tccattcact                                    30

<210> SEQ ID NO 113

```
<211> LENGTH: 10
<212> TYPE: PRT
<213> ORGANISM: Artificial Sequence
<220> FEATURE:
<223> OTHER INFORMATION: Synthetic

<400> SEQUENCE: 113

Gln Gln Arg Asn Asn Arg Pro Pro Phe Thr
 1               5                  10

<210> SEQ ID NO 114
<211> LENGTH: 361
<212> TYPE: DNA
<213> ORGANISM: Artificial Sequence
<220> FEATURE:
<223> OTHER INFORMATION: Synthetic

<400> SEQUENCE: 114
caggtgcagc tggtgcagtc tggggctgag gtgaaagagc ctggggcctc agtgaagatc      60
tcctgcaagg cttctggata caccttcacc tcttatgata tcatctgggt gcgacaggcc     120
actggacaag gcttgagtg gatgggatgg atgaacccaa acagtggtga cagaggctat      180
acacagaacc tccagggcag agtcaccttg accaggaca cctccataag tacagtctac      240
atggaactga gcagcctgag atctgaggac acggccgtat attattgtgc gcgagactac     300
agtaaccact actacggttt ggacgtctgg ggccaaggga ccacggtcac tgtctcctca     360
g                                                                    361

<210> SEQ ID NO 115
<211> LENGTH: 120
<212> TYPE: PRT
<213> ORGANISM: Artificial Sequence
<220> FEATURE:
<223> OTHER INFORMATION: Synthetic

<400> SEQUENCE: 115

Gln Val Gln Leu Val Gln Ser Gly Ala Glu Val Lys Glu Pro Gly Ala
 1               5                  10                  15

Ser Val Lys Ile Ser Cys Lys Ala Ser Gly Tyr Thr Phe Thr Ser Tyr
             20                  25                  30

Asp Ile Ile Trp Val Arg Gln Ala Thr Gly Gln Gly Leu Glu Trp Met
         35                  40                  45

Gly Trp Met Asn Pro Asn Ser Gly Asp Arg Gly Tyr Thr Gln Asn Leu
     50                  55                  60

Gln Gly Arg Val Thr Leu Thr Arg Asp Thr Ser Ile Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asn His Tyr Tyr Gly Leu Asp Val Trp Gly Gln
            100                 105                 110

Gly Thr Thr Val Thr Val Ser Ser
        115                 120

<210> SEQ ID NO 116
<211> LENGTH: 24
<212> TYPE: DNA
<213> ORGANISM: Artificial Sequence
<220> FEATURE:
<223> OTHER INFORMATION: Synthetic

<400> SEQUENCE: 116
ggatacacct tcacctctta tgat                                            24
```

<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117

Gly Tyr Thr Phe Thr Ser Tyr Asp
 1               5

<210> SEQ ID NO 118
<211> LENGTH: 24
<212> TYPE: DNA
<213> ORGANISM: Artificial Sequence
<220> FEATURE:
<223> OTHER INFORMATION: Synthetic

<400> SEQUENCE: 118
atgaacccaa acagtggtga caga                                              24

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

Met Asn Pro Asn Ser Gly Asp Arg
 1               5

<210> SEQ ID NO 120
<211> LENGTH: 39
<212> TYPE: DNA
<213> ORGANISM: Artificial Sequence
<220> FEATURE:
<223> OTHER INFORMATION: Synthetic

<400> SEQUENCE: 120
gcgcgagact acagtaacca ctactacggt ttggacgtc                              39

<210> SEQ ID NO 121
<211> LENGTH: 13
<212> TYPE: PRT
<213> ORGANISM: Artificial Sequence
<220> FEATURE:
<223> OTHER INFORMATION: Synthetic

<400> SEQUENCE: 121

Ala Arg Asp Tyr Ser Asn His Tyr Tyr Gly Leu Asp Val
 1               5                   10

<210> SEQ ID NO 122
<211> LENGTH: 322
<212> TYPE: DNA
<213> ORGANISM: Artificial Sequence
<220> FEATURE:
<223> OTHER INFORMATION: Synthetic

<400> SEQUENCE: 122
gacatccagt tgacccagtc tccatccttc ctgtctgcat ctgtaggaga cagagtcacc       60
atcacttgct gggccagtca ggacattagc aattatttag cctggtatca gcaaaaacca      120
gggaaagccc ctaagctcct gatctttgtt gcatccactt tgcagagtgg ggtcccatca      180

```
aggttcagcg gcagtggatc tgggacagaa ttcactctca caatcagtag cctgcagcct    240
gaagattttg caacttatta ctgtcaacag tttaatagtt acccgctcac tttcggcgga    300
gggaccaagg tggagatcag ac                                             322
```

<210> SEQ ID NO 123
<211> LENGTH: 107
<212> TYPE: PRT
<213> ORGANISM: Artificial Sequence
<220> FEATURE:
<223> OTHER INFORMATION: Synthetic

<400> SEQUENCE: 123

```
Asp Ile Gln Leu Thr Gln Ser Pro Ser Phe Leu Ser Ala Ser Val Gly
  1               5                  10                  15

Asp Arg Val Thr Ile Thr Cys Trp Ala Ser Gln Asp Ile Ser Asn Tyr
             20                  25                  30

Leu Ala Trp Tyr Gln Gln Lys Pro Gly Lys Ala Pro Lys Leu Leu Ile
         35                  40                  45

Phe Val Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Arg
            100                 105
```

<210> SEQ ID NO 124
<211> LENGTH: 18
<212> TYPE: DNA
<213> ORGANISM: Artificial Sequence
<220> FEATURE:
<223> OTHER INFORMATION: Synthetic

<400> SEQUENCE: 124

```
caggacatta gcaattat                                                  18
```

<210> SEQ ID NO 125
<211> LENGTH: 6
<212> TYPE: PRT
<213> ORGANISM: Artificial Sequence
<220> FEATURE:
<223> OTHER INFORMATION: Synthetic

<400> SEQUENCE: 125

```
Gln Asp Ile Ser Asn Tyr
  1               5
```

<210> SEQ ID NO 126
<211> LENGTH: 9
<212> TYPE: DNA
<213> ORGANISM: Artificial Sequence
<220> FEATURE:
<223> OTHER INFORMATION: Synthetic

<400> SEQUENCE: 126

```
gttgcatcc                                                             9
```

<210> SEQ ID NO 127
<211> LENGTH: 3
<212> TYPE: PRT
<213> ORGANISM: Artificial Sequence
<220> FEATURE:

<223> OTHER INFORMATION: Synthetic

<400> SEQUENCE: 127

Val Ala Ser
 1

<210> SEQ ID NO 128
<211> LENGTH: 30
<212> TYPE: DNA
<213> ORGANISM: Artificial Sequence
<220> FEATURE:
<223> OTHER INFORMATION: Synthetic

<400> SEQUENCE: 128
caacagttta atagttaccc gctcactttc            30

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

Gln Gln Phe Asn Ser Tyr Pro Leu Thr
 1               5

<210> SEQ ID NO 130
<211> LENGTH: 370
<212> TYPE: DNA
<213> ORGANISM: Artificial Sequence
<220> FEATURE:
<223> OTHER INFORMATION: Synthetic

<400> SEQUENCE: 130
caggttcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acaatgatga cacaaactat      180
gcacagaagt tccaggggag agtcaccatg accacagaca catccacgag cacagcctac     240
atggagctga ggagcctgag atctgacgac acggccgttt attactgtgc gagagaagcg     300
cagctcgtcc tctactacta ctacggtatg gacgtctggg gccaagggac cacggtcacc     360
gtctcctcag                                                            370

<210> SEQ ID NO 131
<211> LENGTH: 123
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Asp Asp Thr Asn Tyr Ala Gln Lys Phe
        50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Gly Met Asp Val
            100                 105                 110

Trp Gly Gln Gly Thr Thr Val Thr Val Ser Ser
        115                 120

<210> SEQ ID NO 132
<211> LENGTH: 24
<212> TYPE: DNA
<213> ORGANISM: Artificial Sequence
<220> FEATURE:
<223> OTHER INFORMATION: Synthetic

<400> SEQUENCE: 132
ggttacacct ttaccagtta tggt                                          24

<210> SEQ ID NO 133
<211> LENGTH: 8
<212> TYPE: PRT
<213> ORGANISM: Artificial Sequence
<220> FEATURE:
<223> OTHER INFORMATION: Synthetic

<400> SEQUENCE: 133

Gly Tyr Thr Phe Thr Ser Tyr Gly
1               5

<210> SEQ ID NO 134
<211> LENGTH: 24
<212> TYPE: DNA
<213> ORGANISM: Artificial Sequence
<220> FEATURE:
<223> OTHER INFORMATION: Synthetic

<400> SEQUENCE: 134
atcagcgctt acaatgatga caca                                          24

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Ile Ser Ala Tyr Asn Asp Asp Thr
1               5

<210> SEQ ID NO 136
<211> LENGTH: 48
<212> TYPE: DNA
<213> ORGANISM: Artificial Sequence
<220> FEATURE:
<223> OTHER INFORMATION: Synthetic

<400> SEQUENCE: 136
gcgagagaag cgcagctcgt cctctactac tactacggta tggacgtc                48

<210> SEQ ID NO 137
<211> LENGTH: 16
<212> TYPE: PRT
<213> ORGANISM: Artificial Sequence
<220> FEATURE:
<223> OTHER INFORMATION: Synthetic

<400> SEQUENCE: 137

Ala Arg Glu Ala Gln Leu Val Leu Tyr Tyr Tyr Gly Met Asp Val
 1               5                  10                  15

<210> SEQ ID NO 138
<211> LENGTH: 322
<212> TYPE: DNA
<213> ORGANISM: Artificial Sequence
<220> FEATURE:
<223> OTHER INFORMATION: Synthetic

<400> SEQUENCE: 138
gaaattgtgt tgacacagtc tccagccacc ctgtctttgt ctccagggga aagagccacc    60
ctctcctgca gggccagtca gagtgttagc agcttcttag cctggaacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgccagcag cgtagcaatt ggccgtacat ttttggccag   300
gggaccaagc tggagatcaa ac                                           322

<210> SEQ ID NO 139
<211> LENGTH: 107
<212> TYPE: PRT
<213> ORGANISM: Artificial Sequence
<220> FEATURE:
<223> OTHER INFORMATION: Synthetic

<400> SEQUENCE: 139

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Ile Phe Gly Gln Gly Thr Lys Leu Glu Ile Lys
            100                 105

<210> SEQ ID NO 140
<211> LENGTH: 18
<212> TYPE: DNA
<213> ORGANISM: Artificial Sequence
<220> FEATURE:
<223> OTHER INFORMATION: Synthetic

<400> SEQUENCE: 140
cagagtgtta gcagcttc                                                 18

<210> SEQ ID NO 141
<211> LENGTH: 6
<212> TYPE: PRT
<213> ORGANISM: Artificial Sequence
<220> FEATURE:
<223> OTHER INFORMATION: Synthetic

<400> SEQUENCE: 141

Gln Ser Val Ser Ser Phe
1               5

<210> SEQ ID NO 142
<211> LENGTH: 9
<212> TYPE: DNA
<213> ORGANISM: Artificial Sequence
<220> FEATURE:
<223> OTHER INFORMATION: Synthetic

<400> SEQUENCE: 142 gatgcatcc                                                              9

<210> SEQ ID NO 143
<211> LENGTH: 3
<212> TYPE: PRT
<213> ORGANISM: Artificial Sequence
<220> FEATURE:
<223> OTHER INFORMATION: Synthetic

<400> SEQUENCE: 143

Asp Ala Ser
1

<210> SEQ ID NO 144
<211> LENGTH: 27
<212> TYPE: DNA
<213> ORGANISM: Artificial Sequence
<220> FEATURE:
<223> OTHER INFORMATION: Synthetic

<400> SEQUENCE: 144
cagcagcgta gcaattggcc gtacatt                                          27

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Gln Gln Arg Ser Asn Trp Pro Tyr Ile
1               5

<210> SEQ ID NO 146
<211> LENGTH: 349
<212> TYPE: DNA
<213> ORGANISM: Artificial Sequence
<220> FEATURE:
<223> OTHER INFORMATION: Synthetic

<400> SEQUENCE: 146
gaagtgcagc tggtggagtc tgggggaggc ttggtacagc ctggcaggtc cctgagactc        60
tcctgtgcag cctctggatt cacctttgat gattatgccc tgcactgggt ccggcaagct       120
ccagggaagg gcctggagtg ggtctcaggt gttagttgga atggtggtag aataggctat       180
gcggactctg tgaaaggccg attcaccatc tccagagaca cgccaagaa ctccctcttt        240 ctgcaaatga acagtctgag agttgaggac acggccttgt attattgtgc aaaaggccgg       300
gatgcttttg atatctgggg ccaagggaca ttggtcaccg tctcttcag                   349

<210> SEQ ID NO 147
<211> LENGTH: 116
<212> TYPE: PRT
<213> ORGANISM: Artificial Sequence
<220> FEATURE:
<223> OTHER INFORMATION: Synthetic

<400> SEQUENCE: 147

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65              70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 148
<211> LENGTH: 24
<212> TYPE: DNA
<213> ORGANISM: Artificial Sequence
<220> FEATURE:
<223> OTHER INFORMATION: Synthetic

<400> SEQUENCE: 148
ggattcacct ttgatgatta tgcc                                          24

<210> SEQ ID NO 149
<211> LENGTH: 8
<212> TYPE: PRT
<213> ORGANISM: Artificial Sequence
<220> FEATURE:
<223> OTHER INFORMATION: Synthetic

<400> SEQUENCE: 149

Gly Phe Thr Phe Asp Asp Tyr Ala
1               5

<210> SEQ ID NO 150
<211> LENGTH: 24
<212> TYPE: DNA
<213> ORGANISM: Artificial Sequence
<220> FEATURE:
<223> OTHER INFORMATION: Synthetic

<400> SEQUENCE: 150
gttagttgga atggtggtag aata                                          24

<210> SEQ ID NO 151
<211> LENGTH: 8
<212> TYPE: PRT
<213> ORGANISM: Artificial Sequence
<220> FEATURE:
<223> OTHER INFORMATION: Synthetic

<400> SEQUENCE: 151

Val Ser Trp Asn Gly Gly Arg Ile
1               5

<210> SEQ ID NO 152
<211> LENGTH: 27
<212> TYPE: DNA
<213> ORGANISM: Artificial Sequence
<220> FEATURE:
<223> OTHER INFORMATION: Synthetic

<400> SEQUENCE: 152
gcaaaaggcc gggatgcttt tgatatc                                            27

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Ala Lys Gly Arg Asp Ala Phe Asp Ile
 1               5

<210> SEQ ID NO 154
<211> LENGTH: 322
<212> TYPE: DNA
<213> ORGANISM: Artificial Sequence
<220> FEATURE:
<223> OTHER INFORMATION: Synthetic

<400> SEQUENCE: 154
gacatccaga tgacccagtc tccatcttcc gtgtctgcat ctgtaggaga cagagtcacc        60
atcacttgtc gggcgagtca gggtattagc agctggttag cctggtatca gcagaaacca      120
gggaaagccc ctaaactcct gatctatgct gcatccagtt tgcaaagtgg ggtcccatca      180
aggttcagcg gcagtggatc tgggacagat ttcactctca ccatcagcag cctgcagcct      240
gaagattttg caacttacta ttgtcaacat gcttacagtt tcccgtacac ttttggccag      300
gggaccaagc tggagatcaa ac                                               322

<210> SEQ ID NO 155
<211> LENGTH: 107
<212> TYPE: PRT
<213> ORGANISM: Artificial Sequence
<220> FEATURE:
<223> OTHER INFORMATION: Synthetic

<400> SEQUENCE: 155

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ala Tyr Ser Phe Pro Tyr
                85                  90                  95

Thr Phe Gly Gln Gly Thr Lys Leu Glu Ile Lys
                100                 105

<210> SEQ ID NO 156
<211> LENGTH: 18

```
<212> TYPE: DNA
<213> ORGANISM: Artificial Sequence
<220> FEATURE:
<223> OTHER INFORMATION: Synthetic

<400> SEQUENCE: 156
cagggtatta gcagctgg                                                      18

<210> SEQ ID NO 157
<211> LENGTH: 6
<212> TYPE: PRT
<213> ORGANISM: Artificial Sequence
<220> FEATURE:
<223> OTHER INFORMATION: Synthetic

<400> SEQUENCE: 157

Gln Gly Ile Ser Ser Trp
 1               5

<210> SEQ ID NO 158
<211> LENGTH: 9
<212> TYPE: DNA
<213> ORGANISM: Artificial Sequence
<220> FEATURE:
<223> OTHER INFORMATION: Synthetic

<400> SEQUENCE: 158 gctgcatcc                                                                 9

<210> SEQ ID NO 159
<211> LENGTH: 3
<212> TYPE: PRT
<213> ORGANISM: Artificial Sequence
<220> FEATURE:
<223> OTHER INFORMATION: Synthetic

<400> SEQUENCE: 159

Ala Ala Ser
 1

<210> SEQ ID NO 160
<211> LENGTH: 27
<212> TYPE: DNA
<213> ORGANISM: Artificial Sequence
<220> FEATURE:
<223> OTHER INFORMATION: Synthetic

<400> SEQUENCE: 160
caacatgctt acagtttccc gtacact                                            27

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Gln His Ala Tyr Ser Phe Pro Tyr Thr
 1               5

<210> SEQ ID NO 162
<211> LENGTH: 349
<212> TYPE: DNA
<213> ORGANISM: Artificial Sequence
<220> FEATURE:
<223> OTHER INFORMATION: Synthetic
```

-continued

```
<400> SEQUENCE: 162
gaagtgcagc tggtggagtc tgggggaggc ttggtacagc ctggcaggtc cctgagactc      60
tcctgtgcag cctctggatt cacctttgat gattatgcct tgcactgggt ccggcaagct     120
ccagggaagg gcctggagtg ggtctcaggt attagttgga acagtggtag aataggctat     180
gcggactctg tgaagggccg attcaccatt tccagagaca acgccaagaa ctccctcttt     240
ctgcaaatga acagtctgag agctgaggac acggccttgt attattgtgc aaaaggccgg     300
gatgcttttg atatctgggg ccaagggaca ttggtcaccg tctcttcag                349
```

```
<210> SEQ ID NO 163
<211> LENGTH: 116
<212> TYPE: PRT
<213> ORGANISM: Artificial Sequence
<220> FEATURE:
<223> OTHER INFORMATION: Synthetic

<400> SEQUENCE: 163

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Leu His Trp Val Arg Gln Ala Pro Gly Lys Gly Leu Glu Trp Val
         35                  40                  45

Ser Gly Ile Ser Trp Asn Ser Gly Arg Ile Gly Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Leu Tyr Tyr Cys
                 85                  90                  95

Ala Lys Gly Arg Asp Ala Phe Asp Ile Trp Gly Gln Gly Thr Leu Val
            100                 105                 110

Thr Val Ser Ser
        115
```

```
<210> SEQ ID NO 164
<211> LENGTH: 24
<212> TYPE: DNA
<213> ORGANISM: Artificial Sequence
<220> FEATURE:
<223> OTHER INFORMATION: Synthetic

<400> SEQUENCE: 164
ggattcacct ttgatgatta tgcc                                             24
```

```
<210> SEQ ID NO 165
<211> LENGTH: 8
<212> TYPE: PRT
<213> ORGANISM: Artificial Sequence
<220> FEATURE:
<223> OTHER INFORMATION: Synthetic

<400> SEQUENCE: 165

Gly Phe Thr Phe Asp Asp Tyr Ala
 1               5
```

```
<210> SEQ ID NO 166
<211> LENGTH: 24
<212> TYPE: DNA
<213> ORGANISM: Artificial Sequence
<220> FEATURE:
<223> OTHER INFORMATION: Synthetic
```

<400> SEQUENCE: 166
attagttgga acagtggtag aata                                                24

<210> SEQ ID NO 167
<211> LENGTH: 8
<212> TYPE: PRT
<213> ORGANISM: Artificial Sequence
<220> FEATURE:
<223> OTHER INFORMATION: Synthetic

<400> SEQUENCE: 167

Ile Ser Trp Asn Ser Gly Arg Ile
1               5

<210> SEQ ID NO 168
<211> LENGTH: 27
<212> TYPE: DNA
<213> ORGANISM: Artificial Sequence
<220> FEATURE:
<223> OTHER INFORMATION: Synthetic

<400> SEQUENCE: 168
gcaaaaggcc gggatgcttt tgatatc                                             27

<210> SEQ ID NO 169
<211> LENGTH: 9
<212> TYPE: PRT
<213> ORGANISM: Artificial Sequence
<220> FEATURE:
<223> OTHER INFORMATION: Synthetic

<400> SEQUENCE: 169

Ala Lys Gly Arg Asp Ala Phe Asp Ile
1               5

<210> SEQ ID NO 170
<211> LENGTH: 322
<212> TYPE: DNA
<213> ORGANISM: Artificial Sequence
<220> FEATURE:
<223> OTHER INFORMATION: Synthetic

<400> SEQUENCE: 170
gacatccaga tgacccagtc tccatcttcc gtgtctgcat ctgtaggaga cagagtcacc         60
atcacttgtc gggcgagtca gggtattagc agctggttag cctggtatca gcagaaacca        120
gggaaagccc ctaagctcct gatctatgct gcatccagtt tgcaaagtgg ggtcccatca        180
aggttcagcg gcagtggatc tgggacagat ttcactctca ccatcagcag cctgcagcct        240
gaagattttg caacttacta ttgtcaacag gctaacagtt tcccgtacac ttttggccag        300
gggaccaagc tggagatcaa ac                                                 322

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
          35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Thr Phe Gly Gln Gly Thr Lys Leu Glu Ile Lys
             100                 105

<210> SEQ ID NO 172
<211> LENGTH: 18
<212> TYPE: DNA
<213> ORGANISM: Artificial Sequence
<220> FEATURE:
<223> OTHER INFORMATION: Synthetic

<400> SEQUENCE: 172
cagggtatta gcagctgg                                                 18

<210> SEQ ID NO 173
<211> LENGTH: 6
<212> TYPE: PRT
<213> ORGANISM: Artificial Sequence
<220> FEATURE:
<223> OTHER INFORMATION: Synthetic

<400> SEQUENCE: 173

Gln Gly Ile Ser Ser Trp
 1               5

<210> SEQ ID NO 174
<211> LENGTH: 9
<212> TYPE: DNA
<213> ORGANISM: Artificial Sequence
<220> FEATURE:
<223> OTHER INFORMATION: Synthetic

<400> SEQUENCE: 174 gctgcatcc                                                            9

<210> SEQ ID NO 175
<211> LENGTH: 3
<212> TYPE: PRT
<213> ORGANISM: Artificial Sequence
<220> FEATURE:
<223> OTHER INFORMATION: Synthetic

<400> SEQUENCE: 175

Ala Ala Ser
 1

<210> SEQ ID NO 176
<211> LENGTH: 27
<212> TYPE: DNA
<213> ORGANISM: Artificial Sequence
<220> FEATURE:
<223> OTHER INFORMATION: Synthetic

<400> SEQUENCE: 176
caacaggcta acagtttccc gtacact                                       27

<210> SEQ ID NO 177

```
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gln Gln Ala Asn Ser Phe Pro Tyr Thr
 1               5

<210> SEQ ID NO 178
<211> LENGTH: 361
<212> TYPE: DNA
<213> ORGANISM: Artificial Sequence
<220> FEATURE:
<223> OTHER INFORMATION: Synthetic

<400> SEQUENCE: 178
caggtgcagc tggtgcagtc tggggctgag gtgaaagagc ctggggcctc agtgaaggtc      60
tcctgcaagg cttctggata caccttcacc tcttatgata tcatctgggt gcgacaggcc     120
actggacaag gcttgagtg gatgggatgg atgaacccaa acagtggtaa cacaggctat      180
acacagaacc tccagggcag agtcaccttg accaggaaca cctccataac tacagtctac     240
atggaactga gcagcctgag ctctgaggac acggccgttt attactgtgc gcgagactac     300
agtagccact actacggttt ggacgtctgg ggccaaggga ccacggtcac cgtctcctca     360
a                                                                     361

<210> SEQ ID NO 179
<211> LENGTH: 120
<212> TYPE: PRT
<213> ORGANISM: Artificial Sequence
<220> FEATURE:
<223> OTHER INFORMATION: Synthetic

<400> SEQUENCE: 179

Gln Val Gln Leu Val Gln Ser Gly Ala Glu Val Lys Glu Pro Gly Ala
 1               5                  10                  15

Ser Val Lys Val Ser Cys Lys Ala Ser Gly Tyr Thr Phe Thr Ser Tyr
                20                  25                  30

Asp Ile Ile Trp Val Arg Gln Ala Thr Gly Gln Gly Leu Glu Trp Met
            35                  40                  45

Gly Trp Met Asn Pro Asn Ser Gly Asn Thr Gly Tyr Thr Gln Asn Leu
        50                  55                  60

Gln Gly Arg Val Thr Leu Thr Arg Asn Thr Ser Ile Thr Thr Val Tyr
 65                 70                  75                  80

Met Glu Leu Ser Ser Leu Ser Ser Glu Asp Thr Ala Val Tyr Tyr Cys
                85                  90                  95

Ala Arg Asp Tyr Ser Ser His Tyr Tyr Gly Leu Asp Val Trp Gly Gln
                100                 105                 110

Gly Thr Thr Val Thr Val Ser Ser
            115                 120

<210> SEQ ID NO 180
<211> LENGTH: 24
<212> TYPE: DNA
<213> ORGANISM: Artificial Sequence
<220> FEATURE:
<223> OTHER INFORMATION: Synthetic

<400> SEQUENCE: 180
ggatacacct tcacctctta tgat                                             24
```

<210> SEQ ID NO 181
<211> LENGTH: 8
<212> TYPE: PRT
<213> ORGANISM: Artificial Sequence
<220> FEATURE:
<223> OTHER INFORMATION: Synthetic

<400> SEQUENCE: 181

Gly Tyr Thr Phe Thr Ser Tyr Asp
 1               5

<210> SEQ ID NO 182
<211> LENGTH: 24
<212> TYPE: DNA
<213> ORGANISM: Artificial Sequence
<220> FEATURE:
<223> OTHER INFORMATION: Synthetic

<400> SEQUENCE: 182
atgaacccaa acagtggtaa caca                                              24

<210> SEQ ID NO 183
<211> LENGTH: 8
<212> TYPE: PRT
<213> ORGANISM: Artificial Sequence
<220> FEATURE:
<223> OTHER INFORMATION: Synthetic

<400> SEQUENCE: 183

Met Asn Pro Asn Ser Gly Asn Thr
 1               5

<210> SEQ ID NO 184
<211> LENGTH: 39
<212> TYPE: DNA
<213> ORGANISM: Artificial Sequence
<220> FEATURE:
<223> OTHER INFORMATION: Synthetic

<400> SEQUENCE: 184
gcgcgagact acagtagcca ctactacggt ttggacgtc                              39

<210> SEQ ID NO 185
<211> LENGTH: 13
<212> TYPE: PRT
<213> ORGANISM: Artificial Sequence
<220> FEATURE:
<223> OTHER INFORMATION: Synthetic

<400> SEQUENCE: 185

Ala Arg Asp Tyr Ser Ser His Tyr Tyr Gly Leu Asp Val
 1               5                   10

<210> SEQ ID NO 186
<211> LENGTH: 322
<212> TYPE: DNA
<213> ORGANISM: Artificial Sequence
<220> FEATURE:
<223> OTHER INFORMATION: Synthetic

<400> SEQUENCE: 186
gacatccagt tgacccagtc tccatccttc ctgtctacat ctataggaga cagagtcacc       60
atcacttgct gggccagtca ggacattagc aattatttag cctggtatca gcaaaaacca      120
gggaaagccc ctaagctcct gatctttgtt gcatccactt tgcagagtgg ggtcccatca      180

```
aggttcagcg gcagtggatc tgggacagaa ttcactctca caatcagtag cctgcagcct    240
gaggattttg caacttatta ctgtcaacag tttaatagtt acccgctcac tttcggcgga    300
gggaccaagg tggaaatcaa ac                                             322
```

<210> SEQ ID NO 187
<211> LENGTH: 107
<212> TYPE: PRT
<213> ORGANISM: Artificial Sequence
<220> FEATURE:
<223> OTHER INFORMATION: Synthetic

<400> SEQUENCE: 187

```
Asp Ile Gln Leu Thr Gln Ser Pro Ser Phe Leu Ser Thr Ser Ile Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Phe Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 188
<211> LENGTH: 18
<212> TYPE: DNA
<213> ORGANISM: Artificial Sequence
<220> FEATURE:
<223> OTHER INFORMATION: Synthetic

<400> SEQUENCE: 188

```
caggacatta gcaattat                                                   18
```

<210> SEQ ID NO 189
<211> LENGTH: 6
<212> TYPE: PRT
<213> ORGANISM: Artificial Sequence
<220> FEATURE:
<223> OTHER INFORMATION: Synthetic

<400> SEQUENCE: 189

```
Gln Asp Ile Ser Asn Tyr
1               5
```

<210> SEQ ID NO 190
<211> LENGTH: 9
<212> TYPE: DNA
<213> ORGANISM: Artificial Sequence
<220> FEATURE:
<223> OTHER INFORMATION: Synthetic

<400> SEQUENCE: 190

```
gttgcatcc                                                              9
```

<210> SEQ ID NO 191
<211> LENGTH: 3
<212> TYPE: PRT
<213> ORGANISM: Artificial Sequence
<220> FEATURE:

<223> OTHER INFORMATION: Synthetic

<400> SEQUENCE: 191

Val Ala Ser
 1

<210> SEQ ID NO 192
<211> LENGTH: 30
<212> TYPE: DNA
<213> ORGANISM: Artificial Sequence
<220> FEATURE:
<223> OTHER INFORMATION: Synthetic

<400> SEQUENCE: 192
caacagttta atagttaccc gctcactttc         30

<210> SEQ ID NO 193
<211> LENGTH: 10
<212> TYPE: PRT
<213> ORGANISM: Artificial Sequence
<220> FEATURE:
<223> OTHER INFORMATION: Synthetic

<400> SEQUENCE: 193

Gln Gln Phe Asn Ser Tyr Pro Leu Thr Phe
 1               5                  10

<210> SEQ ID NO 194
<211> LENGTH: 378
<212> TYPE: DNA
<213> ORGANISM: Artificial Sequence
<220> FEATURE:
<223> OTHER INFORMATION: Synthetic

<400> SEQUENCE: 194
caggtccagc tggtgcagtc tgggggagac ttggtacagc ccggcaggtc cctgagactc         60
tcctgtgcag cctctggatt cacctttgat gattatgcca tgcactgggt ccggcaaact        120
ccagggaagg gcctggagtg gtctcaggt attagttgga atagtggggc ataggctat          180 gcggactctg tgaagggccg attcaccatc tccagagaca cgccaagaa ctccctgtat         240 ctgcaaatga acagtctgag agctgaggac acggccttgt attactgtac aaaagaagaa        300
gtgggagcta cggtggatta tttctacttc tacggtatgg acgtctgggg ccaagggacc        360
acggtcaccg tctcctca                                                     378

<210> SEQ ID NO 195
<211> LENGTH: 126
<212> TYPE: PRT
<213> ORGANISM: Artificial Sequence
<220> FEATURE:
<223> OTHER INFORMATION: Synthetic

<400> SEQUENCE: 195

Gln Val Gln Leu Val Gln Ser Gly Gly Asp Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Thr Pro Gly Lys Gly Leu Glu Trp Val
         35                  40                  45

Ser Gly Ile Ser Trp Asn Ser Gly Ala Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                    85                  90                  95

Thr Lys Glu Glu Val Gly Ala Thr Val Asp Tyr Phe Tyr Phe Tyr Gly
                100                 105                 110

Met Asp Val Trp Gly Gln Gly Thr Thr Val Thr Val Ser Ser
            115                 120                 125

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
ggattcacct ttgatgatta tgcc                                          24

<210> SEQ ID NO 197
<211> LENGTH: 8
<212> TYPE: PRT
<213> ORGANISM: Artificial Sequence
<220> FEATURE:
<223> OTHER INFORMATION: Synthetic

<400> SEQUENCE: 197

Gly Phe Thr Phe Asp Asp Tyr Ala
1               5

<210> SEQ ID NO 198
<211> LENGTH: 24
<212> TYPE: DNA
<213> ORGANISM: Artificial Sequence
<220> FEATURE:
<223> OTHER INFORMATION: Synthetic

<400> SEQUENCE: 198
attagttgga atagtggggc cata                                          24

<210> SEQ ID NO 199
<211> LENGTH: 8
<212> TYPE: PRT
<213> ORGANISM: Artificial Sequence
<220> FEATURE:
<223> OTHER INFORMATION: Synthetic

<400> SEQUENCE: 199

Ile Ser Trp Asn Ser Gly Ala Ile
1               5

<210> SEQ ID NO 200
<211> LENGTH: 57
<212> TYPE: DNA
<213> ORGANISM: Artificial Sequence
<220> FEATURE:
<223> OTHER INFORMATION: Synthetic

<400> SEQUENCE: 200
acaaaagaag aagtgggagc tacggtggat tatttctact tctacggtat ggacgtc      57

<210> SEQ ID NO 201
<211> LENGTH: 19
<212> TYPE: PRT
<213> ORGANISM: Artificial Sequence
<220> FEATURE:
<223> OTHER INFORMATION: Synthetic

<400> SEQUENCE: 201

Thr Lys Glu Glu Val Gly Ala Thr Val Asp Tyr Phe Tyr Phe Tyr Gly
 1               5                   10                  15

Met Asp Val

<210> SEQ ID NO 202
<211> LENGTH: 318
<212> TYPE: DNA
<213> ORGANISM: Artificial Sequence
<220> FEATURE:
<223> OTHER INFORMATION: Synthetic

<400> SEQUENCE: 202
gaaattgtga tgactcagtc tccagccacc ctgtctttgt ctccagggga aagagccacc    60
ctctcctgct gggccagtca gagtgttagc aactacttag cctggtacca acagaaacct   120
ggccaggctc ccagactcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctacgtt cggccaaggg   300
accaaggtgg aaatcaaa                                                 318

<210> SEQ ID NO 203
<211> LENGTH: 106
<212> TYPE: PRT
<213> ORGANISM: Artificial Sequence
<220> FEATURE:
<223> OTHER INFORMATION: Synthetic

<400> SEQUENCE: 203

Glu Ile Val Met Thr Gln Ser Pro Ala Thr Leu Ser Leu Ser Pro Gly
 1               5                   10                  15

Glu Arg Ala Thr Leu Ser Cys Trp Ala Ser Gln Ser Val Ser Asn Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 204
<211> LENGTH: 18
<212> TYPE: DNA
<213> ORGANISM: Artificial Sequence
<220> FEATURE:
<223> OTHER INFORMATION: Synthetic

<400> SEQUENCE: 204
cagagtgtta gcaactac                                                  18

<210> SEQ ID NO 205
<211> LENGTH: 6
<212> TYPE: PRT
<213> ORGANISM: Artificial Sequence
<220> FEATURE:
<223> OTHER INFORMATION: Synthetic -continued

<400> SEQUENCE: 205

Gln Ser Val Ser Asn Tyr
 1               5

<210> SEQ ID NO 206
<211> LENGTH: 9
<212> TYPE: DNA
<213> ORGANISM: Artificial Sequence
<220> FEATURE:
<223> OTHER INFORMATION: Synthetic

<400> SEQUENCE: 206 gatgcatcc                                                                 9

<210> SEQ ID NO 207
<211> LENGTH: 3
<212> TYPE: PRT
<213> ORGANISM: Artificial Sequence
<220> FEATURE:
<223> OTHER INFORMATION: Synthetic

<400> SEQUENCE: 207

Asp Ala Ser
 1

<210> SEQ ID NO 208
<211> LENGTH: 24
<212> TYPE: DNA
<213> ORGANISM: Artificial Sequence
<220> FEATURE:
<223> OTHER INFORMATION: Synthetic

<400> SEQUENCE: 208
cagcagcgta gcaactggcc tacg                                               24

<210> SEQ ID NO 209
<211> LENGTH: 8
<212> TYPE: PRT
<213> ORGANISM: Artificial Sequence
<220> FEATURE:
<223> OTHER INFORMATION: Synthetic

<400> SEQUENCE: 209

Gln Gln Arg Ser Asn Trp Pro Thr
 1               5

<210> SEQ ID NO 210
<211> LENGTH: 348
<212> TYPE: DNA
<213> ORGANISM: Artificial Sequence
<220> FEATURE:
<223> OTHER INFORMATION: Synthetic

<400> SEQUENCE: 210
caagtgcagc tggtgcagtc tgggggaggc ttggtacagc ctggcaggtc cctgagactc        60
tcctgtgcag cctctggatt cacctttgat gattatgcca tgcactgggt ccggcaagct       120
ccagggaagg gcctggagtg ggtctcaggt attagttgga atagtggtag ggtaggctat       180
gcggactctg tgaagggccg attcaccatc tccagagaca acgccaagaa ctccctgtat       240
ctgcaaatga acagtctgag agctgaggac acggccttgt attactgtac aaaaggccgg       300
gatgcttttg atatctgggg ccaggggaca atggtcaccg tctcttca                   348

<210> SEQ ID NO 211
<211> LENGTH: 116

```
<212> TYPE: PRT
<213> ORGANISM: Artificial Sequence
<220> FEATURE:
<223> OTHER INFORMATION: Synthetic

<400> SEQUENCE: 211

Gln Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Gly Arg Asp Ala Phe Asp Ile Trp Gly Gln Gly Thr Met Val
            100                 105                 110

Thr Val Ser Ser
        115

<210> SEQ ID NO 212
<211> LENGTH: 24
<212> TYPE: DNA
<213> ORGANISM: Artificial Sequence
<220> FEATURE:
<223> OTHER INFORMATION: Synthetic

<400> SEQUENCE: 212
ggattcacct ttgatgatta tgcc                                          24

<210> SEQ ID NO 213
<211> LENGTH: 8
<212> TYPE: PRT
<213> ORGANISM: Artificial Sequence
<220> FEATURE:
<223> OTHER INFORMATION: Synthetic

<400> SEQUENCE: 213

Gly Phe Thr Phe Asp Asp Tyr Ala
 1               5

<210> SEQ ID NO 214
<211> LENGTH: 24
<212> TYPE: DNA
<213> ORGANISM: Artificial Sequence
<220> FEATURE:
<223> OTHER INFORMATION: Synthetic

<400> SEQUENCE: 214
attagttgga atagtggtag ggta                                          24

<210> SEQ ID NO 215
<211> LENGTH: 8
<212> TYPE: PRT
<213> ORGANISM: Artificial Sequence
<220> FEATURE:
<223> OTHER INFORMATION: Synthetic

<400> SEQUENCE: 215

Ile Ser Trp Asn Ser Gly Arg Val
 1               5
```

<210> SEQ ID NO 216
<211> LENGTH: 27
<212> TYPE: DNA
<213> ORGANISM: Artificial Sequence
<220> FEATURE:
<223> OTHER INFORMATION: Synthetic

<400> SEQUENCE: 216
acaaaaggcc gggatgcttt tgatatc                                               27

<210> SEQ ID NO 217
<211> LENGTH: 9
<212> TYPE: PRT
<213> ORGANISM: Artificial Sequence
<220> FEATURE:
<223> OTHER INFORMATION: Synthetic

<400> SEQUENCE: 217

Thr Lys Gly Arg Asp Ala Phe Asp Ile
 1               5

<210> SEQ ID NO 218
<211> LENGTH: 321
<212> TYPE: DNA
<213> ORGANISM: Artificial Sequence
<220> FEATURE:
<223> OTHER INFORMATION: Synthetic

<400> SEQUENCE: 218
gatattgtga tgacccagtc tccatcttcc gtgtctgcat ctgtaggaga cagagtcacc           60
atcacttgtc gggcgagtca gggtattagc agctggttag cctggtatca gcagaaacca          120
gggaaagccc ctaagctcct gatctatgct gcatccagtt tgcaaagtgg ggtcccatca          180
aggttcagcg gcagtggatc tgggacagat tcactctca ccatcagcag cctgcagcct           240
gaagattttg caacttacta ttgtcaacag gctaacagtt tcccgtacac ttttggccag          300
gggaccaagc tggagatcaa a                                                   321

<210> SEQ ID NO 219
<211> LENGTH: 107
<212> TYPE: PRT
<213> ORGANISM: Artificial Sequence
<220> FEATURE:
<223> OTHER INFORMATION: Synthetic

<400> SEQUENCE: 219

Asp Ile Val Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

```
<210> SEQ ID NO 220
<211> LENGTH: 18
<212> TYPE: DNA
<213> ORGANISM: Artificial Sequence
<220> FEATURE:
<223> OTHER INFORMATION: Synthetic

<400> SEQUENCE: 220
cagggtatta gcagctgg                                                 18

<210> SEQ ID NO 221
<211> LENGTH: 6
<212> TYPE: PRT
<213> ORGANISM: Artificial Sequence
<220> FEATURE:
<223> OTHER INFORMATION: Synthetic

<400> SEQUENCE: 221

Gln Gly Ile Ser Ser Trp
 1               5

<210> SEQ ID NO 222
<211> LENGTH: 9
<212> TYPE: DNA
<213> ORGANISM: Artificial Sequence
<220> FEATURE:
<223> OTHER INFORMATION: Synthetic

<400> SEQUENCE: 222 gctgcatcc                                                            9

<210> SEQ ID NO 223
<211> LENGTH: 3
<212> TYPE: PRT
<213> ORGANISM: Artificial Sequence
<220> FEATURE:
<223> OTHER INFORMATION: Synthetic

<400> SEQUENCE: 223

Ala Ala Ser
 1

<210> SEQ ID NO 224
<211> LENGTH: 27
<212> TYPE: DNA
<213> ORGANISM: Artificial Sequence
<220> FEATURE:
<223> OTHER INFORMATION: Synthetic

<400> SEQUENCE: 224
caacaggcta acagtttccc gtacact                                       27

<210> SEQ ID NO 225
<211> LENGTH: 9
<212> TYPE: PRT
<213> ORGANISM: Artificial Sequence
<220> FEATURE:
<223> OTHER INFORMATION: Synthetic

<400> SEQUENCE: 225

Gln Gln Ala Asn Ser Phe Pro Tyr Thr
 1               5

<210> SEQ ID NO 226
<211> LENGTH: 378
<212> TYPE: DNA
<213> ORGANISM: Artificial Sequence
<220> FEATURE:
```

<223> OTHER INFORMATION: Synthetic

<400> SEQUENCE: 226

```
gaagtgcagc tggtggaatc tggaggagga ctggtgcagc ctggaagatc tctgagactg    60
tcttgtgctg cttctggatt tatctttgat gattatgcta tgcattgggt gagacaggct   120
cctggaaagg gactggaatg ggtgtctgga atctcttgga attctggatc tatcggatat   180
gctgattctg tgaagggaag atttacaatc tctagagata tgctaagaa ttctctgtat   240
ctgcagatga attctctgag agctgaagat acagctctgt attattgtgc taaggatgga   300
ggatcttctt ggctgccttt tgtgtattat tatggaatgg atgtgtgggg acagggaaca   360
acagtgacag tgtcttct                                                 378
```

<210> SEQ ID NO 227
<211> LENGTH: 126
<212> TYPE: PRT
<213> ORGANISM: Artificial Sequence
<220> FEATURE:
<223> OTHER INFORMATION: Synthetic

<400> SEQUENCE: 227

Glu Val Gln Leu Val Glu Ser Gly Gly Gly Leu Val Gln Pro Gly Arg
 1               5                  10                  15
Ser Leu Arg Leu Ser Cys Ala Ala Ser Gly Phe Ile Phe Asp Asp Tyr
            20                  25                  30
Ala Met His Trp Val Arg Gln Ala Pro Gly Lys Gly Leu Glu Trp Val
        35                  40                  45
Ser Gly Ile Ser Trp Asn Ser Gly Ser Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Asp Gly Gly Ser Ser Trp Leu Pro Phe Val Tyr Tyr Tyr Gly
            100                 105                 110
Met Asp Val Trp Gly Gln Gly Thr Thr Val Thr Val Ser Ser
        115                 120                 125

<210> SEQ ID NO 228
<211> LENGTH: 324
<212> TYPE: DNA
<213> ORGANISM: Artificial Sequence
<220> FEATURE:
<223> OTHER INFORMATION: Synthetic

<400> SEQUENCE: 228

```
gaaatcgtga tgacacagtc tcctgctaca ctgtctgtgt ctcctggaga aagagctaca    60
ctgtcttgta gcttctca gtctatctct ctaatctgg cttggtatca gcagaagcct     120
ggacaggctc ctagactgct gatctatgga gcttctacaa gagctacagg aatccctgct   180
agattttctg gatctggatc tggaacagaa tttacactga caatctcttc tctgcagtct   240
gaagattttg ctgtgtatta ttgtcagcag tattcttctt ggcctcctta tacatttgga   300
cagggaacaa agctggaaat caag                                          324
```

<210> SEQ ID NO 229
<211> LENGTH: 108
<212> TYPE: PRT
<213> ORGANISM: Artificial Sequence
<220> FEATURE:

<223> OTHER INFORMATION: Synthetic

<400> SEQUENCE: 229

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105
```

<210> SEQ ID NO 230
<211> LENGTH: 348
<212> TYPE: DNA
<213> ORGANISM: Artificial Sequence
<220> FEATURE:
<223> OTHER INFORMATION: Synthetic

<400> SEQUENCE: 230

```
gaggtccagc tggtcgagtc aggaggaggc ctcgtccaac cagggcgcag ccttcgactc    60
tcctgtgccg ccagtaggtt tactttcgat gactatgcca tgcactgggt ccggcaggcc   120
cctggtaagg gcttggagtg ggtgtccggt atctcctgga actccggacg tatcggttac   180
gccgacagcg tgaagggaag gttcactatc tctcgtgaca cgccaagaa ctccttgtat    240
ctgcaaatga acagcctccg ggccgaagac accgccttgt attactgtgc caagggtagg   300
gatagtttcg atatctgggg tcaaggcacc atggtgactg tgtcttca               348
```

<210> SEQ ID NO 231
<211> LENGTH: 116
<212> TYPE: PRT
<213> ORGANISM: Artificial Sequence
<220> FEATURE:
<223> OTHER INFORMATION: Synthetic

<400> SEQUENCE: 231

```
Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
            115
```

<210> SEQ ID NO 232
<211> LENGTH: 321
<212> TYPE: DNA
<213> ORGANISM: Artificial Sequence
<220> FEATURE:
<223> OTHER INFORMATION: Synthetic

<400> SEQUENCE: 232

```
gacatacaga tgacccaaag cccaagcagc gttagcgctt ccgtaggcga cagggtgaca      60
attacatgca gagcctctca gggaatttct tcatggctgg catggtatca gcagaagccc     120
ggaaaagctc ccaagctgct gatatatggt gcctcctctc tccaaagcgg agtcccatca     180
cgcttctccg ggagtggctc tggtacagat tttactttga caatctctag ccttcagcct     240
gaagactttg ctacatacta ctgtcagcag gccaacagtt ttccttacac cttcggtcag     300
ggaactaaac tggaaattaa g                                                321
```

<210> SEQ ID NO 233
<211> LENGTH: 107
<212> TYPE: PRT
<213> ORGANISM: Artificial Sequence
<220> FEATURE:
<223> OTHER INFORMATION: Synthetic

<400> SEQUENCE: 233

```
Asp Ile Gln Met Thr Gln Ser Pro Ser Ser Val Ser Ala Ser Val Gly
  1               5                  10                  15
Asp Arg Val Thr Ile Thr Cys Arg Ala Ser Gln Gly Ile Ser Ser Trp
             20                  25                  30
Leu Ala Trp Tyr Gln Gln Lys Pro Gly Lys Ala Pro Lys Leu Leu Ile
         35                  40                  45
Tyr Gly Ala Ser Ser Leu Glu Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Phe Pro Tyr
                 85                  90                  95
Thr Phe Gly Gln Gly Thr Lys Leu Glu Ile Lys
            100                 105
```

<210> SEQ ID NO 234
<211> LENGTH: 360
<212> TYPE: DNA
<213> ORGANISM: Artificial Sequence
<220> FEATURE:
<223> OTHER INFORMATION: Synthetic

<400> SEQUENCE: 234

```
caggtgcagc tggtgcagtc tggagctgaa gtgaagaagc ctggagcttc tgtgaaggtg      60
tcttgtaagg cttctggata cacatttaca tcttatgata tcatctgggt gagacaggct     120
acaggacagg gactggaatg gatgggatgg atgaatccta attctggaaa tacaggatat     180
gctcagaagt ttcagggaag agtgacaatg acaagaaata tcctctatct tacagtgtat     240
atggaactgt cttctctgag atctgaagat acagctgtgt attattgtgc tagagattat     300
tcttctcatt attatggact ggatgtgtgg ggacagggaa caacagtgac agtgtcttct     360
```

<210> SEQ ID NO 235
<211> LENGTH: 120
<212> TYPE: PRT

<213> ORGANISM: Artificial Sequence
<220> FEATURE:
<223> OTHER INFORMATION: Synthetic

<400> SEQUENCE: 235

```
Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
            20                  25                  30
Asp Ile Ile Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Tyr Ser Ser His Tyr Tyr Gly Leu Asp Val Trp Gly Gln
            100                 105                 110
Gly Thr Thr Val Thr Val Ser Ser
        115                 120
```

<210> SEQ ID NO 236
<211> LENGTH: 321
<212> TYPE: DNA
<213> ORGANISM: Artificial Sequence
<220> FEATURE:
<223> OTHER INFORMATION: Synthetic

<400> SEQUENCE: 236

```
gatatccagc tgacacagtc tccttctttt ctgtctgctt ctgtgggaga tagagtgaca     60
atcacatgta gcttctca ggatatctct aattatctgg cttggtatca gcagaagcct    120
ggaaaggctc ctaagctgct gatctatgtg gcttctacac tgcagtctgg agtgccttct   180
agattttctg gatctggatc tggaacagaa tttacactga caatctcttc tctgcagcct   240
gaagattttg ctacatatta ttgtcagcag tttaattctt atcctctgac atttggagga   300
ggaacaaagg tggaaatcaa g                                              321
```

<210> SEQ ID NO 237
<211> LENGTH: 107
<212> TYPE: PRT
<213> ORGANISM: Artificial Sequence
<220> FEATURE:
<223> OTHER INFORMATION: Synthetic

<400> SEQUENCE: 237

```
Asp Ile Gln Leu Thr Gln Ser Pro Ser Phe Leu Ser Ala Ser Val Gly
 1               5                  10                  15
Asp Arg Val Thr Ile Thr Cys Arg Ala Ser Gln Asp Ile Ser Asn Tyr
            20                  25                  30
Leu Ala Trp Tyr Gln Gln Lys Pro Gly Lys Ala Pro Lys Leu Leu Ile
        35                  40                  45
Tyr Val Ala Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Leu
                85                  90                  95
```

Thr Phe Gly Gly Gly Thr Lys Val Glu Ile Lys
            100                 105

<210> SEQ ID NO 238
<211> LENGTH: 349
<212> TYPE: DNA
<213> ORGANISM: Artificial Sequence
<220> FEATURE:
<223> OTHER INFORMATION: Synthetic

<400> SEQUENCE: 238
gaagtgcagc tggtggagtc tgggggaggc ttggtacagc ctggcaggtc cctgagactc      60
tcctgtgcag cctctggatt cacctttgat gattatgccc tgcactgggt ccggcaagct     120
ccagggaagg gcctggagtg ggtctcaggt gttagttgga atggtggtag aataggctat     180
gcggactctg tgaaaggccg attcaccatc tccagagaca cgccaagaa ctccctcttt      240 ctgcaaatga acagtctgag agttgaggac acggccttgt attattgtgc aaaaggccgg     300
gatgcttttg atatctgggg ccaagggaca ttggtcaccg tctcttcag                 349

<210> SEQ ID NO 239
<211> LENGTH: 116
<212> TYPE: PRT
<213> ORGANISM: Artificial Sequence
<220> FEATURE:
<223> OTHER INFORMATION: Synthetic

<400> SEQUENCE: 239

Glu Val Gln Leu Val Glu Ser Gly Gly Gly Leu Val Gln Pro Gly Arg
  1               5                   10                  15

Ser Leu Arg Leu Ser Cys Ala Ala Ser Gly Phe Thr Phe Asp Asp Tyr
             20                  25                  30

Ala Leu His Trp Val Arg Gln Ala Pro Gly Lys Gly Leu Glu Trp Val
         35                  40                  45

Ser Gly Val Ser Trp Asn Gly Gly Arg Ile Gly Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Val Glu Asp Thr Ala Leu Tyr Tyr Cys
                 85                  90                  95

Ala Lys Gly Arg Asp Ala Phe Asp Ile Trp Gly Gln Gly Thr Met Val
            100                 105                 110

Thr Val Ser Ser
        115

<210> SEQ ID NO 240
<211> LENGTH: 348
<212> TYPE: DNA
<213> ORGANISM: Artificial Sequence
<220> FEATURE:
<223> OTHER INFORMATION: Synthetic

<400> SEQUENCE: 240
gaagtgcagc tggtggaatc tgaggaggga ctggtgcagc tggaagatc tctgagactg       60 tcttgtgctg cttctggatt tacatttgat gattatgcta tgcattgggt gagacaggct     120
cctggaaagg gactggaatg ggtgtctgga gtgtcttgga tggaggaag aatcggatat      180 gctgattctg tgaagggaag atttacaatc tctagagata tgctaagaa ttctctgtat      240 ctgcagatga attctctgag agctgaagat acagctctgt attattgtgc taagggaaga    300
gatgcttttg atatctgggg acagggaaca atggtgacag tgtcttct                 348

<210> SEQ ID NO 241
<211> LENGTH: 116
<212> TYPE: PRT
<213> ORGANISM: Artificial Sequence
<220> FEATURE:
<223> OTHER INFORMATION: Synthetic

<400> SEQUENCE: 241

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Val Ser Trp Asn Gly Arg Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Asp Ala Phe Asp Ile Trp Gly Gln Gly Thr Met Val
            100                 105                 110

Thr Val Ser Ser
            115
```

<210> SEQ ID NO 242
<211> LENGTH: 330
<212> TYPE: PRT
<213> ORGANISM: Artificial Sequence
<220> FEATURE:
<223> OTHER INFORMATION: Synthetic

<400> SEQUENCE: 242

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 243
<211> LENGTH: 327
<212> TYPE: PRT
<213> ORGANISM: Artificial Sequence
<220> FEATURE:
<223> OTHER INFORMATION: Synthetic

<400> SEQUENCE: 243

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 244
<211> LENGTH: 327
<212> TYPE: PRT
<213> ORGANISM: Artificial Sequence
<220> FEATURE:
<223> OTHER INFORMATION: Synthetic

<400> SEQUENCE: 244

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
```

```
                    260                 265                 270
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 245
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly or Arg
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Asp
<220> FEATURE:
<221> NAME/KEY: VARIANT
<222> LOCATION: (6)...(6)
<223> OTHER INFORMATION: Xaa = Asp
<220> FEATURE:
<221> NAME/KEY: VARIANT
<222> LOCATION: (7)...(7)
<223> OTHER INFORMATION: Xaa = Tyr
<220> FEATURE:
<221> NAME/KEY: VARIANT
<222> LOCATION: (8)...(8)
<223> OTHER INFORMATION: Xaa = Ala

<400> SEQUENCE: 245

Xaa Xaa Xaa Xaa Xaa Xaa Xaa Xaa
 1               5

<210> SEQ ID NO 246
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile or Val
<220> FEATURE:
<221> NAME/KEY: VARIANT
<222> LOCATION: (2)...(2)
<223> OTHER INFORMATION: Xaa = Ser
<220> FEATURE:
<221> NAME/KEY: VARIANT
<222> LOCATION: (3)...(3)
<223> OTHER INFORMATION: Xaa = Trp
<220> FEATURE:
<221> NAME/KEY: VARIANT
```

-continued

```
<222> LOCATION: (4)...(4)
<223> OTHER INFORMATION: Xaa = Asn
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Gly
<220> FEATURE:
<221> NAME/KEY: VARIANT
<222> LOCATION: (7)...(7)
<223> OTHER INFORMATION: Xaa = Ser
<220> FEATURE:
<221> NAME/KEY: VARIANT
<222> LOCATION: (8)...(8)
<223> OTHER INFORMATION: Xaa = Ile

<400> SEQUENCE: 246

Xaa Xaa Xaa Xaa Xaa Xaa Xaa Xaa
 1               5

<210> SEQ ID NO 247
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Lys
<220> FEATURE:
<221> NAME/KEY: VARIANT
<222> LOCATION: (3)...(3)
<223> OTHER INFORMATION: Xaa = Gly
<220> FEATURE:
<221> NAME/KEY: VARIANT
<222> LOCATION: (4)...(4)
<223> OTHER INFORMATION: Xaa = Arg
<220> FEATURE:
<221> NAME/KEY: VARIANT
<222> LOCATION: (5)...(5)
<223> OTHER INFORMATION: Xaa = Asp
<220> FEATURE:
<221> NAME/KEY: VARIANT
<222> LOCATION: (6)...(6)
<223> OTHER INFORMATION: Xaa = Ser or Ala
<220> FEATURE:
<221> NAME/KEY: VARIANT
<222> LOCATION: (7)...(7)
<223> OTHER INFORMATION: Xaa = Phe
<220> FEATURE:
<221> NAME/KEY: VARIANT
<222> LOCATION: (8)...(8)
<223> OTHER INFORMATION: Xaa = Asp
<220> FEATURE:
<221> NAME/KEY: VARIANT
<222> LOCATION: (9)...(9)
<223> OTHER INFORMATION: Xaa = Ile
<220> FEATURE:
<221> NAME/KEY: VARIANT
<222> LOCATION: (10)...(10)
<223> OTHER INFORMATION: Xaa = Pro or absent
<220> FEATURE:
<221> NAME/KEY: VARIANT
<222> LOCATION: (11)...(11)
<223> OTHER INFORMATION: Xaa = Phe or absent
<220> FEATURE:
<221> NAME/KEY: VARIANT
<222> LOCATION: (12)...(12)
<223> OTHER INFORMATION: Xaa = Vale or absent
<220> FEATURE:
```

```
<221> NAME/KEY: VARIANT
<222> LOCATION: (13)...(13)
<223> OTHER INFORMATION: Xaa = Tyr or absent
<220> FEATURE:
<221> NAME/KEY: VARIANT
<222> LOCATION: (14)...(14)
<223> OTHER INFORMATION: Xaa = Tyr or absent
<220> FEATURE:
<221> NAME/KEY: VARIANT
<222> LOCATION: (15)...(15)
<223> OTHER INFORMATION: Xaa = Tyr or absent
<220> FEATURE:
<221> NAME/KEY: VARIANT
<222> LOCATION: (16)...(16)
<223> OTHER INFORMATION: Xaa = Gly or absent
<220> FEATURE:
<221> NAME/KEY: VARIANT
<222> LOCATION: (17)...(17)
<223> OTHER INFORMATION: Xaa = Met or absent
<220> FEATURE:
<221> NAME/KEY: VARIANT
<222> LOCATION: (18)...(18)
<223> OTHER INFORMATION: Xaa = Asp or absent
<220> FEATURE:
<221> NAME/KEY: VARIANT
<222> LOCATION: (19)...(19)
<223> OTHER INFORMATION: Xaa = Val or absent

<400> SEQUENCE: 247

Xaa Xaa Xaa Xaa Xaa Xaa Xaa Xaa Xaa Xaa Xaa Xaa Xaa Xaa Xaa Xaa
 1               5                   10                  15

Xaa Xaa Xaa

<210> SEQ ID NO 248
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gly
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Trp

<400> SEQUENCE: 248

Xaa Xaa Xaa Xaa Xaa Xaa
 1               5

<210> SEQ ID NO 249
<211> LENGTH: 3
<212> TYPE: PRT
<213> ORGANISM: Artificial Sequence
<220> FEATURE:
<223> OTHER INFORMATION: Synthetic
<220> FEATURE:
```

```
<221> NAME/KEY: VARIANT
<222> LOCATION: (1)...(1)
<223> OTHER INFORMATION: Xaa = Gly or Ala
<220> FEATURE:
<221> NAME/KEY: VARIANT
<222> LOCATION: (2)...(2)
<223> OTHER INFORMATION: Xaa = Ala
<220> FEATURE:
<221> NAME/KEY: VARIANT
<222> LOCATION: (3)...(3)
<223> OTHER INFORMATION: Xaa = Ser

<400> SEQUENCE: 249

Xaa Xaa Xaa
 1

<210> SEQ ID NO 250
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gln or His
<220> FEATURE:
<221> NAME/KEY: VARIANT
<222> LOCATION: (3)...(3)
<223> OTHER INFORMATION: Xaa = Ala
<220> FEATURE:
<221> NAME/KEY: VARIANT
<222> LOCATION: (4)...(4)
<223> OTHER INFORMATION: Xaa = Asn or Tyr
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Phe
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Pro
<220> FEATURE:
<221> NAME/KEY: VARIANT
<222> LOCATION: (9)...(9)
<223> OTHER INFORMATION: Xaa = Thr

<400> SEQUENCE: 250

Xaa Xaa Xaa Xaa Xaa Xaa Xaa Xaa Xaa
 1               5

<210> SEQ ID NO 251
<211> LENGTH: 311
<212> TYPE: PRT
<213> ORGANISM: Macaca Fascicularis

<400> SEQUENCE: 251

Ala Pro Gly Gly Cys Pro Ala Gln Glu Val Ala Arg Gly Val Leu Thr
 1               5                  10                  15

Ser Leu Pro Gly Asp Ser Val Thr Leu Thr Cys Pro Gly Gly Glu Pro
                20                  25                  30
```

```
Glu Asp Asn Ala Thr Val His Trp Val Leu Arg Lys Pro Ala Val Gly
         35                  40                  45

Ser His Leu Ser Arg Trp Ala Gly Val Gly Arg Arg Leu Leu Leu Arg
 50                  55                  60

Ser Val Gln Leu His Asp Ser Gly Asn Tyr Ser Cys Tyr Arg Ala Gly
 65                  70                  75                  80

Arg Pro Ala Gly Thr Val His Leu Leu Val Asp Val Pro Pro Glu Glu
                 85                  90                  95

Pro Gln Leu Ser Cys Phe Arg Lys Ser Pro Leu Ser Asn Val Ala Cys
                100                 105                 110

Glu Trp Gly Pro Arg Ser Thr Pro Ser Pro Thr Thr Lys Ala Val Leu
                115                 120                 125

Leu Val Arg Lys Phe Gln Asn Ser Pro Ala Glu Asp Phe Gln Glu Pro
                130                 135                 140

Cys Gln Tyr Ser Gln Glu Ser Gln Lys Phe Ser Cys Gln Leu Ala Val
145                 150                 155                 160

Pro Glu Gly Asp Ser Ser Phe Tyr Ile Val Ser Met Cys Val Ala Ser
                165                 170                 175

Ser Val Gly Ser Lys Leu Ser Lys Thr Gln Thr Phe Gln Gly Cys Gly
                180                 185                 190

Ile Leu Gln Pro Asp Pro Pro Ala Asn Ile Thr Val Thr Ala Val Ala
                195                 200                 205

Arg Asn Pro Arg Trp Leu Ser Val Thr Trp Gln Asp Pro His Ser Trp
        210                 215                 220

Asn Ser Ser Phe Tyr Arg Leu Arg Phe Glu Leu Arg Tyr Arg Ala Glu
225                 230                 235                 240

Arg Ser Lys Thr Phe Thr Thr Trp Met Val Lys Asp Leu Gln His His
                245                 250                 255

Cys Val Ile His Asp Ala Trp Ser Gly Leu Arg His Val Val Gln Leu
                260                 265                 270

Arg Ala Gln Glu Glu Phe Gly Gln Gly Glu Trp Ser Glu Trp Ser Pro
        275                 280                 285

Glu Ala Met Gly Thr Pro Trp Thr Glu Ser Arg Ser Pro Pro Ala Glu
        290                 295                 300

Asn Glu Val Ser Thr Pro Thr
305                 310
```

METHOD OF TREATING RHEUMATOID ARTHRITIS WITH AN ANTI-IL-6R ANTIBODY

CROSS-REFERENCE TO RELATED APPLICATIONS

This application is a divisional of U.S. patent application Ser. No. 12/780,006 filed on May 14, 2010, now U.S. Pat. No. 8,080,248, which is a continuation-in-part of U.S. patent application Ser. No. 12/501,657 filed on Jul. 13, 2009, now U.S. Pat. No. 8,043,617, which is a divisional of U.S. patent application Ser. No. 11/809,482 filed on Jun. 1, 2007, now U.S. Pat. No. 7,582,298, which claims the benefit under 35 U.S.C. §119(e) of U.S. provisional application Nos. 60/810,664 filed on Jun. 2, 2006; and 60/843,232 filed on Sep. 8, 2006. U.S. patent application Ser. No. 12/780,006 also claims the benefit under 35 U.S.C. §119(e) of U.S. provisional application Nos. 61/181,749 filed on May 28, 2009; 61/262,661 filed on Nov. 19, 2009; and 61/297,302 filed on Jan. 22, 2010. The disclosures of all the foregoing are herein incorporated by reference in their entireties.

FIELD OF THE INVENTION

The present invention relates to the field of therapeutic treatment of rheumatoid arthritis. More specifically, the invention relates to the use of interleukin-6 receptor (IL-6R) antagonists, such as anti-IL-6R antibodies, to treat rheumatoid arthritis.

BACKGROUND

Rheumatoid arthritis (RA) is an autoimmune disease characterized by chronic inflammation of synovial tissue, leading to destruction of the joint architecture. It is recognized that cytokines such as tumor necrosis factor (TNF), interleukin-1 (IL-1) and interleukin-6 (IL-6) play a role in joint inflammation and cartilage damage observed in RA. IL-6 is a pleiotropic cytokine with biological effects on many cell types. IL-6 is often regarded as being downstream of TNF or IL-1 in inflammatory cytokine cascades and may therefore represent a common pathway factor in a wide range of inflammatory processes. Blockade of IL-6 signaling therefore offers the potential to ameliorate multiple pathogenic features of RA and other inflammatory diseases.

Therapeutic methods using IL-6R antagonists are mentioned in U.S. Pat. Nos. 5,888,510; 6,723,319; and 2001/0001663. Exemplary anti-IL-6R antibodies are described in U.S. Pat. Nos. 7,582,298; 6,410,691; 5,817,790; 5,795,695; 6,670,373; and 7,582,298.

BRIEF SUMMARY OF THE INVENTION

In a first aspect, the invention provides human antibodies, preferably recombinant human antibodies, that specifically bind human interleukin-6 receptor (hIL-6R). These antibodies are characterized by binding to hIL-6R with high affinity and slow dissociation kinetics and by the ability to neutralize IL-6 activity. The antibodies can be full-length (for example, an IgG1 or IgG4 antibody) or may comprise only an antigen-binding portion (for example, a Fab, F(ab')$_2$ or scFv fragment), and may be modified to effect functionality, e.g., to eliminate residual effector functions (Reddy et al. (2000) J. Immunol. 164:1925-1933). In a preferred embodiment, the invention provides an antibody or antigen-binding fragment thereof, which binds human IL-6 receptor (SEQ ID NO:1) with a $K_D$ of about 500 pM or less, as measured by surface plasmon resonance. In a more specific embodiment, the antibody or antigen-binding fragment has a $K_D$ of less than 300 pM, or less than 200 pM, or even less than 100 pM. In various embodiments, the antibody or antigen-binding fragment thereof blocks hIL-6 activity with an $IC_{50}$ of 250 pM or less, as measured by luciferase bioassay. In more specific embodiments, the antibody or antigen-binding fragment thereof exhibits an $IC_{50}$ of 150 pM or less.

In related aspects, the antibody or antigen-binding fragment of the invention binds hIL-6R with an affinity at least 2-fold higher than it binds monkey IL-6R. In more preferred embodiments, the antibody or antigen-binding fragment binds hIL-6R protein (SEQ ID NO:1) with an affinity that is up to about 3-fold higher relative to its binding to monkey IL-6R (*Macaca fascicularis* extracellular domain shown in SEQ ID NO:251).

In one embodiment, the antibody or antigen-binding portion of the antibody of the invention comprises a heavy chain variable region (HCVR) selected from the group consisting of SEQ ID NO:3, 227, 19, 231, 35, 51, 67, 83, 99, 115, 131, 147, 239, 241, 163, 179, 235, 195 and 211, or substantially similar sequence thereof. In a more specific embodiment, the antibody or antigen-binding fragment thereof further comprises a light chain variable region (LCVR) selected from the group consisting of SEQ ID NO: 11, 229, 27, 233, 43, 59, 75, 91, 107, 123, 139, 155, 171, 187, 203 and 219, or a substantially similar sequence thereof. In specific embodiments, the antibody or antigen-binding fragment thereof comprise HCVR/LCVR pairs selected from the group consisting of SEQ ID NO:3/11; 227/229; 19/27; 231/233; 35/43; 51/59; 67/75; 83/91; 99/107; 115/123; 131/139; 147/155; 239/155; 241; 155; 163/171; 179/187; 235/237; 195/203; and 211/219, or substantially similar sequences thereof.

In a second aspect, the invention provides isolated nucleic acid molecules that encode an antibody or antigen-binding fragment of an antibody of the invention. In one embodiment, the nucleic acid molecule of the invention encodes an antibody or fragment thereof comprising an HCVR as described above. In specific embodiments, the nucleic acid molecule encoding the HCVR is selected from the group consisting of SEQ ID NO:2, 226, 18, 230, 34, 50, 66, 82, 98, 114, 130, 146, 238, 240, 162, 178, 234, 194 and 210, or a substantially identical sequence thereof. In a related aspect, the invention provides an isolated nucleic acid molecule encoding an LCVR as described above. In specific embodiments, the nucleic acid molecule encoding the LCVR is a nucleotide sequence selected from the group consisting of SEQ ID NO: 10, 228, 26, 232, 42, 58, 74, 90, 106, 122, 138, 154, 170, 186, 236, 202 and 218, or a substantially identical sequence thereof.

In a third aspect, the invention features an antibody or antigen-binding fragment, comprising a heavy chain complementary determining region 3 (CDR3) domain and a light chain CDR3 domain, wherein: the heavy chain CDR3 domain comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$ (SEQ ID NO:247) wherein $X^1$=Ala, $X^2$=Lys, $X^3$=Gly, $X^4$=Arg, $X^5$=Asp, $X^6$=Ser or Ala, $X^7$=Phe, $X^8$=Asp; $X^9$=Ile, $X^{10}$=Pro or absent, $X^{11}$=Phe or absent, $X^{12}$=Val or absent, $X^{13}$=Tyr or absent, $X^{14}$=Tyr or absent, $X^{15}$=Tyr or absent, $X^{16}$=Gly or absent, $X^{17}$=Met or absent, $X^{18}$=Asp or absent, and $X^{19}$=Val or absent; and the light chain CDR3 domain comprises an amino acid sequence of the formula $X^1$-$X^2$-$X^3$-$X^4$-$X^5$-$X^6$-$X^7$-$X^8$-$X^9$ (SEQ ID NO:250) wherein $X^1$=Gln, $X^2$=Gln or His, $X^3$=Ala, $X^4$=Asn or Tyr, $X^5$=Ser, $X^6$=Phe, $X^7$=Pro, $X^8$=Pro, and $X^9$=Thr.

In a more specific embodiment, the antibody or antigen-binding fragment further comprises: a heavy chain CDR1 domain comprising an amino acid sequence of the formula $X^1$-$X^2$-$X^3$-$X^4$-$X^5$-$X^6$-$X^7$-$X^8$ (SEQ ID NO:245) wherein $X^1$=Gly or Arg, $X^2$=Phe, $X^3$=Thr, $X^4$=Phe, $X^5$=Asp, $X^6$=Asp, $X^7$=Tyr, and $X^8$=Ala; a heavy chain CDR2 domain comprising an amino acid sequence of the formula $X^1$-$X^2$-$X^3$-$X^4$-$X^5$-$X^6$-$X^7$-$X^8$ (SEQ ID NO:246) wherein $X^1$=Ile or Val, $X^2$=Ser, $X^3$=Trp, $X^4$=Asn, $X^5$=Ser, $X^6$=Gly, $X^7$=Ser, and $X^8$=Ile; light chain CDR1 domain comprising an amino acid sequence of the formula $X^1$-$X^2$-$X^3$-$X^4$-$X^5$-$X^6$ (SEQ ID NO:248), wherein $X^1$=Gln, $X^2$=Gly, $X^3$=Ile, $X^4$=Ser, $X^5$=Ser, and $X^6$=Trp; and a light chain CDR2 domain comprising an amino acid sequence of the formula $X^1$-$X^2$-$X^3$ (SEQ ID NO:249), wherein $X^1$=Gly or Ala, $X^2$=Ala, and $X^3$=Ser.

In a fourth aspect, the invention features an antibody or antigen-binding fragment, comprising: a heavy chain CDR3 domain selected from the group consisting of SEQ ID NO: 25, 153, 9, 185, 41, 57, 73, 89, 105, 121, 137, 169, 201 and 217; and a light chain CDR3 domain selected from the group consisting of SEQ ID NO:33, 161, 17, 193, 49, 65, 81, 97, 113, 129, 145, 177, 209 and 225.

In a more specific embodiment, the antibody or antigen-binding fragment further comprises: a heavy chain CDR1 domain selected from the group consisting of SEQ ID NO: 21, 149, 5, 181, 37, 53, 69, 85, 101, 117, 133, 165, 197, and 213; a heavy chain CDR2 domain selected from the group consisting of SEQ ID NO: 23, 151, 7, 183, 39, 55, 71, 87, 103, 119, 135, 167, 199 and 215; a light chain CDR1 domain selected from the group consisting of SEQ ID NO: 29, 157, 13, 189, 45, 61, 77, 93, 109, 125, 141, 173, 205 and 221; and a light chain CDR2 domain selected from the group consisting of SEQ ID NO: 31, 159, 15, 191, 47, 63, 79, 95, 111, 127, 143, 175, 207 and 223.

In specific embodiments, the antigen or antigen-binding fragment comprises heavy chain CDR sequences SEQ ID NO:21, 23, 25 and light chain CDR sequences SEQ ID NO:29, 31, 33; heavy chain CDR sequences SEQ ID NO:149, 151, 153 and light chain CDR sequences SEQ ID NO:157, 159, 161; heavy chain CDR sequences SEQ ID NO:5, 7, 9 and light chain SEQ ID NO: 13, 15, 17; and heavy chain CDR sequences SEQ ID NO: 181. 183, 185 and light chain CDR sequences SEQ ID NO:189, 191, 193.

In a fifth aspect, the invention features isolated nucleic acid molecules encoding an antibody or antigen-binding fragments of the invention, wherein the antibody or fragment thereof comprises: a heavy chain CDR3 domain encoded by a nucleotide sequence selected from the group consisting of SEQ ID NO:24, 152, 8, 184, 40, 56, 72, 88, 104, 120, 136, 168, 200 and 216; and a light chain CDR3 domain encoded by a nucleotide sequence selected from the group consisting of SEQ ID NO:32, 160, 16, 192, 48, 64, 80, 96, 112, 128, 144, 176, 208 and 224; as well as substantially identical nucleic acid sequences thereof.

In a more specific embodiment, isolated nucleic acid molecules are provided encoding an antibody or antigen-binding fragment of the invention, wherein the antibody or fragment thereof comprises: a heavy chain CDR1 encoded by a nucleotide sequence selected from the group consisting of SEQ ID NO:20, 148, 4, 180, 36, 52, 68, 84, 100, 116, 132, 164, 196 and 212; a heavy chain CDR2 domain encoded by a nucleotide sequence selected from the group consisting of SEQ ID NO:22, 150, 6, 182, 38, 54, 70, 86, 102, 118, 134, 166, 198 and 214; a light chain CDR1 domain encoded by a nucleotide sequence selected from the group consisting of SEQ ID NO:28, 156, 12, 188, 44, 60, 76, 92, 108, 124, 140, 172, 204 and 220; and a light chain CDR2 domain encoded by a nucleotide sequence selected from the group consisting of SEQ ID NO:30, 158, 14, 190, 46, 62, 78, 94, 110, 126, 142, 174, 206 and 222; as well as substantially identical nucleic acid sequences thereof.

The invention encompasses anti-hIL-6R antibodies or antigen-binding fragments thereof having a modified glycosylation pattern. In some applications, modification to remove undesirable glycosylation sites may be useful, or an antibody lacking a fucose moiety on an oligosaccharide chain, for example, to increase antibody-dependent cellular cytotoxicity (ADCC) (see Shield et al. (2002) JBC 277:26733). In other applications, modification of a galactosylation can be made in order to modify complement-dependent cytotoxicity (CDC).

In further aspects, the invention provides recombinant expression vectors carrying the nucleic acid molecules of the invention, and host cells into which such vectors have been introduced, as are methods of making the antibodies or antigen-binding fragments of the invention obtained by culturing the host cells of the invention. The host cell may be a prokaryotic or eukaryotic cell, preferably the host cell is an *E. coli* cell or a mammalian cell, such as a CHO cell.

In a further aspect, the invention features a pharmaceutical composition comprising a human antibody or antigen-binding fragment of an antibody which specifically binds hIL-6R and a pharmaceutically acceptable carrier.

The present invention additionally provides methods for treating rheumatoid arthritis. The methods of the present invention comprise administering to a patient in need of such treatment a therapeutically effective amount of a human antibody or antigen-binding fragment of an antibody which specifically binds to human interleukin-6 receptor (hIL-6R).

The studies summarized in Examples 8-12 below utilize an anti-hIL-6R antibody referred to as "mAb1." This antibody is also referred to herein as VQ8F11-21. mAb1 (VQ8F11-21) comprises an HCVR/LCVR amino acid sequence pair having SEQ ID NOs:19/27, and HCDR1-HCDR2-HCDR3/LCDR1-LCDR2-LCDR3 domains represented by SEQ ID NOs:21-23-25/SEQ ID NOs:29-31-33. However, the methods of the present invention can be practiced using any anti-IL-6R antibody disclosed herein, as well as variants and antigen-binding fragments of such antibody.

Examples 10-12 were designed to determine the effects of mAb1 administration on inflammation, as well as the safety and tolerability of mAb1 in RA patients, and to determine the time course of bioeffect on RA-associated markers after a subcutaneous dose of mAb1. As demonstrated in Example 12, dose-dependent reduction in high-sensitivity C-reactive protein (hsCRP) was observed through day 15 (p<0.0047). Suppression of serum amyloid A (SAA), erythrocyte sedimentation rate (ESR) and serum hepcidin was also observed in a dose-related manner. Significant increases in IL-6 were also observed. At day 8, a 200 mg dose of mAb1 was associated with median percent changes of −91.7% in hsCRP, −92.5% in SAA, −33.8% in ESR, −66.2% in hepcidin, and +647.0% in IL-6.

Safety data from all three studies (Examples 10-12) were combined [mAb1 (n=71) or placebo (n=24)]. During a maximum 16-week exposure period, 16.9% and 2.4% of patients receiving mAb1 and placebo had at least one neutrophil count of $1.0$-$1.5 \times 10^3$/uL; and 7.0% and 0% had a neutrophil count of $0.5$-$1.0 \times 10^3$/uL. During exposure, 50.1% and 20.1% of patients receiving mAb1 and placebo had at least one alanine aminotransferase (ALT) elevation 1-3 times the upper limit of normal (x ULN); 1.4% and 4.2% had ALT 3-5×ULN; and 1.4% and 0% had ALT >5×ULN. No alterations in neutrophils or liver enzymes were associated with adverse clinical outcomes.

In summary, IL-6R inhibition with subcutaneous administration of mAb1 was well tolerated in patients with RA with no dose-limiting toxicities observed. Target blockade was demonstrated by the significant increase in IL-6 after treatment. mAb1 administered to active RA patients resulted in dose-related reduction in hsCRP, SAA, and ESR; the observed reduction of hepcidin within one week of treatment is believed to be the first reported demonstration of hepcidin reduction in RA in humans. Moreover, hsCRP was suppressed for two weeks after a single 200 mg dose of mAb1, suggesting that weekly or bi-weekly SC dosing may prove to be efficacious.

The present invention also includes methods of modifying a rheumatoid arthritis-associated biomarker in a patient by administering to the patient an anti-hIL-6R antibody or antigen-binding fragment thereof. Exemplary RA-associated biomarkers include, e.g., high-sensitivity C-reactive protein (hsCRP), serum amyloid A (SAA), erythrocyte sedimentation rate (ESR), serum hepcidin, hemoglobin, and interleukin-6 (IL-6).

According to certain aspects of the present invention, the anti-hIL-6R antibody may be administered to a patient subcutaneously (s.c.) or intravenously (iv). The anti-hIL-6R antibody may also be administered to the patient in combination with one or more additional therapeutic agents. In certain embodiments, the anti-hIL-6R antibody is administered in multiple, sequential doses to a patient.

The present invention further includes the use of any of the anti-hIL-6R antibodies, antigen-binding fragments, and/or pharmaceutical formulations disclosed herein in the manufacture of a medicament for the treatment, prevention and/or amelioration of rheumatoid arthritis.

Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference to describe in their entirety.
Anti-hIL-6R Antibodies The present invention includes methods that comprise administering to a patient a human antibody, or an antigen-binding fragment thereof, that binds specifically to hIL-6R. As used herein, the term "hIL-6R" means a human cytokine receptor that specifically binds human interleukin-6 (IL-6). In certain embodiments, the antibody that is administered to the patient binds specifically to the extracellular domain of hIL-6R. The extracellular domain of hIL-6R is shown in the amino acid sequence of SEQ ID NO:1.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$—$C_{H1}$; (ii) $V_H$—$C_{H2}$; (iii) $V_H$—$C_{H3}$; (iv) $V_H$—$C_{H1}$—$C_{H2}$; (v) $V_H$—$C_{H1}$—$C_{H2}$—$C_{H3}$; (vi) $V_H$—$C_{H2}$—$C_{H3}$; (vii) $V_H$—$C_L$; (viii) $V_L C_{H1}$; (ix) $V_L$—$C_{H2}$; (x) $V_L$—$C_{H3}$; (xi) $V_L$—$C_{H1}$—$C_{H2}$; (xii) $V_L$—$C_{H1}$—$C_{H2}$—$C_{H3}$; (xiii) $V_L$—$C_{H2}$—$C_{H3}$; and (xiv) $V_L$—$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "specifically binds," means that an antibody or antigen-binding fragment thereof forms a complex with an antigen that is relatively stable under physiologic conditions. Specific binding can be characterized by a dissociation constant of at least about $1 \times 10^{-6}$ M or smaller. Methods for determining whether two molecules specifically bind are well known in the art and include, for example, equilibrium dialysis, surface plasmon resonance, and the like.

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In specific embodiments, the antibody or antibody fragment for use in the method of the invention may be a multispecific antibody, which may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bispecific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise an Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

A "neutralizing" or "blocking" antibody, as used herein, is intended to refer to an antibody whose binding to hIL-6R results in inhibition of the biological activity of hIL-6. This inhibition of the biological activity of hIL-6 can be assessed by measuring one or more indicators of hIL-6 biological activity known to the art, such as hIL-6-induced cellular activation and hIL-6 binding to hIL-6R (see examples below).

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Therapeutic Administration and Formulations

The methods of the present invention comprise administering a therapeutically effective amount of an anti-hIL-6R antibody to a patient. As used herein, the phrase "therapeutically effective amount" means a dose of anti-hIL-6R antibody that results in a detectable improvement in one or more symptoms associated with rheumatoid arthritis or which causes a biological effect (e.g., a decrease in the level of a particular biomarker) that is correlated with the underlying pathologic mechanism(s) giving rise to the condition or symptom(s) of rheumatoid arthritis. For example, a dose of anti-hIL-6R antibody which causes an improvement in any of the following symptoms or conditions is deemed a "therapeutically effective amount": chronic disease anemia, fever, depression, fatigue, rheumatoid nodules, vasculitis, neuropathy, scleritis, pericarditis, Felty's syndrome and/or joint destruction.

In accordance with the methods of the present invention, a therapeutically effective amount of anti-hIL-6R antibody that is administered to the patient will vary depending upon the age and the size (e.g., body weight or body surface area) of the patient as well as the route of administration and other factors well known to those of ordinary skill in the art. In certain embodiments, the dose of anti-hIL-6R antibody administered to the patient is from about 10 mg to about 500 mg. For example, the present invention includes methods wherein about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300, about 325 mg, about 350 mg, about 375 mg, about 400 mg, about 425 mg, about 450 mg, about 475 mg, about 500 mg, or more of anti-hIL-6R antibody is administered to the patient.

The amount of anti-hIL-6R antibody that is administered to the patient may be expressed in terms of milligrams of antibody per kilogram of patient body weight (i.e., mg/kg). For example, the methods of the present invention include administering an anti-hIL-6R antibody to a patient at a daily dose of about 0.01 to about 100 mg/kg, about 0.1 to about 50 mg/kg, or about 1 to about 10 mg/kg of patient body weight.

The methods of the present invention include administering multiple doses of an anti-hIL-6R antibody to a patient over a specified time course. For example, the anti-hIL-6R antibody can be administered about 1 to 5 times per day, about 1 to 5 times per week, about 1 to 5 times per month or about 1 to 5 times per year. In certain embodiments, the methods of the invention include administering a first dose of anti-hIL-6R antibody to a patient at a first time point, followed by administering at least a second dose of anti-hIL-6R antibody to the patient at a second time point. The first and second doses, in certain embodiments, may contain the same amount of anti-hIL-6R antibody. For instance, the first and second doses may each contain about 10 mg to about 500 mg, about 20 mg to about 300 mg, about 50 mg to about 200 mg, or about 75 mg to about 150 mg of the antibody. The time between the first and second doses may be from about a few hours to several weeks. For example, the second time point (i.e., the time when the second dose is administered) can be from about 1 hour to about 7 weeks after the first time point (i.e., the time when the first dose is administered). According to certain exemplary embodiments of the present invention, the second time point can be about 1 hour, about 4 hours, about 6 hours, about 8 hours, about 10 hours, about 12 hours, about 24 hours, about 2 days, about 3 days, about 4 days, about 5 days, about 6 days, about 7 days, about 2 weeks, about 4 weeks, about 6 weeks, about 8 weeks, about 10 weeks, about 12 weeks, about 14 weeks or longer after the first time point. Third and subsequent doses may be similarly administered throughout the course of treatment of the patient.

The invention provides methods of using therapeutic compositions comprising anti-IL-6R antibodies or antigen-binding fragments thereof. The therapeutic compositions of the invention will be administered with suitable carriers, excipients, and other agents that are incorporated into formulations to provide improved transfer, delivery, tolerance, and the like.

A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262: 4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can also be delivered in a vesicle, in particular a liposome (see Langer (1990) Science 249:1527-1533). In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 1 to 500 mg per dosage form in a unit dose; especially in the form of injection, it is preferred that the antibody is contained in about 5 to 100 mg and in about 10 to 250 mg for the other dosage forms.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

In accordance with the methods of the present invention, the anti-hIL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an anti-hIL-6R antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen and/or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park, Ill.), to name only a few.

The use of a microinfusor to deliver an anti-hIL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. No. 6,629,949; U.S. Pat. No. 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) and/or viscous solutions.

Combination Therapies

The present invention includes methods of treating rheumatoid arthritis which comprise administering to a patient in need of such treatment an anti-hIL-6R antibody in combination with at least one additional therapeutic agent. Examples of additional therapeutic agents which can be administered in combination with an anti-hIL-6R antibody in the practice of the methods of the present invention include, but are not limited to NSAIDs, DMARDs, TNFα antagonists, T-cell blockers, CD-20 antagonists (e.g., anti-CD-20 antibodies), IL-1 antagonists, JAK antagonists, IL-17 antagonists, and any other compound known to treat, prevent, or ameliorate rheumatoid arthritis in a human subject. Specific, non-limiting examples of additional therapeutic agents that may be administered in combination with an anti-hIL-6R antibody in the context of a method of the present invention include, but are not limited to methotrexate, sulfasalazine, hydroxychloroquine, leflunomide, etanercept, infliximab, adalimumab, golimumab, rilonacept, anakinra, abatacept, certolizumab and rituximab. In the present methods, the additional therapeutic agent(s) can be administered concurrently or sequentially with the anti-hIL-6R antibody. For example, for concurrent administration, a pharmaceutical formulation can be made which contains both an anti-hIL-6R antibody and at least one additional therapeutic agent. The amount of the additional therapeutic agent that is administered in combination with the anti-hIL-6R antibody in the practice of the methods of the present invention can be easily determined using routine methods known and readily available in the art.

Biomarkers

The present invention includes methods of treating rheumatoid arthritis by administering to a patient in need of such treatment a therapeutically effective amount of a human antibody or antibody binding fragment thereof which specifically binds to hIL-6R, wherein the level of one or more RA-associated biomarkers in the patient is modified (e.g., increased, decreased, etc., as the case may be) following administration. In a related aspect, the present invention includes methods for decreasing an RA-associated biomarker in a patient by administering to the patient a therapeutically-effective amount of a human antibody or antigen-binding fragment thereof which specifically binds to hIL-6R.

Examples of RA-associated biomarkers include, but are not limited to, e.g., high-sensitivity C-reactive protein (hsCRP), serum amyloid A (SAA), erythrocyte sedimentation rate (ESR), serum hepcidin, interleukin-6 (IL-6), and hemoglobin (Hb). As will be appreciated by a person of ordinary skill in the art, an increase or decrease in an RA-associated biomarker can be determined by comparing the level of the biomarker measured in the patient at a defined time point after administration of the anti-IL-6R antibody to the level of the biomarker measured in the patient prior to the administration (i.e., the "baseline measurement"). The defined time point at which the biomarker can be measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days or more after administration of the anti-hIL-6R antibody.

According to certain embodiments of the present invention, a patient may exhibit a decrease in the level of one or more of hsCRP, SAA, ESR and/or hepcidin following administration of an anti-hIL-6R antibody to the patient. For example, at about day 8 following administration of a single dose of about 200 mg of an anti-hIL-6R antibody (e.g., mAb1), the patient may exhibit one or more of the following: (i) a decrease in hsCRP by about 40%, 45%, 50%, 55%, 60%, 65%, 70%, 75%, 80%, 85%, 90%, 95% or more; (ii) a decrease in SAA by about 40%, 45%, 50%, 55%, 60%, 65%, 70%, 75%, 80%, 85%, 90%, 95% or more; (iii) a decrease in ESR by about 15%, 20%, 25%, 30%, 35%, 40%, 45%, 50%, 55% or more; and/or (iv) a decrease in hepcidin by about 30%, 35%, 40%, 45%, 50%, 55%, 60%, 65%, 70%, 75% or more.

According to certain other embodiments of the present invention, a patient may exhibit an increase in the level of one or more of Hb or IL-6 following administration of an anti-hIL-6R antibody to the patient. For example, at about day 8 following administration of a single dose of about 200 mg of an anti-hIL-6R antibody (e.g., mAb1), the patient may exhibit one or more of the following: (v) an increase in Hb by about 0.5%, 1.0%, 1.5%, 2.0%, 2.5%, 3.0%, 3.5%, 4.0%, 4.5%, 5.0%, 5.5%, 6.0% or more; and/or (vi) an increase in IL-6 by about 100%, 150%, 200%, 250%, 300%, 350%, 400%, 450%, 500%, 550%, 600%, 650%, 700%, 750%, 800% or more.

The present invention includes methods for determining whether a subject is a suitable patient for whom administration of an anti-hIL-6R antibody would be beneficial. For example, if an individual, prior to receiving an anti-hIL-6R antibody, exhibits a level of an RA-associated biomarker which signifies the disease state, the individual is therefore identified as a suitable patient for whom administration of an anti-hIL-6R antibody would be beneficial. According to certain exemplary embodiments, an individual may be identified as a good candidate for anti-hIL-6R therapy if the individual exhibits one or more of the following: (i) a level of hsCRP greater than about 4 mg/L (e.g., about 4.5 mg/L, about 5.0 mg/L, about 5.5 mg/L, about 6.0 mg/L, about 7.0 mg/L, about 10.0 mg/L, about 15.0 mg/L, about 20.0 mg/L, or more); (ii) a level of SAA greater than about 3800 ng/mL (e.g., about 4000 ng/mL, 4500 ng/mL, about 5000 ng/mL, about 5500 ng/mL, about 6000 ng/mL, about 10,000 ng/mL, about 20,000 ng/mL, about 25,000 ng/mL, about 30,000 ng/mL, about 35,000 ng/mL, about 40,000 ng/mL, about 45,000 ng/mL, or more); (iii) an ESR greater than about 15 mm/hr (e.g., about 16 mm/hr, about 17 mm/hr, about 18 mm/hr, about 19 mm/hr, about 20 mm/hr, about 21 mm/hr, about 22 mm/hr, about 25 mm/hr, about 30 mm/hr, about 35 mm/hr, about 40 mm/hr, about 45 mm/hr, about 50 mm/hr, or more); and/or (iv) a level of hepcidin greater than about 60 ng/mL (e.g., about 62 ng/mL, about 64 ng/mL, about 68 ng/mL, about 70 ng/mL, about 72 ng/mL, about 74 ng/mL, about 76 ng/mL, about 78 ng/mL, about 80 ng/mL, about 82 ng/mL, about 84 ng/mL, about 85 ng/mL, about 90 ng/mL, about 95 ng/mL, about 100 ng/mL, about 105 ng/mL, or more). Additional criteria, such as other clinical indicators of RA, may be used in combination with any of the foregoing RA-associated biomarkers to identify an individual as a suitable candidate for anti-hIL-6R therapy.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-6 Receptor

Immunization of rodents can be done by any methods known in the art (see, for example, Harlow and Lane (1988) supra; Malik and Lillehoj, Antibody techniques: Academic Press, 1994, CA). In a preferred embodiment, hIL-6R antigen is administered directly to mice which comprise DNA loci encoding both human Ig heavy chain variable region and Kappa light chain variable region (VelocImmune™, Regeneron Pharmaceuticals, Inc.; U.S. Pat. No. 6,596,541), with an adjuvant to stimulate the immune response. Such an adjuvant includes complete and incomplete Freund's adjuvant, MPL+ TDM adjuvant system (Sigma), or RIBI (muramyl dipeptides) (see O'Hagan, Vaccine Adjuvant, by Human Press, 2000, NJ). Such an adjuvant can prevent rapid dispersal of polypeptide by sequestering the antigen in a local depot, and may contain factors that can stimulate host immune response. In one embodiment, hIL-6R is administered indirectly as DNA plasmid that contains hIL-6R gene and expresses hIL-6R using the host cellular protein expression machinery to produce antigen polypeptide in vivo. In both approaches, the immunization schedule requires several administrations spaced by a few weeks. The antibody immune response is monitored by standard antigen-specific immunoassay. When animals reached their maximum immune response, the antibody expressing B cells were harvested and fused with mouse myeloma cells to preserve their viability, forming hybridoma cells. To select functionally desirable monoclonal antibodies, conditioned media of the hybridoma cells or transfected cells were screened for specificity, antigen-binding affinity, and potency in blocking hIL-6 binding to hIL-6R (described below).

Example 2

Anti-hIL6R Antibodies Generated Via Direct Isolation of Splenocytes

DNA encoding VH and VL domains may be isolated directly from a single antigen positive B cell. Briefly, the hIL-6Rα immunized transgenic mouse was terminated and splenocytes were harvested. Red blood cells were removed by lysis followed by pelleting the harvested splenocytes. Resuspended splenocytes were first incubated with a cocktail of human IgG, FITC-anti-mFc, and biotin-IL6Ra for 1 hour. The stained cells were washed twice with PBS, then stained with a cocktail of human and rat IgG, APC-anti-mIgM, and SA-PE for one hour. The stained cells were washed once with PBS and were analyzed by flow cytometry on a MoFlo (Cytomation). Each IgG positive, IgM negative, and antigen positive B cell was sorted and plated into a separate well on a 96-well plate. RT-PCR of antibody genes from these B cells was performed according to a method described by Wang et al. (2000) (J Immunol Methods 244:217-225). Briefly, cDNAs for each single B cell were synthesized via RT-PCR. Each resulting RT product was then split and transferred into two corresponding wells on two 96-well plates. One set of the resulting RT products was first amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a nested 3' primer specific for mouse heavy chain constant region. The other set of the resulting RT products was first amplified by PCR using a 5' degenerate primer specific for human kappa light chain variable region leader sequence and a 3' primer specific for mouse kappa light chain constant region to form an amplicon. The amplicon was then amplified again by PCR using a 5' degenerate primer set specific for framework 1 of human kappa light chain variable region sequence and a nested 3' primer specific for mouse kappa light chain constant region. The heavy chain and light chain PCR products were cloned into Sap I-linearized antibody vectors containing IgG1 heavy chain constant region and kappa light chain constant region, respectively. The heavy chain plasmid has a lox2272 site and a lox511 site flanking the heavy chain expression cassettes. In addition, immediately downstream of the lox2272 in the heavy chain plasmid there is a hygromycin-resistance gene that lacks a promoter and an initiating ATG. The hygromycin-resistance gene is also transcriptionally linked to a downstream eGFP gene via an IRES sequence. The light chain plasmid has a loxP site and lox2272 site flanking the light chain expression cassette. In addition, The light chain plasmid has a SV40 promoter immediately before an ATG at the lox2272 site, such that upon integration into an appropriate host cell the lox2272-proximal SV40 promoter and initiating ATG from the light chain plasmid is brought adjacent to the hygromycin-resistance gene in the heavy chain plasmid in the proper reading frame to allow transcription and translation of the hygromycin-resistance and eGFP genes. Purified recombinant plasmids having a heavy chain variable region sequence and plasmids having a light chain variable region sequence from the same B cell were then combined and transfected, together with a plasmid that expresses the Cre recombinase, into a modified CHO host cell line. The modified CHO host cell line contains, from 5' to 3', a loxP site, an eCFP, a lox2272 site, DsRed, and a lox511 site at a transcriptionally active locus. Consequently, the host CHO cell can be isolated by flow cytometry as a blue-positive, red-positive, and green-negative cell. When recombinant plasmids expressing heavy chain and light chain genes are transfected together with a plasmid expressing the Cre recombinase, site-specific recombination mediated by the Cre recombinase results in the integration of the antibody plasmids at the chromosomal locus containing the lox sites and replacement of the eCFP and DsRed genes. Recombinants can then be isolated as blue-negative, red-negative, and green-positive cells by flow cytometry. Accordingly, CHO cells transfected with recombinant plasmids having a heavy chain variable region sequence and plasmids having a light chain variable region sequence from the same B cell were sorted by flow cytometry, and proper recombinants that show the blue-negative, red-negative, and green-positive phenotype were isolated, and stable recombinant antibody-expressing CHO cell lines were established from isolated clones.

Example 3

Antigen Binding Affinity Determination $K_D$ of the antigen binding to the selected antibodies described above were determined by surface kinetics on a real-time biosensor surface plasmon resonance assay (BIAcore™). More specifically, the affinity of the antibodies for human IL-6R was measured using a BIAcore® 2000 or BIAcore® 3000. The antibody was captured on an anti-mouse IgG surface and exposed to various concentrations of recombinant hIL-6R protein either in monomeric or dimeric form. Kinetic analysis using BIAevaluation™ software was performed to obtain the association and dissociation rate constants.

Binding affinities of the antibodies to hIL-6R was also measured for either hybridoma-conditioned media or purified proteins by plate-based competition immunoassay. The antibody proteins were purified using Protein G affinity chromatography from hybridoma cell conditioning medium that was bovine IgG-depleted (Invitrogen). For the competition ELISA, briefly, constant amounts of antibody at different levels were premixed with serial dilutions of antigen protein, hIL-6R-hFc, ranging from 0 to 10 µg/ml, and incubated for two hours at room temperature to reach pseudo-binding equilibrium between the antibody and antigen. These solutions were then transferred to 96-well hIL-6R-hFc pre-coated plates to allow the free-antibody in the mixtures to bind to plate-coated hIL-6R-hFc. The plates were typically coated with 1 to 2 µg/ml hIL-6R-hFc protein in PBS solution overnight at 4° C. followed by BSA nonspecific blocking. After washing off excess antibody in solution, plate-bound antibodies were detected with an HRP-conjugated goat anti-mouse IgG or IgA polyclonal antibody reagent and developed using either colorimetric or chemiluminescence substrates. The dependency of the signals on the concentrations of antigen in solution was analyzed with a 4-parameter fit analysis using Prism™ software (Graph Pad) and reported as $IC_{50}$. Competition immunoassay were also carried out using steady state solution phase Kinexa™ instrument (Sapidyne Inc.).

Results are shown in Table 1 (control: humanized monoclonal antibody to human IL-6R (U.S. Pat. No. 5,817,790 SEQ ID NO:69 and 71). Antibody (HCVR and LCVR amino acid sequences): VQ8A9-6 (3, 11); VQ8F11-21 (19, 27); VV7G4-1 (35, 43); VV7G4-10 (51, 59) VV6C10-1(67, 75); VV6C10-3 (83, 91); VV6C10-4 (99, 107); VV6F12-11 (115, 123); VV9A6-11 (131, 139); VV6A9-5 (147, 155), VV3D8-4 (163, 171); VV1G4-7 (179, 187); 248982-13-1-E5 (195, 203); 248982-13-2-A9 (211, 219). Monomer and dimer $K_D$ determined by BIAcore™; solution $K_D$ by Kinexa™; $IC_{50}$ by ELISA assays (n.d.=not determined).

TABLE 1

Antigen Binding Affinity

| Antibody | $K_D$ Monomer (nM) | $K_D$ Dimer (nM) | Solution $K_D$ Monomer (nM) | ELISA $IC_{50}$ Dimer (nM) |
|---|---|---|---|---|
| VQ8A9-6 | 0.222 | 0.101 | 0.120 | 0.004 |
| VQ8F11-21 | 0.067 | 0.023 | 0.009 | 0.008 |
| VV3D8-4 | 2.410 | 0.172 | 1.910 | 0.013 |
| VV6A9-5 | 0.097 | 0.146 | 0.032 | 0.005 |
| VV1G4-7 | 0.225 | 0.070 | 0.197 | 0.041 |
| VV6C10-1 | 0.267 | 0.032 | 2.050 | 0.010 |
| VV6F12-11 | n.d | n.d | n.d | 0.033 |
| VV7G4-10 | n.d. | n.d. | n.d. | 1.980 |
| VV9A6-11 | n.d. | n.d. | n.d. | 0.347 |
| VV6C10-3 | n.d. | n.d. | n.d. | 0.009 |
| 248982-13-1-E5 | 0.987 | 0.785 | n.d. | 0.360 |
| 248982-13-2-A9 | 2.870 | n.d. | n.d. | 0.054 |
| Control | 1.790 | n.d. | 1.960 | n.d. |

Example 4

Neutralization of hIL-6 Activity hIL-6 blocking activities of the anti-hIL-6R antibodies of the invention were screened by hIL-6 blocking immunoassays, in vitro hIL-6 dependent cell growth bioassays, and surface plasmon resonance (BIAcore™). The immunoassay was used to screen ability of the tested antibody to block hIL-6 binding to hIL-6R, and the in vitro bioassay was used to determine the potency of the antibodies in neutralizing hIL-6R-mediated cellular signal transduction.

For the immunoassay, hIL-6 recombinant protein was coated on a 96-well plate in PBS buffer overnight at 4° C. This plate was used to capture free hIL-6R-hFc from antibody sample solutions, and the amount of captured hIL-6R-hFc was quantified according to the standard curve. The sample solutions were composed of a constant amount of hIL-6R-hFc recombinant protein (100 pM) and varying amounts of antibody, either in crude hybridoma condition medium or as purified antibody protein, ranging from 0 to about 50 nM in serial dilutions. The antibody-antigen mixtures were incubated at room temperature for ~2 hours to allow antibody-antigen binding to reach equilibrium. The equilibrated sample solutions were then transferred to the hIL-6 coated plates for measurement of free hIL-6R-hFc. After 1 hour binding, the plate was washed and bound hIL-6R-hFc was detected using HRP-conjugated goat anti-hFc polyclonal antibodies (Jackson Immuno Research), and developed using TMB substrate (BD Pharmigen). $IC_{50}$s were determined as the amount of antibody required to reduce 50% of IL-6R-hFc detectable to plate bound hIL-6 ligand. Results are shown in the first column of Table 2.

Additionally, the ability of the test antibody to block hIL-6 binding to the hIL-6R receptor was determined using surface plasmon resonance. Purified antigen hIL-6R-hFc molecules were captured by goat anti-human IgG polyclonal antibodies immobilized on CM-5 surface through amine coupling to a density of 250 RU. hIL-6 solution (0.25 ml, 50 nM) was injected over the receptor surface and bound hIL-6 recorded (first injection of IL-6). Bound hIL-6 was then removed with a pulse of 3 M $MgCl_2$ following by conditioning buffer. Anti-hIL6R antibody in hybridoma conditioned medium was injected over the captured receptor surface followed by second injection of hIL-6. The percent reduction in hL-6 binding resulting from preformed antibody and receptor complex was used as a score to define hIL-6 blockers from non-blockers (second column, Table 2).

TABLE 2

Neutralization of hIL-6 Binding

| Antibody | hIL6R/hIL6 Binding Inhibition $IC_{50}$ (nM) | hIL6/hIL6R Binding Inhibition (%) | XG-1 cell proliferation Inhibition $IC_{50}$ (nM) | HepG2/Stat3 Luciferase activity $IC_{50}$ (nM) |
|---|---|---|---|---|
| VQ8A9-6 | 0.39 | 68 | 0.40 | 0.097 |
| VQ8F11-21 | 0.12 | 98 | 0.62 | 0.135 |
| VV3D8-4 | 0.61 | 93 | >100 | n.d. |
| VV6A9-5 | 0.35 | 100 | 1.10 | 0.188 |
| VV1G4-7 | 1.10 | 34 | 1.80 | 0.578 |
| VV6C10-1 | 4.60 | 61 | >6.90 | n.d. |
| VV6F12-11 | 2.20 | n.d. | n.d. | n.d. |
| VV7G4-10 | 13.00 | n.d. | n.d. | n.d. |
| VV9A6-11 | 0.50 | n.d. | n.d. | n.d. |
| VV6C10-3 | 0.06 | n.d. | n.d. | n.d. |
| Control | 2.20 | 91 | 1.50 | 0.854 |

The ability of hIL-6R antibodies to block hIL-6 activity in vitro was measured in the hIL-6-dependent myeloma line XG-1. XG-1 cells maintained in hIL-6-containing medium were washed twice with hIL-6-free media and cultured for ~24 hours in hIL-6-free medium to deplete residual hIL-6. The starved cells were then spun down and re-suspended in the medium at $4 \times 10^5$ cells per ml and plated 20,000 cells per well in a 96-well tissue culture plate. The purified antibody proteins were serially diluted in medium and added to the plated cells at concentrations ranging from 0 to 50 nM. Subsequently, recombinant hIL-6 was added to the wells to a final concentration of 8 pM. Cells were allowed to grow for ~72 hours at 37° C. in a humidified 5% $CO_2$ incubator. At the end of growth period, live cells were measured using CCK-8 kit (Dojindo, Japan). $IC_{50}$s were determined as described above, and reported in the third column of Table 2.

The ability of hIL-6R antibodies to block hIL-6 activity was also measured in vitro in the hIL-6-responsive human hepatoma cell line, HepG2. HepG2 cells were transfected with a reporter plasmid containing a STAT3 (Signal Transducer and Activator of Transcription 3) response element linked to a luciferase gene. The transfected cells were trypsinized, spun down and re-suspended in the medium at approximately $2.5 \times 10^5$ cells per ml and plated at 20,000 cells per well in a 96-well tissue culture plate. The purified antibody proteins were serially diluted in medium and added to the plated cells at concentrations ranging from 0 to 100 nM. Subsequently, recombinant hIL-6 was added to the wells to a final concentration of 50 pM. The response was measured after incubating the cells for 6 hours at 37° C. in a humidified 5% $CO_2$ incubator. Luciferase activity was measured with the Steady-Glo™ luciferase assay system (Promega). $IC_{50}$s were determined as described above, and reported in the fourth column of Table 2.

Example 5

Binding Epitope Diversity

An antibody binding competition immunoassay was performed using as a control humanized antibody to human IL-6R. Briefly, a 96-well immunosorbent plate was coated with 20 ng per well hIL-6R recombinant protein overnight at 4° C. After blocking non-specific binding with BSA, the hIL-6R binding sites on one half of the plate were saturated with binding of the control antibody by addition of 500 ng of the control per well, and to the other half of the plate was added binding buffer only. After three hours binding at room temperature, the purified antibodies were spiked in at a final concentration of 50 ng/ml with and without the preexisting control antibody in the well. After one hour of additional binding, the free antibody was washed away and the plate-bound antibody was detected with HRP-conjugated goat anti-mouse IgG or IgA, polyclonal antibody and the plate was developed using chromatic HRP substrates and absorbance at 450 nm was recorded. Percentage deductions of the binding of the anti-hIL6R antibodies by the presence of the control antibody are listed in Table 3 below. A similar experiment was conducted using surface plasmon resonance technology (Table 3). Both methods generated consistent results. Antibodies VQ8F11, VV3D8, VV6A9, VV6C10-1 bound epitopes overlapping with the control antibody; while antibodies VQ8A9, VV1G4, VV6F12, VV7G4, VV9A6, and VV6C10-3 appeared to bind distinct epitopes as antigen binding was not blocked by the control antibody. Partial competition may result from steric hindrance from the first antibody bound, even though epitopes may not be overlapping.

TABLE 3

Competition of Antigen Binding with Control Antibody

| Antibody | BIAcore ™ (% reduction) | Immunoassay (% reduction) |
|---|---|---|
| VQ8A9-6 | 26 | 3 |
| VQ8F11-21 | 96 | 79 |
| VV3D8-4 | 97 | 84 |
| VV6A9-5 | 96 | 84 |
| VV1G4-7 | 12 | 3 |
| VV6C10-1 | 90 | 80 |
| VV6F12-11 | n.d. | 3 |
| VV7G4-10 | n.d. | 26 |
| VV9A6-11 | n.d. | 18 |
| VV6C10-3 | n.d. | 1 |

Example 6

Cross-Species Binding Property

Four antibodies were tested for cross-reactivity to monkey IL-6R recombinant protein using BIAcore™ technology.

Briefly, a biosensor chip on which goat anti-mouse Fc polyclonal antibody was immobilized was used to present anti-hIL-6R monoclonal antibodies to a density of about 75 RU. Recombinant human or monkey monomeric IL-6R protein (*Macaca fascicularis*, extracellular domain; SEQ ID NO:251), at a concentration range between 1.25-40 nM, was injected over the antibody surface. The binding of the receptor to the antibody and the dissociation of the bound complex were monitored in real-time. Both association rate constant (ka) and dissociate rate constant (kd) were obtained, and $K_D$ calculated (Table 4).

TABLE 4

Comparison of Binding Affinity to Human and Monkey IL-6R

| Antibody | Antigen | ka (M$^{-1}$S$^{-1}$) | kd (S$^{-1}$) | $K_D$ (nM) |
|---|---|---|---|---|
| Control | Human IL6R | 1.74E+05 | 1.67E−04 | 0.963 |
|  | Monkey IL6R | 1.44E+05 | 1.68E−04 | 1.170 |
| VQ8F11-21 | Human IL6R | 8.51E+05 | 4.38E−05 | 0.051 |
| (mAb1) | monkey IL6R | 3.39E+05 | 4.86E−05 | 0.143 |
| VV1G4-7 | Human IL6R | 2.57E+05 | 6.18E−05 | 0.240 |
|  | monkey IL6R | no binding |  |  |
| VV6A9-5 | Human IL6R | 5.18E+05 | 8.41E−05 | 0.162 |
|  | monkey IL6R | 5.00E+05 | 7.70E−05 | 0.154 |
| VQ8A9-6 | Human IL6R | 7.32E+05 | 2.76E−04 | 0.377 |
|  | monkey IL6R | 7.31E+05 | 4.16E−04 | 0.569 |

Among the four tested antibodies, VQ8F11, VV6A9, and VQ8A9 strongly reacted to monkey receptor with $K_D$ values that differed by about 1.5- to about 3-fold from human receptor binding, respectively. VV1G4, which was not blocked by the control antibody (Table 3), showed no binding to monkey receptor despite strong binding to the human receptor with $K_D$ of 241 pM.

Example 7

Effect of Constant Region on Binding Affinity

The binding affinity to monomeric hIL-6R of four antibodies having mouse IgG, human IgG1 or human IgG4 (wild-type and modified) were determined using BIAcore™ as described above except a goat anti-human Fc polyclonal antibody surface was used to capture hIgG antibodies. Monomeric hIL-6R was injected at concentrations of 12.5, 6.25, 3.12, and 1.56 nM. The ability of the antibodies to neutralize hIL-6-dependent HepG2/STAT3 signal transduction was also determined in a luciferase assay (IC$_{50}$). IC$_{50}$s for different IgG isotypes were similar, suggesting no effect of isotype on antibody affinity for antigen.

TABLE 5

Comparison of IgG Isotypes

| Antibody | IgG | ka (M$^{-1}$S$^{-1}$) | kd (S$^{-1}$) | $K_D$ (nM) | IC$_{50}$ (nM) |
|---|---|---|---|---|---|
| VQ8F11-21 | hIgG1 | 6.22E+05 | 4.54E−05 | 0.073 | 0.150 |
| (mAb1) | hIgG4 | 7.17E+05 | 5.22E−05 | 0.073 | 0.228 |
|  | mIgG2a | 7.86E+05 | 5.27E−05 | 0.067 | 0.135 |
|  | modhIgG4 | 8.81E+05 | 4.705−05 | 0.053 | 0.249 |
| V08A9-6 | hIgG1 | 1.09E+06 | 2.60E−04 | 0.238 | 0.130 |
|  | hIgG4 | 1.17E+06 | 2.35E−04 | 0.201 | 0.185 |
|  | mIgG1 | 9.95E+05 | 2.21E−04 | 0.222 | 0.097 |
| VV6A9-5 | hIgG1 | 7.12E+05 | 8.87E−05 | 0.125 | 0.204 |
|  | hIgG4 | 5.67E+05 | 7.64E−05 | 0.135 | 0.343 |
|  | mIgG2a | 7.72E+05 | 7.52E−05 | 0.097 | 0.188 |
| VQ1G4-21 | hIgG1 | 3.34E+05 | 7.92E−05 | 0.237 | 0.767 |
|  | hIgG4 | 2.73E+05 | 9.18E−05 | 0.336 | 0.528 |
|  | mIgG2a | 3.41E+05 | 7.66E−05 | 0.225 | 0.578 |

Example 8

Pharmacokinetics Studies of a Human Anti-IL-6R Antibody mAb1

The pharmacokinetics of mAb1 (HCVR SEQ ID NO:19 and LCVR SEQ ID NO:27) was examined in cynomolgus monkeys following a single subcutaneous (SC) or IV injection at multiple dose levels. Doses for SC administration were 1, 5, and 15 mg/kg; IV doses were 1 and 15 mg/kg. Blood samples were collected from all animals (N=6 per group, 3 per sex per group) at selected time points over a 52 day (1248 hr) time course. The resultant serum samples were analyzed using a validated ELISA assay for total mAb1 concentrations. The data were analyzed by means of noncompartmental methods. Pharmacokinetic (PK) parameter estimates such as observed maximal concentration in serum (Cmax), the time of observed maximal concentration (Tmax), area under the concentration vs. time curve (AUC), clearance (CL), volume of distribution (Vz), and mean residence time (MRT) were determined. The bioavailability following subcutaneous administration was approximately 78%.

At low doses, mAb1 had a half-life of 28 to 30 hr. At high doses, the terminal half-life estimate was approximately 225 hr when drug levels were above 10 µg/ml. The half-life was approximately 80 hr when serum concentrations were below 10 µg/ml.

Example 9

Toxicology Studies of Anti-IL-6R Antibody mAb1

In a GLP toxicology study, mAb1 was administered to cynomolgus monkeys via SC injection twice weekly for 13 consecutive weeks (total of 26 doses). Groups of 12 animals (6/sex) were administered 0 (placebo), 1, 5, 15 or 50 mg/kg/dose. Four animals/sex scheduled for the primary necropsy within 1 week of the end of dosing period and the remaining 2 animals/sex/group were assigned to a 12-week nondosing recovery period. The animals were observed for mortality and moribundity. Clinical examinations were performed daily and detailed physical examinations were performed weekly. Individual body weights were recorded weekly. Clinical pathology evaluations included hematology, serum chemistry, urine and CRP analysis. Blood samples were collected periodically for toxicokinetic and antibody evaluation. Ophthalmic and electrocardiogram examinations were performed periodically through out the study. Complete necropsies were performed on all animals. Selected organs were weighed and selected tissues were examined microscopically. All animals survived to the scheduled primary or recovery necropsies. There were no test article-related clinical findings or effects on appetite, body weights, ophthalmologic examination results, electrocardiographic parameters, macroscopic findings or organ weights.

Results indicated that administration of mAb1 via subcutaneous injection to cynomolgus monkeys twice weekly for 13 consecutive weeks was well tolerated. Slight decreases in neutrophil counts, fibrinogen, and CRP values in monkeys administered mAb1 were considered to be effects or possible effects of test article administration, but were not considered to be adverse and in general, alterations in neutrophil counts and fibrinogen values resolved during the recovery period. CRP values were quite variable and alterations and subsequent resolution when compared to controls were not consistent in all groups. Test article treatment resulted in minimal to moderate perivascular mixed inflammatory cell infiltrates in dermis and/or subcutis in subcutaneous injection sites. Full or partial reversibility was evident following the recovery period. Findings of unclear relationship to test article treatment included severe diffuse subacute inflammation in heart in a single female administered 5 mg/kg and minimal focal subacute inflammation accompanied by mild perivascular mononuclear cell infiltrates in the brain of a single male administered 1 mg/kg. Toxicokinetic data indicate substantial systemic mAb1 exposure during the dosing phase of the study. In addition, 10 of the 16 recovery animals had circulating levels of mAb1 throughout the entire recovery period, while 6 animals had no detectable mAb1 at the end of the study. The no-observed-adverse-effect level (NOAEL) for subcutaneous injection of mAb1 to cynomolgus monkeys twice weekly for 13 consecutive weeks was 50 mg/kg.

Example 10

Single Dose Study in Subjects with Rheumatoid Arthritis

In order to evaluate the potential of mAb1 for treatment of RA, a study was conducted to evaluate safety, tolerability and pharmacokinetics of SC administered mAb1. The primary objective was to assess the safety and tolerability of a single dose of subcutaneously administered mAb1 in subjects with rheumatoid arthritis who were concomitantly treated with methotrexate. The secondary objective was to assess the PK profile of a single subcutaneous dose of mAb1 and immunogenicity of a single SC dose of mAb1.

Endpoints. The primary efficacy endpoint was the percent change from Baseline in hs-C reactive protein ("hs-CRP"). Exploratory endpoints were the percent change in Subject's Assessment of Pain and Subject's Global Assessment of Disease activity.

Study Design. This is a multi-centered, randomized, double blind, placebo-controlled, single dose parallel group study of the safety, tolerability and pharmacodynamics of subcutaneously administered mAb1 in subjects with rheumatoid arthritis who were receiving concomitant methotrexate. Three (3) sequential cohorts of 5 subjects (4:1 active:placebo) were dosed SC with 50, 100, or 200 mg mAb1 or placebo. In each cohort, 1 week safety data from the first 2 subjects dosed was reviewed prior to dosing of the remaining subjects in the cohort. Screening took place within the window of 2 weeks to 3 days prior to the start of dosing (Day-14 to Day-3). On Study Day-1, the subjects underwent pre-dose study procedures and randomization. On Study Day-1, the subjects received SC blinded study drug or placebo. Subjects returned home following the 8 hour blood draw. Subjects returned to the clinic for outpatient visits on Study Days 3, 4, 8 (Week 1), 11, 15 (Week 2), 22 (Week 3), 29 (Week 4), 43 (Week 6), 57 (Week 8), 85 (Week 12) and 113 (Week 16), for safety assessments and blood sampling. Subjects completed an End of Study (EOS) visit on Study Day 113 (Week 16). Subjects who completed the study participated in 14 study visits.

Subject Eligibility. Inclusion Criteria: 1. Male or female $\geq$ 18 years of age; 2. Subjects must weigh >50 kg and <100 kg; 3. Diagnosis of Rheumatoid Arthritis (RA) as defined by the 1987 revised American College of Rheumatology (ACR) criteria with disease duration of no less than 6 months and ACR class I-III; 4. Subjects must receive a minimum of 8 weeks treatment with methotrexate (MTX) prior to the Screening visit. Subjects must be on a stable dose of MTX (7.5 to 25 mg/week) for a minimum of 4 weeks prior to the Screening Visit; 5. All subjects will take folic acid 1 mg daily or 5 mg weekly with the MTX dose, to minimize toxicity, according to local guidelines; 6. Oral prednisone 0 mg/day is allowed, as long as the dose is stable for 4 weeks prior to Screening and for the duration of the study; 7. For women of childbearing potential, a negative serum pregnancy test at the Screening Visit (Visit 1) and a negative urine pregnancy test at Day-1; 8. For men and women of childbearing potential, willingness to utilize adequate contraception and not become pregnant (or have their partner[s] become pregnant) during the full course of the study. Adequate contraceptive measures include oral contraceptives (stable use for 2 or more cycles prior to the Screening visit); IUD; DEPO-PROVERA®; NORPLANT® System implants; bilateral tubal ligation; vasectomy; condom or diaphragm plus either contraceptive sponge, foam or jelly.

Exclusion Criteria: 1. A history of Listeriosis or active tuberculosis (TB); 2. Persistent chronic or active recurring infection requiring treatment with antibiotics, antivirals, or antifungals within 4 weeks prior to the Screening Visit; 3. History of prior articular or prosthetic joint infection; 4. History of a hypersensitivity reaction, other than localized injection site reaction (ISR), to any biological molecule; 5. History of a hypersensitivity reaction to doxycycline, tetracycline or related compounds; 6. Significant concomitant illness such as, but not limited to cardiac, renal, neurological, endocrinological, metabolic or lymphatic disease that would adversely affect the subject's participation in this study; 7. Uncontrolled diabetes, defined as Hemoglobin A1c (HbA1c) $\geq$9.0% at the Screening Visit; 8. Presence of any of the following laboratory abnormalities at the Screening Visit: WBC <4,000/µl; platelet count <150,000/µl; neutrophils <2000/µl, AST/ALT > 1.5× ULN; 9. Serum creatinine $\geq$1.5×ULN at the Screening Visit; 10. Subjects with a positive intradermal skin tuberculin test (PPD 5TU) $\geq$5 mm induration read at 48 to 72 hours after placement; 11. Chest radiograph (at the Screening visit) consistent with prior tuberculosis infection including, but not limited to, apical scarring, apical fibrosis, or multiple calcified granulomata. This does not include non-caseating granulomata; 12. Use of parenteral or intra-articular glucocorticoids within 4 weeks prior to the Screening Visit; 13. Treatment with anakinra within two weeks prior to the Screening Visit; 14. Treatment with etanercept, cyclosporine, mycophenolate, tacrolimus, gold, penicillamine, sulfasalazine, or hydroxychloroquine within 4 weeks prior to the Screening Visit; 15. Treatment with adalimumab within 6 weeks prior to the Screening Visit; 16. Treatment with abatacept, azathioprine, cyclophosphamide or infliximab within 12 weeks prior to the Screening Visit; 17. Treatment with leflunomide or rituximab within 6 months prior to the Screening Visit; 18. Treatment with tocilizumab or any anti-IL-6 medications prior to Screening Visit; 19. Received administration of any live (attenuated) vaccine within 3 months prior to the Screening Visit; 20. Known history of Human Immunodeficiency Virus (HIV) antibody; and/or positive Hepatitis B surface antigen (HBsAg), and/or positive Hepatitis C antibody (HCV) at the Screening Visit; 21. History of malignancy other than carcinoma in-situ of the cervix, or adequately treated, non-metastatic squamous or basal cell carcinoma of the skin within five years prior to Screening Visit; 22. History of demyelinating disease or multiple sclerosis; 23. History of myeloproliferative disorder; 24. History of alcohol or drug abuse within the 5 years prior to the Screening Visit; 25. Any subject who has had surgery within 4 weeks prior to the Screening Visit; 26. Any subjects with planned elective surgery; 27. Any other arthritic or medical condition that in the opinion of the investigator could interfere with study evaluations; 28. Participation in any clinical research study evaluating another investigational drug or therapy within 30 days or at least 5 half-lives, whichever is longer, of the investigational drug, prior to the Screening Visit.

Study Drug Dosage and Administration. Subjects returned to the clinic for the Baseline visit on Day-1. Once eligibility was confirmed via pre dose procedures, the subject was randomly allocated to receive either mAb1 or placebo. Dose assignments were determined by the allocation schedule. Dosing took place starting at approximately 08:00 on Day 1. Subjects were required to be fasting (no food or water) beginning at midnight on Day-1. Study doses of 50, 100, and 200 mg were administered via subcutaneous injection. Each dose was administered in a single injection. All study drug injections were administered in the abdomen.

Dose Preparation. Study drug was supplied as lyophilized powder in sterile, single-use vials. Each vial contained 250 mg of mAb1 and provided a stock solution of 100 mg/ml after reconstitution. Placebo was supplied in matched vials. mAb1 was reconstituted in Sterile Water For Injection (WFI), and contained a withdrawable volume of up to 2.0 ml. Dosing volume was 0.5 ml for the 50 mg dose, 1.0 ml for the 100 mg dose, and 2.0 ml for the 200 mg dose.

Study Procedures and Visits. Physical Examination. A physical examination was conducted at the Screening visit, Day-1 (Visit 2), Day 15 (Visit 7), and Day 113 (Visit 14, EOS). Vital Signs Vital signs including temperature, sitting blood pressure, pulse and respiration were collected at every study visit. On Day 1 (Visit 3), vital signs were done prior to each pharmacokinetic blood draw at hour 0 (pre-dose) and at hour 8 post dose. Pharmacokinetic and Antibody Sample Collection Serum samples were collected for pharmacokinetic (PK) analysis at every study visit beginning on Day 1 (Visit 3). On Day 1 (Visit 3), samples were collected at hour 0 (pre-dose) and at hour 8±3 minutes (post-dose). PK samples were subsequently collected at the same time each day on Study Days 3, 4, 8, 11, 15, 22, 29, 43, 57, 85 and 113 (±2 hours). Serum samples were collected for analysis of antibodies to mAb1.

PPD Skin Test. Tuberculin purified protein derivative (PPD) 5TU skin test were placed intradermally at the time of the Screening visit and read 48 to 72 hours after inoculation. All subjects, with the exception of subjects who tested PPD positive and were successfully treated with anti-tuberculosis therapy, but including those with a prior history of *Bacillus Calmette Guerin* (BCG) administration received a PPD 5TU skin test. Subjects' successful treatment for a prior tuberculosis infection was documented in the source document, if applicable. Those subjects with a positive PPD 5TU skin test, ≧5 mm induration at 48 to 72 hours were excluded from the study.

Chest X-Ray. A radiologist's interpretation (signed and dated) of the standard posterior-anterior and lateral chest X-rays noted the absence of calcified granulomas and/or pleural scarring consistent with TB. This information was documented in the subject's medical chart and on the appropriate case report form at the Screening visit. A normal chest X-ray report was deemed acceptable if it had been done within the three months prior to the Screening visit.

Electrocardiogram. A standard 12-lead electrocardiogram (ECG) was performed at the Screening visit, Day 3 (Visit 4), Day 8 (Visit 6), Day 15 (Visit 8) and Day 29 (Visit 10). Heart rate was recorded from the ventricular rate and the PR, QRS, QT and QTc (QTc=QT/[60/heart rate]1/2) intervals were recorded.

Subject's Assessment of Pain. An 11-point scale (0=no pain to 10=severe pain) was used to measure the subject's current level of pain. The subject was instructed to circle a box on the continuum indicating the appropriate response.

Subject's Global Assessment of Disease Activity. An 11-point scale (0=no symptoms to 10=severe symptoms) was used to measure the subject's overall assessment of his/her current disease activity. The subject was instructed to circle a box on the continuum indicating the appropriate response.

Additional Sample Collection. Blood and urine were collected as indicated for routine laboratory measurements. Subjects fasted beginning at midnight on the Day-1 (Visit 2, Baseline) and Day 43 (Visit 10, EOS) study visits. Plasma and/or serum samples were collected as indicated and used for future analysis of serum proteins (i.e. proteomic analysis) as related to underlying disease in response to IL-6.

Schedule of Study Visits. Visit 1; Screening Visit (Day-14 to Day-3): Informed Consent, Inclusion/Exclusion Criteria, Medical History, Physical Examination, Height and Weight, Vital Signs, Chest x-ray, PPD Skin Test 5TU (read at 48 to 72 hours), Electrocardiogram, Serum βHCG pregnancy test (for women of childbearing potential), Hepatitis C Virus (HCV) Ab, Hepatitis B Surface Antigen (HBsAg), HgbA1c, Hematology panel, Chemistry panel, Urinalysis, High sensitivity C-Reactive Protein (hs-CRP) and Serum Amyloid A (SAA), Erythrocyte Sedimentation Rate (ESR), IL-6 and fibrinogen, Concomitant medications, Adverse Events. Visit 2; Day-1: Vital Signs, Weight, Urine pregnancy test (for women of childbearing potential), Hematology panel, Chemistry panel, Urinalysis, Concomitant medications, Adverse events, Randomization. Visit 3, Dosing, Day 1, Baseline: Vital signs, Urine pregnancy test (for women of childbearing potential), Hematology panel, Chemistry panel, Urinalysis, hs-CRP and SAA, ESR, IL-6 and fibrinogen, Rheumatoid Factor/ANA/anti-dsDNA, Serum immunoglobulins, Serum ferritin, Iron, Total Iron Binding Capacity (TIBC), RNA, Proteomics sample, Pharmacokinetic blood draw (0 hours pre-dose and 8 hours post dose), Anti-mAb1 antibody, Subject's Assessment of Pain, Subject's Global Assessment of Disease Activity, Concomitant medications, Adverse events. Visit 4, Day 3: Vital signs, Electrocardiogram, Hematology panel, Chemistry panel, Urinalysis, hs-CRP and SAA, ESR, IL-6 and fibrinogen, RNA, Proteomics sample, Pharmacokinetic blood draw, Anti-mAb1 antibody, Concomitant medications, Adverse events. Visit 5, Day 4: Vital signs, Hematology panel, Chemistry panel, Urinalysis, Pharmacokinetic blood draw, RNA, Proteomic sample, Concomitant medications, Adverse events. Visit 6, Day 8: Vital signs, Electrocardiogram, Urine pregnancy test, Hematology panel, Chemistry panel, Urinalysis, hs-CRP and SAA, ESR, IL-6 and fibrinogen, Pharmacokinetic blood draw, RNA, Proteomic sample, Subject's Assessment of Pain; Subject's Global Assessment of Disease Activity; Concomitant medications, Adverse events. Visit 7, Day 11: Vital signs, Hematology panel, Chemistry panel, Pharmacokinetic blood draw, Concomitant medications, Adverse events. Visit 8, Day 15±1 day: Physical examination, Vital signs, Electrocardiogram, Urine pregnancy test, Hematology panel, Chemistry panel, Urinalysis, hs-CRP and SAA, ESR, IL-6 and fibrinogen, Pharmacokinetic blood draw, RNA, Proteomics sample, Subject's Assessment of Pain, Subject's Global Assessment of Disease Activity, Concomitant medications, Adverse events. Visit 9, Day 22±1 day: Vital signs, Hematology panel, Chemistry panel, Urinalysis, hs-CRP and SAA, ESR, IL-6 and fibrinogen, Pharmacokinetic blood draw, Concomitant medications, Adverse events. Visit 10, Day 29±1 day: Vital signs, Electrocardiogram, Urine pregnancy test, Hematology panel, Chemistry panel, Urinalysis, hs-CRP and SAA, ESR, IL-6 and fibrinogen, Serum ferritin, Iron, TIBC, Pharmacokinetic blood draw, RNA, Proteomics sample, Anti-mAb1 antibody, Subject's Assessment of Pain, Subject's Global Assessment of Disease Activity, Concomitant medications, Adverse events. Visit 11, Day 43±1 day: Vital signs, Hematology panel, Chemistry panel, Subject's Assessment of Pain, Subject's Global Assessment of Disease Activity, Pharmacokinetic blood draw, Concomitant medications, Adverse events. Visit 12, Day 57±1 day: Vital signs, Urine pregnancy test, Hematology panel, Chemistry panel, Urinalysis, hs-CRP and SAA, ESR, IL-6 and fibrinogen, Rheumatoid Factor/ANA/anti-dsDNA, Serum immunoglobulins, Serum ferritin, Iron, TIBC, Pharmacokinetic blood draw, RNA, Proteomics sample, Anti-mAb1 antibody, Subject's Assessment of Pain, Subject's Global Assessment of Disease Activity, Concomitant medications, Adverse events.

Visit 13, Day 85±1 day: Vital signs, Hematology panel, Chemistry panel, hs-CRP and SAA, ESR, IL-6 and fibrinogen, Pharmacokinetic blood draw, Concomitant medications, Adverse events. Visit 14, End of Study, Day 113±3 day: Physical examination, Vital signs, Weight, Height, Urine pregnancy test, Electrocardiogram, Serum pregnancy test, Hematology panel, Chemistry panel, Urinalysis, hs-CRP and SAA, ESR, IL-6 and fibrinogen, Rheumatoid Factor/ANA/anti-dsDNA, Serum immunoglobulins, Serum ferritin, Iron, TIBC, Pharmacokinetic blood draw, RNA, Proteomics sample, Anti-mAb1 antibody, Subject's Assessment of Pain, Subject's Global Assessment of Disease Activity, Concomitant medications, Adverse events.

Results: Baseline levels of RA-associated biomarkers (hsCRP, SAA, ESR, IL-6, Hb, and hepcidin) measured prior to administration of mAb1 or placebo are shown in Table 6 (n=15).

TABLE 6

| | |
|---|---|
| hsCRP | 5.6 mg/L |
| SAA | 4252 ng/mL |
| ESR | 19 mm/hr |
| IL-6 | 4.1 pg/mL |
| Hb | 12.3 g/dL |
| Mean hepcidin | 82.5 ng/mL |
| Median hepcidin | 60.8 ng/mL |

Median hepcidin levels (in ng/mL) over the course of the study are shown in Table 7.

TABLE 7

| Study Day | mAb1 dose (mg) | | | |
|---|---|---|---|---|
| | 0 | 50 | 100 | 200 |
| D1 | 57.6 | 38.5 | 66.3 | 87.8 |
| D4 | 8.8 | 39.6 | 22.8 | 49.3 |
| D8 | 13.9 | 49.5 | 25.9 | 38.1 |
| D29 | 0 | 24.0 | 55.5 | 66.5 |

The hepcidin levels for individual study participants is set forth in Table 8.

TABLE 8

| | | Serum Hepcidin (ng/mL) | | | |
|---|---|---|---|---|---|
| Subject | Treatment | Day 1 | Day 4 | Day 8 | Day 29 |
| 1002 | 50 mg mAb1 | 30.39 | 38.57 | 43.99 | 0 |
| 1004 | 50 mg mAb1 | 229.22 | 40.55 | 140.58 | 200.43 |
| 1005 | 50 mg mAb1 | 0 | 0 | 0 | 8.99 |
| 1003 | 50 mg mAb1 | 46.69 | 67.83 | 55.09 | 39.00 |
| 1016 | 100 mg mAb1 | 8.01 | 0 | 25.35 | 0 |
| 1019 | 100 mg mAb1 | 71.82 | 45.55 | 6.35 | 39.70 |
| 1020 | 100 mg mAb1 | 60.80 | 0 | 17.50 | 147.81 |

TABLE 8-continued

| | | Serum Hepcidin (ng/mL) | | | |
|---|---|---|---|---|---|
| Subject | Treatment | Day 1 | Day 4 | Day 8 | Day 29 |
| 1017 | 100 mg mAb1 | 88.88 | 49.77 | 156.34 | 71.36 |
| 1033 | 200 mg mAb1 | 0 | 9.00 | 0 | 0 |
| 1034 | 200 mg mAb1 | 37.10 | 54.81 | 6.48 | 27.14 |
| 1031 | 200 mg mAb1 | 138.56 | 43.80 | 69.65 | 105.91 |
| 1032 | 200 mg mAb1 | 226.18 | 101.92 | 150.01 | 157.49 |
| 1001 | placebo | 0 | 0 | 0 | 0 |
| 1018 | placebo | 115.12 | 229.96 | 169.06 | 96.82 |
| 1035 | placebo | 184.70 | 17.64 | 27.69 | 0 |

Safety was assessed by measuring neutrophils and alanine aminotransferase (ALT), as shown in Tables 9 and 10, respectively (ULN=upper limit of normal).

TABLE 9

| | Treatment Group | | | | |
|---|---|---|---|---|---|
| Neutrophil Range | MTX (n = 3) | 50 mg mAb1 + MTX (n = 4) | 100 mg mAb1 + MTX (n = 4) | 200 mg mAb1 + MTX (n = 4) | Combined mAb1 + MTX (n = 12) |
| <1.5 × 10³/µL | 0 | 1 (25%) | 0 | 2 (50%) | 3 (25%) |
| <1.0 × 10³/µL | 0 | 0 | 0 | 0 | 0 |
| <0.5 × 10³/µL | 0 | 0 | 0 | 0 | 0 |

TABLE 10

| | Treatment Group | | | | |
|---|---|---|---|---|---|
| ALT Range | MTX (n = 3) | 50 mg mAb1 + MTX (n = 4) | 100 mg mAb1 + MTX (n = 4) | 200 mg mAb1 + MTX (n = 4) | Combined mAb1 + MTX (n = 12) |
| >1 × ULN | 0 | 0 | 1 (25%) | 3 (75%) | 4 (33.3%) |
| >2 × ULN | 0 | 0 | 0 | 2 (50%) | 2 (16.7%) |
| >3 × ULN | 0 | 0 | 0 | 0 | 0 |
| >5 × ULN | 0 | 0 | 0 | 0 | 0 |
| >8 × ULN | 0 | 0 | 0 | 0 | 0 |

Example 11

Study in RA Subjects Receiving Concomitant Methotrexate

A second study was conducted to assess the safety and tolerability of multiple doses of subcutaneously administered mAb1 in subjects with rheumatoid arthritis who were receiving concomitant treatment with methotrexate. The study was conducted in three parts and included a total of 6 dose cohorts. Parts B and C began after the safety of Part A was assessed.

Part A: Dose cohort 1: 10 subjects were randomized (4:1) to receive either: 50 mg mAb1 SC every week (8 subjects) or placebo every week (2 subjects). Dose cohort 2: 10 subjects were randomized (4:1) to receive either: 100 mg mAb1 SC alternating with placebo every week (8 subjects), or placebo every week (2 subjects). Upon confirmation of the safety of Part A, enrollment in Part B was opened: Part B: Dose cohort 3: 10 subjects were randomized (4:1) to receive either: 100 mg mAb1 SC every week (8 subjects) or placebo every week (2 subjects). Dose cohort 4: 10 subjects were randomized (4:1) to receive either: 200 mg mAb1 SC alternating with placebo every week (8 subjects), or placebo every week (2 subjects). Dose cohort 5: 10 subjects were randomized (4:1)

to receive either: 150 mg mAb1 SC every week (8 subjects) or placebo every week (2 subjects). Part C: Dose cohort 6: 10 subjects were randomized (4:1) to receive either: 150 mg mAb1 SC every other week (8 subjects) or placebo every other week (2 subjects).

All subjects completed 5 weeks of treatment (dosing on Day 1, Weeks 1, 2, 3 and 4), followed by 5 weeks of safety follow-up, for a total duration of 10 weeks. Subjects completed 12 study visits (Screening, Day 1 (first dose, Baseline Visit), Day 8 (Week 1), Day 15 (Week 2), Day 22 (Week 3), Day 29 (Week 4), Day 36 (Week 5), Day 43 (Week 6), Day 50 (Week 7), Day 57 (Week 8), Day 64 (Week 9) and Day 71 (Week 10).

Inclusion Criteria: 1. Male or female ≧18 years of age; 2. Subjects weigh >50 kg and <100 kg; 3. Diagnosis of Rheumatoid Arthritis (RA) as defined by the 1987 revised American College of Rheumatology (ACR) criteria with disease duration of no less than 6 months and ACR class I-III; 4. Subjects must have received a minimum of 12 weeks treatment with methotrexate (MTX) prior to the Screening visit. Subjects must be on a stable dose of MTX (7.5 to 25 mg/week) for a minimum of 6 weeks prior to the Screening Visit; 5. All subjects took folic acid 1 mg daily or 5 mg weekly with the MTX dose, to minimize toxicity, according to local guidelines; 6. For men and women of childbearing potential, willingness to utilize adequate contraception and not become pregnant (or have their partner[s] become pregnant) during the full course of the study. Adequate contraceptive measures include oral contraceptives (stable use for 2 or more cycles prior to the Screening visit); IUD; DEPO-PROVERA®; NORPLANT® System implants; bilateral tubal ligation; vasectomy; condom or diaphragm plus either contraceptive sponge, foam or jelly.

Exclusion Criteria: 1. A history of Listeriosis or active tuberculosis (TB); 2. Persistent chronic or active recurring infection requiring treatment with antibiotics, antivirals, or antifungals within 4 weeks prior to the Screening Visit, or any active infection at the time of screening or randomization; 3. History of prior articular or prosthetic joint infection; 4. History of a hypersensitivity reaction, other than localized injection site reaction (ISR), to any biological molecule; 5. History of a hypersensitivity reaction to doxycycline, tetracycline or related compounds; 6. Significant concomitant illness such as, but not limited to cardiac, renal, neurological, endocrinological, metabolic or lymphatic disease that would adversely affect the subject's participation in this study; 7. Uncontrolled diabetes, defined as Hemoglobin A1c (HbA1c) ≧9.0% at the Screening Visit; 8. Presence of any of the following laboratory abnormalities at the Screening Visit: WBC <4,000/·L; platelet count <150,000 ·L; neutrophils <2000/·L, AST/ALT >1.5× ULN; 9. Serum creatinine ≧1.5×ULN at the Screening Visit; 10. Subjects with a positive intradermal skin tuberculin test (PPD 5TU) mm induration read at 48 to 72 hours after placement; 11. Chest radiograph (at the Screening visit) consistent with prior tuberculosis infection including, but not limited to, apical scarring, apical fibrosis, or multiple calcified granulomata. This does not include non-caseating granulomata; 12. Use of oral prednisone or equivalent >10 mg per day within 4 weeks prior to the Screening Visit; 13. Use of parenteral or intra-articular glucocorticoids within 4 weeks prior to the Screening Visit; 14. Treatment with anakinra within two weeks prior to the Screening Visit; 15. Treatment with etanercept, cyclosporine, mycophenolate, tacrolimus, gold, penicillamine, sulfasalazine, or hydroxychloroquine within 4 weeks prior to the Screening Visit; 16. Treatment with adalimumab within 6 weeks prior to the Screening Visit; 17. Treatment with abatacept, azathioprine, cyclophosphamide or infliximab within 12 weeks prior to the Screening Visit; 18. Treatment with leflunomide or rituximab within 6 months prior to the Screening Visit; 19. Use of tocilizumab or any other anti-IL-6 medication prior to the Screening Visit; 20. Prior exposure to mAb1; 21. Received administration of any live (attenuated) vaccine within 3 months prior to the Screening Visit; 22. Known history of Human Immunodeficiency Virus (HIV) antibody; and/or positive Hepatitis B surface antigen (HBsAg), and/or positive Hepatitis C antibody (HCV) at the Screening Visit; 23. History of malignancy other than adequately treated carcinoma in-situ of the cervix, or adequately treated, non-metastatic squamous or basal cell carcinoma of the skin within five years prior to Screening Visit; 24. History of demyelinating disease or multiple sclerosis; 25. History of myeloproliferative disorder; 26. History of alcohol or drug abuse within the 5 years prior to the Screening Visit; 27. Any subject who has had surgery within 4 weeks prior to the Screening Visit; 28. Any subjects with planned elective surgery; 29. Any other arthritic or medical condition that in the opinion of the investigator could interfere with study evaluations; 30. Participation in any clinical research study evaluating another investigational drug or therapy within 30 days or at least 5 half-lives, whichever is longer, of the investigational drug, prior to the Screening Visit.

Study drug was supplied as a lyophilized powder in sterile, single-use vials. Each vial contained 269 mg of mAb1 and provided a stock solution of 100 mg/mL after reconstitution. Placebo was supplied in matched vials. mAb1 was reconstituted in Sterile Water for Injection (WFI), and contained a withdrawable volume of up to 2 mL.

Study Drug Dosage. Subjects had a Screening Visit on Day-14 to Day-3. Once eligibility was confirmed, the subjects were randomly allocated to receive either mAb1 or placebo. Dose assignment into each group was determined by an IVRS. In Part A, subjects were randomized into two dose cohorts. Subjects in dose cohort 1 received either 50 mg mAb1 SC every week or matching placebo every week and subjects in cohort 2 received either 100 mg mAb1 SC alternating with placebo every week or matching placebo every week. Subjects in dose cohort 2 received a dose of 100 mg SC mAb1 on Day 1 (Visit 2), Day 15 (Visit 4) and Day 29 (Visit 6) and a dose of placebo on Day 8 (Visit 3) and Day 22 (Visit 5). Escalation to Part B took place after all 20 subjects in Part A completed the Day 36 (Week 5) visit and the laboratory and safety data were reviewed, and the safety of the 200 mg single dose was confirmed. Subjects in Part B were randomized into three dose cohorts. Subjects in dose cohort 3 received either 100 mg mAb1 SC every week or matching placebo every week; subjects in cohort 4 received either 200 mg mAb1 SC alternating with placebo every week or matching placebo every week and subjects in dose cohort 5 received either 150 mg mAb1 SC every week or matching placebo every week. Subjects in dose cohort 4 received a dose of 200 mg SC mAb1 on Day 1 (Visit 2), Day 15 (Visit 4) and Day 29 (Visit 6) and a dose of placebo on Day 8 (Visit 3) and Day 22 (Visit 5).

Schedule of Study Visits. Screening; Visit 1; Day-14 to Day-3: Informed Consent; Inclusion/Exclusion Criteria; Medical History; Physical Examination; Height and Weight; Vital Signs; Chest x-ray (PA and Lateral); PPD skin test 5 TU (to be read at 48 to 72 hours); hs-CRP; Complement (C3, C4 and CH50); SAA, fibrinogen, IL-6; ESR; Electrocardiogram; Serum βHCG pregnancy test (for women of childbearing potential); HCV Ab and HBsAg; HbA1c; Hematology panel; Chemistry panel; Urinalysis; Concomitant medications; Adverse Events. Visit 2; Baseline Visit; Day 1: Vital Signs, Weight; Urine pregnancy test (for women of childbearing potential); Hematology panel; Chemistry panel; Urinalysis;

hs-CRP; Complement (C3, C4 and CH50); SAA, fibrinogen, IL-6; ESR; Serum immunoglobulins; Rheumatoid Factor/ANA/anti-dsDNA; RNA; Proteomic sample; Plasma for MTX analysis; Pharmacokinetic blood draw; Anti-mAb1 antibody; Subject's Assessment of Pain; Subject's Global Assessment of Disease Activity; Concomitant medications; Adverse events; Randomization; Study drug administration. Visit 3; Day 8 (Week 1) (±1 day): Vital signs; Hematology panel; Chemistry panel; Urinalysis; hs-CRP; Complement (C3, C4 and CH50); SAA, fibrinogen, IL-6; ESR; RNA; Proteomic sample; Plasma for MTX analysis; Pharmacokinetic blood draw; Concomitant medications; Adverse events; Study drug administration. Visit 4; Day 15 (Week 2) (±1 day): Vital signs; Hematology panel; Chemistry panel; Urinalysis; hs-CRP; Complement (C3, C4 and CH50); SAA, fibrinogen, IL-6; ESR; Plasma for MTX analysis; Pharmacokinetic blood draw; Concomitant medications; Adverse events; Study drug administration. Visit 5: Day 22 (Week 3) (±1 day): Vital signs; Hematology panel; Chemistry panel; Urinalysis; hs-CRP; Complement (C3, C4 and CH50); SAA, fibrinogen, IL-6; ESR; Plasma for MTX analysis; Pharmacokinetic blood draw; Concomitant medications; Adverse events; Study drug administration. Visit 6: Day 29 (Week 4) (±1 day): Vital signs; Hematology panel; Chemistry panel; Urinalysis; hs-CRP; Complement (C3, C4 and CH50); SAA, fibrinogen, IL-6; ESR; Plasma for MTX analysis; Pharmacokinetic blood draw; Concomitant medications; Adverse events; Study drug administration. Visit 7: Day 36 (Week 5) (±1 day): Vital signs; Electrocardiogram; Urine pregnancy test (for women of childbearing potential); Hematology panel; Chemistry panel; Urinalysis; hs-CRP; Complement (C3, C4 and CH50); SAA, fibrinogen, IL-6; ESR; Plasma for MTX analysis; Pharmacokinetic blood draw; Anti-mAb1 antibody; Proteomic sample; RNA; Subject's Assessment of Pain; Subject's Global Assessment of Disease Activity; Concomitant medications; Adverse events. Visit 8; Day 43 (Week 6) (±1 day): Vital signs; Hematology panel; Chemistry panel; Urinalysis; hs-CRP; Complement (C3, C4 and CH50); Plasma for MTX analysis; Pharmacokinetic blood draw; Concomitant medications; Adverse events. Visit 9; Day 50 (Week 7) (±1 day): Vital signs, Hematology panel; Chemistry panel; Urinalysis; hs-CRP; Complement (C3, C4 and CH50); Plasma for MTX analysis; Pharmacokinetic blood draw; Concomitant medications; Adverse events. Visit 10: Day 57 (Week 8) (±1 day): Vital signs; Hematology panel; Chemistry panel; Urinalysis; hs-CRP; Complement (C3, C4 and CH50); SAA, fibrinogen, IL-6; ESR; RNA; Proteomic sample; Plasma for MTX analysis; Pharmacokinetic blood draw; Concomitant medications; Adverse events. Visit 11: Day 64 (Week 9) (±1 day): Vital signs; Hematology panel; Chemistry panel; Urinalysis; hs-CRP; Complement (C3, C4 and CH50); Plasma for MTX analysis; Pharmacokinetic blood draw; Concomitant medications; Adverse events. Visit 12: Day 71 (Week 10) (±1 day); End of Study: Physical Examination; Vital Signs; Weight; Height; Electrocardiogram; Serum pregnancy test (for women of childbearing potential); Hematology panel; Chemistry panel; Urinalysis; hs-CRP; Complement (C3, C4 and CH50); SAA, fibrinogen, IL-6; ESR; Serum immunoglobulins; Rheumatoid Factor/ANA/anti-dsDNA; RNA; Proteomic sample; Plasma for MTX analysis; Pharmacokinetic blood draw; Anti-mAb1 antibody; Subject's Assessment of Pain; Subject's Global Assessment of Disease Activity; Concomitant medications; Adverse events.

Results: Baseline levels of RA-associated biomarkers (hsCRP, SAA, ESR, IL-6, Hb, and hepcidin) measured prior to administration of mAb1 or placebo are shown in Table 11 (n=47).

TABLE 11

| | |
|---|---|
| hsCRP | 4.6 |
| SAA | 5800 |
| ESR | 25 |
| IL-6 | 4.5 |
| Hemoglobin | 13.3 |
| Mean hepcidin | 102.6 |
| Median hepcidin | 76.9 |

Safety was assessed by measuring neutrophils and alanine aminotransferase (ALT), as shown in Tables 12 and 13, respectively (qw=weekly dosing; q2w=biweekly dosing of mAb1 alternating with placebo).

TABLE 12

| | Treatment Group I | | | |
|---|---|---|---|---|
| Neutrophil Range | MTX (n = 13) | 50 mg mAb1 qw + MTX (n = 8) | 100 mg mAb1 q2w + MTX (n = 8) | 100 mg mAb1 qw + MTX (n = 8) |
| <1.5 × 10³/μL | 1 (8%) | 0 | 0 | 2 (25%) |
| <1.0 × 10³/μL | 0 | 0 | 0 | 1 (13%) |
| <0.5 × 10³/μL | 0 | 0 | 0 | 0 |

| | Treatment Group II | | | |
|---|---|---|---|---|
| Neutrophil Range | 200 mg mAb1 q2w + MTX (n = 7) | 150 mg mAb1 qw + MTX (n = 8) | 150 mg mAb1 q2w + MTX (n = 8) | Combined mAb1 + MTX (n = 47) |
| <1.5 × 10³/μL | 3 (43%) | 3 (38%) | 0 | 8 (17%) |
| <1.0 × 10³/μL | 1 (14%) | 1 (13%) | 0 | 3 (6%) |
| <0.5 × 10³/μL | 0 | 0 | 0 | 0 |

TABLE 13

| | Treatment Group I | | | |
|---|---|---|---|---|
| ALT Range | MTX (n = 13) | 50 mg mAb1 qw + MTX (n = 8) | 100 mg mAb1 q2w + MTX (n = 8) | 100 mg mAb1 qw + MTX (n = 8) |
| >1 × ULN | 3 (23%) | 2 (25%) | 4 (50%) | 6 (75%) |
| >1.5 × ULN | 0 | 1 (13%) | 1 (13%) | 4 (50%) |
| >2 × ULN | 0 | 0 | 0 | 2 (25%) |
| >3 × ULN | 0 | 0 | 0 | 0 |

| | Treatment Group II | | | |
|---|---|---|---|---|
| ALT Range | 200 mg mAb1 q2w + MTX (n = 7) | 150 mg mAb1 qw + MTX (n = 8) | 150 mg mAb1 q2w + MTX (n = 8) | Combined mAb1 + MTX (n = 47) |
| >1 × ULN | 4 (57%) | 4 (50%) | 1 (13%) | 21 (45%) |
| >1.5 × ULN | 2 (29%) | 2 (25%) | 0 | 10 (21%) |
| >2 × ULN | 1 (14%) | 1 (13%) | 0 | 4 (9%) |
| >3 × ULN | 0 | 0 | 0 | 0 |

Example 12

Subcutaneously Administered mAb1 in Subjects with Rheumatoid Arthritis

A third study was conducted to assess the bioeffect of a single dose of mAb1 compared with placebo in subjects with active rheumatoid arthritis who were receiving concomitant treatment with methotrexate.

Study Design. The study was designed as a single-dose, double-blind, placebo-controlled, parallel group safety, tolerability and pharmacodynamic study of subcutaneously (SC) administered mAb1 in rheumatoid arthritis patients who are receiving concomitant methotrexate. Four (4) parallel groups of 8 subjects each with active rheumatoid arthritis were dosed SC with 50, 100 or 200 mg mAb1 or placebo (1:1:1:1). Each subject received a single dose of mAb1 or placebo, and was followed for 6 weeks. Subjects (32) completed 10 study visits: (Screening, Day 1, Day 4, Day 8, Day 12, Day 15, Day 22, Day 29, Day 36 and Day 43).

Inclusion Criteria: 1. Male or female ≧18 years of age; 2. Subjects must weigh >50 kg and <100 kg; 3. Diagnosis of Rheumatoid Arthritis (RA) as defined by the 1987 revised American College of Rheumatology (ACR) criteria with disease duration of no less than 6 months and ACR class I-III; 4. Subjects must receive a minimum of 12 weeks treatment with methotrexate (MTX) prior to the Screening visit. Subjects must be on a stable dose of MTX (7.5 to 25 mg/week) for a minimum of 8 weeks prior to the Screening Visit; 5. All subjects will take folic acid at 5 mg weekly or greater with the MTX dose, to minimize toxicity; 6. hs-CRP 0 mg/L; 7. For men and women of childbearing potential, willingness to utilize adequate contraception and not become pregnant (or have their partner[s] become pregnant) during the full course of the study. Adequate contraceptive measures include oral contraceptives (stable use for 2 or more cycles prior to screening) and other prescription pharmaceutical contraceptives; IUD; bilateral tubal ligation; vasectomy; condom or diaphragm plus either contraceptive sponge, foam or jelly.

Exclusion Criteria: 1. A history of Listeriosis or active tuberculosis (TB); 2. Persistent chronic or active recurring infection requiring treatment with antibiotics, antivirals, or antifungals within 4 weeks prior to the Screening Visit; 3. History of prior articular or prosthetic joint infection; 4. History of a hypersensitivity reaction, other than localized injection site reaction (ISR), to any biological molecule; 5. History of a hypersensitivity reaction to doxycycline, tetracycline or related compounds; 6. Significant concomitant illness such as, but not limited to cardiac, renal, neurological, endocrinological, metabolic or lymphatic disease that would adversely affect the subject's participation in this study; 7. Uncontrolled diabetes, defined as Hemoglobin A1c (HbA1c) ≧9.0% at the Screening Visit; 8. Presence of any of the following laboratory abnormalities at the Screening Visit: WBC <4,000/μ; platelet <150,000/μl; neutrophils <2000/μl, AST/ALT >1.5× ULN; 9. Serum creatinine ≧1.5×ULN at the Screening Visit; 10. Subjects with a positive intradermal skin tuberculin test mm induration read at 48 to 72 hours after placement; 11. Chest radiograph (at the Screening visit) consistent with prior tuberculosis infection including, but not limited to, apical scarring, apical fibrosis, or multiple calcified granulomata. This does not include non-caseating granulomata; 12. Treatment with oral prednisone or equivalent >10 mg per day within 4 weeks prior to the Screening Visit; 13. Use of parenteral or intra-articular glucocorticoids within 4 weeks prior to the Screening Visit; 14. Treatment with anakinra within two weeks prior to the Screening Visit; 15. Treatment with etanercept, cyclosporine, mycophenolate, tacrolimus, gold, penicillamine, sulfasalazine, or hydroxychloroquine within 4 weeks prior to the Screening Visit; 16. Treatment with adalimumab within 6 weeks prior to the Screening Visit; 17. Treatment with abatacept, azathioprine, cyclophosphamide or infliximab within 12 weeks prior to the Screening Visit; 18. Treatment with leflunomide or rituximab within 6 months prior to the Screening Visit; 19. Treatment with tocilizumab or any other anti-IL-6 medication prior to Screening Visit; 20. Start treatment or change dose of current treatment with NSAIDs/COX2 inhibitors for 2 weeks prior to Screening; 21. Received administration of any live (attenuated) vaccine within 3 months prior to the Screening Visit; 22. Known history of Human Immunodeficiency Virus (HIV) antibody; and/or positive Hepatitis B surface antigen (HBsAg), and/or positive Hepatitis C antibody (HCV) at the Screening Visit; 23. History of malignancy other than carcinoma in-situ of the cervix, or adequately treated, non-metastatic squamous or basal cell carcinoma of the skin within five years prior the Screening Visit; 24. History of alcohol or drug abuse within the 5 years prior to the Screening Visit; 25. Any subject who has had surgery within 4 weeks prior to the Screening Visit; 26. Any subjects with planned elective surgery; 27. Participation in any clinical research study evaluating another investigational drug or therapy within 30 days or at least 5 half-lives, whichever is longer, of the investigational drug, prior to the Screening Visit; 28. Previous exposure to mAb1.

Study Drug Dosage. Subjects had a Screening Visit on Day-14 to Day-3. Once eligibility was confirmed, the subjects were randomly allocated to receive either mAb1 or placebo. Subjects were enrolled in 4 parallel groups of 8 subjects each and were dosed with 50, 100 or 200 mg SC mAb1 or placebo (1:1:1:1). Each subject received a single SC dose of mAb1 or placebo on Day 1, and was followed for 6 weeks.

Dose Preparation. Study drug was supplied as lyophilized powder in sterile, single-use vials. Each vial contained 269 mg of mAb1 and provided a stock solution of 100 mg/ml after reconstitution. The maximum dose to be administered per vial was 200 mg. Placebo was supplied in matched vials. mAb1 was reconstituted in Sterile Water For Injection (WFI), and contained a withdrawable volume of up to 2 ml. The 50 mg dose was administered at 0.5 ml, 100 mg at 1 ml, 200 mg at 2 ml and the placebo at 2 ml. All study drug injections were administered in the abdomen.

Screening; Visit 1; Day-14 to Day-3 (±2 days): Informed Consent; Inclusion/Exclusion Criteria; Medical History; Physical Examination; Height and Weight; Vital Signs; Chest x-ray (PA and Lateral); Tuberculin Skin Test (read at 48 to 72 hours); hs-CRP and SAA; ESR; Electrocardiogram; Serum βHCG pregnancy test (for women of childbearing potential); HCV Ab and HBsAg; Hematology panel; Chemistry panel; Urinalysis; Concomitant medications; Adverse Events. Visit 2; Baseline Visit; Day 1: Vital Signs; Weight; Urine pregnancy test (for women of childbearing potential); Hematology panel; Chemistry panel; Urinalysis; hs-CRP and SAA; ESR; IL-6; Serum immunoglobulins; Rheumatoid Factor/ANA/anti-dsDNA; RNA; Proteomic sample; Pharmacokinetic blood draw; Anti-mAb1 antibody; Subject's Assessment of Pain; Subject's Global Assessment of Disease Activity; Concomitant medications; Adverse events; Randomization; Study drug administration. Visit 3; Day 4: Vital signs; Hematology panel; Chemistry panel; Urinalysis; hs-CRP and SAA; ESR; IL-6; RNA; Proteomic sample; Pharmacokinetic blood draw; Anti-mAb1 antibody; Concomitant medications; Adverse events. Visit 4; Day 8: Vital signs; Hematology panel; Chemistry panel; Urinalysis; hs-CRP and SAA; ESR; IL-6; RNA; Proteomic sample; Pharmacokinetic blood draw; Concomitant medications; Adverse events. Visit 5: Day 12: Vital signs; Hematology panel; Chemistry panel; Urinalysis; hs-CRP and SAA; ESR; IL-6; RNA; Proteomic sample; Pharmacokinetic blood draw; Concomitant medications; Adverse events. Visit 6; Day 15: Vital Signs; Urine pregnancy test (for women of childbearing potential); Hematology panel; Chemistry panel; Urinalysis; hs-CRP and SAA; ESR; IL-6; Pharmacokinetic blood draw; Concomitant medications; Adverse events. Visit 7: Day 22: Vital signs; Hematology panel; Chemistry panel; Urinalysis; hs-CRP and SAA; ESR; IL-6; RNA; Proteomic sample; Pharmacokinetic blood draw; Concomitant medications; Adverse events. Visit 8; Day 29: Vital Signs; Urine pregnancy test (for women of childbearing potential); Hematology panel; Chemistry panel; Urinalysis; Electrocardiogram; hs-CRP and SAA; ESR; IL-6; Serum immunoglobulins; Rheumatoid Factor/ANA/anti-dsDNA; RNA; Anti-mAb1 antibody; Proteomic sample; Pharmacokinetic blood draw; Subject's Assessment of Pain; Subject's Global Assessment of Disease Activity; Concomitant medications; Adverse events. Visit 9; Day 36: Vital signs; Hematology panel; Chemistry panel; Urinalysis; hs-CRP and SAA; ESR; IL-6; RNA; Proteomic sample; Pharmacokinetic blood draw; Concomitant medications; Adverse events. Visit 10; Day 43; End of Study: Physical examination; Vital signs; Height and weight; Electrocardiogram; Serum βHCG pregnancy test (for women of childbearing potential); Hematology panel; Chemistry panel; Urinalysis; hs-CRP and SAA; ESR; IL-6; Serum immunoglobulins; Rheumatoid Factor/ANA/anti-dsDNA; RNA; Proteomic sample; Pharmacokinetic blood draw; Anti-mAb1 antibody; Subject's Assessment of Pain; Subject's Global Assessment of Disease Activity; Concomitant medications; Adverse events.

Results: Baseline levels of RA-associated biomarkers (hsCRP, SAA, ESR, IL-6, Hb, and hepcidin) measured prior to administration of mAb1 or placebo are shown in Table 14 (n=24).

TABLE 14

| | |
|---|---|
| hsCRP | 21.2 |
| SAA | 45713 |
| ESR | 48 |
| IL-6 | 28.8 |
| Hemoglobin | 12.3 |
| Mean hepcidin | 86.5 |
| Median hepcidin | 70.2 |

The median percent hepcidin change at day 8 is summarized in Table 15.

TABLE 15

| | mAb1 dose (mg) | | | |
|---|---|---|---|---|
| Study Day | 0 | 50 | 100 | 200 |
| D8 | −2.4 | 0.0 | −21.0 | −66.2 |

The hepcidin levels for individual study participants at Day 1 and Day 8 are set forth in Table 16. UD: Undetected.

TABLE 16

| Subject No. | mAb1 Treatment | Serum Hepcidin (ng/mL) | |
|---|---|---|---|
| | | Day 1 | Day 8 |
| 1-0008 | 50 mg | 166.2 | 136.3 |
| 3-0003 | 50 mg | 22.7 | 35.3 |
| 4-0003 | 50 mg | 71.9 | 27.6 |
| 5-0004 | 50 mg | UD | UD |
| 5-0006 | 50 mg | 25.0 | 27.4 |
| 6-0001 | 50 mg | 109.2 | 6.8 |
| 9-0005 | 50 mg | 60.8 | — |
| 11-001 | 50 mg | 35.4 | 37.8 |
| 1-0006 | 100 mg | 298.9 | 203.6 |
| 2-0002 | 100 mg | 97.4 | 113.7 |
| 2-0003 | 100 mg | 70.1 | 9.0 |
| 2-0007 | 100 mg | 189.1 | 12.4 |
| 3-0002 | 100 mg | UD | UD |
| 8-0007 | 100 mg | 38.3 | 34.4 |
| 11-002 | 100 mg | 60.3 | 20.3 |
| 11-008 | 100 mg | 15.2 | 18.5 |
| 2-0001 | 200 mg | 92.8 | 11.6 |
| 5-0005 | 200 mg | 47.3 | 20.3 |
| 5-0007 | 200 mg | 12.2 | 5.2 |
| 6-0006 | 200 mg | 12.9 | UD |
| 6-0007 | 200 mg | UD | UD |
| 10-001 | 200 mg | 171.8 | 94.2 |
| 11-005 | 200 mg | 148.9 | 37.7 |
| 11-007 | 200 mg | 145.1 | UD |
| 1-0004 | Placebo | 254.7 | 242.6 |
| 2-0006 | Placebo | 215.8 | 73.5 |
| 5-0003 | Placebo | 49.0 | 66.0 |
| 6-0002 | Placebo | 75.0 | 52.1 |
| 6-0003 | Placebo | UD | UD |
| 8-0006 | Placebo | 76.8 | 57.1 |
| 9-0002 | Placebo | 133.2 | 267.6 |
| 9-0009 | Placebo | 47.5 | 72.1 |

The percent change in high-sensitivity C-reactive protein (hsCRP) and circulating IL-6 levels are summarized in Tables 17 and 18, respectively.

TABLE 17

| | Placebo | 50 mg mAb1 | 100 mg mAb1 | 200 mg mAb1 | Combined |
|---|---|---|---|---|---|
| | Baseline value | | | | |
| N | 8 | 8 | 8 | 8 | 24 |
| Mean (SD) | 29.58(24.55) | 21.97(16.82) | 23.43(17.53) | 34.07(27.46) | 26.49(20.96) |
| Median | 21.150 | 16.250 | 24.400 | 29.800 | 24.200 |
| Min:Max | 5.43:78.70 | 5.29:48.20 | 1.22:44.40 | 8.12:96.10 | 1.22:96.10 |
| | % Change from Baseline at Day 4 | | | | |
| N | 6 | 6 | 4 | 4 | 14 |
| Mean (SD) | −16.58(23.84) | −7.98(71.17) | −39.39(18.82) | −66.54(15.29) | −33.68(52.26) |
| Median | −16.27 | −21.42 | −38.19 | −65.24 | −46.50 |
| Min:Max | −55.4:11.6 | −75.1:124.6 | −63.3:−17.9 | −84.5:−51.2 | −84.5:124.6 |
| P-value compared with placebo | — | 0.8182 | 0.1714 | 0.0190 | 0.1093 |

TABLE 17-continued

|  | Placebo | 50 mg mAb1 | 100 mg mAb1 | 200 mg mAb1 | Combined |
|---|---|---|---|---|---|
| | | | % Change from Baseline at Day 8 | | |
| N | 8 | 8 | 8 | 8 | 24 |
| Mean (SD) | 9.09(52.09) | −16.42(40.23) | −69.18(28.62) | −89.21(6.60) | −58.27(41.70) |
| Median | −2.99 | −17.27 | −72.42 | −91.66 | −75.97 |
| Min:Max | −57.2:95.5 | −77.7:36.5 | −96.6:−8.7 | −94.4:−74.3 | −96.6:36.5 |
| P-value compared with placebo | — | 0.4418 | 0.0011 | 0.0002 | 0.0017 |

TABLE 18

|  | Placebo | 50 mg mAb1 | 100 mg mAb1 | 200 mg mAb1 | Combined |
|---|---|---|---|---|---|
| | | | Baseline value | | |
| N | 8 | 8 | 8 | 8 | 24 |
| Mean (SD) | 33.94 (31.25) | 40.39 (26.55) | 25.59 (18.58) | 59.53 (68.35) | 41.83 (44.08) |
| Median | 21.875 | 47.160 | 26.090 | 24.520 | 33.400 |
| Min:Max | 6.22:90.63 | 5.30:78.42 | 2.81:45.11 | 3.69:190.02 | 2.81:190.02 |
| | | | % Change from Baseline at Day 4 | | |
| N | 6 | 7 | 4 | 4 | 15 |
| Mean (SD) | 1.39 (17.49) | 514.04 (603.32) | 318.17 (191.69) | 521.69 (471.82) | 463.85 (468.89) |
| Median | 3.50 | 244.85 | 259.08 | 351.40 | 268.79 |
| Min:Max | −25.9:21.2 | −45.8:1537.5 | 158.2:596.3 | 173.2:1210.7 | −45.8:1537.5 |
| P-value compared with placebo | — | 0.0513 | 0.0095 | 0.0095 | 0.0016 |
| | | | % Change from Baseline at Day 8 | | |
| N | 8 | 8 | 8 | 8 | 24 |
| Mean (SD) | −8.55 (27.60) | −13.21 (59.00) | 748.40 (685.54) | 966.87 (984.69) | 567.69 (789.60) |
| Median | −1.53 | −9.10 | 596.91 | 647.02 | 292.18 |
| Min:Max | −55.3:24.6 | −95.4:94.0 | 31.7:1857.0 | −71.4:2836.8 | −95.4:2836.8 |
| P-value compared with placebo | — | 0.7209 | 0.0002 | 0.0104 | 0.0228 |

Median percent changes from baseline for hs-CRP (Table 19), IL-6 (Table 20), hemoglobin (Table 21), serum amyloid A (Table 22), and erythrocyte sedimentation rate (Table 23) are shown below.

TABLE 19

|  | Placebo | 50 mg | 100 mg | 200 mg |
|---|---|---|---|---|
| Day 1 | — | — | — | — |
| Day 4 | −16.3 | −21.4 | −38.2 | −65.2 |
| Day 8 | −3.0 | −17.3 | −72.4 | −91.7 |
| Day 12 | −7.7 | −9.6 | −6.8 | −89.0 |
| Day 15 | 16.0 | −4.7 | −19.8 | −82.4 |
| Day 22 | −3.7 | 39.0 | −10.8 | −32.7 |
| Day 29 | 1.4 | −5.2 | −38.8 | −45.7 |
| Day 36 | 17.0 | −12.3 | −28.9 | −49.2 |
| Day 43 | −19.4 | −28.8 | 14.4 | −13.7 |

TABLE 20

|  | Placebo | 50 mg | 100 mg | 200 mg |
|---|---|---|---|---|
| Day 1 | — | — | — | — |
| Day 4 | 3.5 | 244.9 | 259.1 | 351.4 |
| Day 8 | −1.5 | −9.1 | 596.1 | 647.0 |
| Day 12 | −43.7 | −17.6 | 69.1 | 455.6 |
| Day 15 | 8.7 | −17.6 | 12.9 | 36.6 |
| Day 22 | −22.6 | 10.6 | −13.8 | −12.33 |
| Day 29 | 16.8 | −26.0 | 10.3 | −28.3 |
| Day 36 | −3.7 | −18.1 | −8.5 | −5.9 |
| Day 43 | −19.3 | −11.6 | −8.5 | −24.0 |

TABLE 21

|  | Placebo | 50 mg | 100 mg | 200 mg |
|---|---|---|---|---|
| Day −7 | 125.5 | 121 | 128 | 127.5 |
| Day 1 | 121.5 | 125 | 123.5 | 121 |
| Day 4 | 124 | 112 | 127 | 127 |
| Day 8 | 124 | 116 | 126 | 125.5 |
| Day 12 | 123 | 120 | 121.5 | 122.5 |
| Day 15 | 123.5 | 117.5 | 118 | 123.5 |
| Day 22 | 121 | 120 | 123 | 122 |
| Day 29 | 117 | 115.5 | 122 | 124.5 |
| Day 36 | 118 | 118 | 116.5 | 118 |
| Day 43 | 121 | 112.5 | 120 | 121 |

TABLE 22

|  | Placebo | 50 mg | 100 mg | 200 mg |
|---|---|---|---|---|
| Day 1 | — | — | — | — |
| Day 4 | −11.0 | −29.1 | −32.4 | −61.9 |
| Day 8 | 52.2 | −14.2 | −71.9 | −92.5 |
| Day 12 | 28.8 | −38.6 | 35.2 | −92.4 |
| Day 15 | 54.4 | −5.6 | 8.0 | −72.7 |
| Day 22 | 34.6 | −9.3 | 3.3 | −40.9 |
| Day 29 | 41.5 | −36.9 | 23.3 | −32.0 |
| Day 36 | 23.0 | −48.2 | −5.0 | −34.4 |
| Day 43 | 10.4 | −41.4 | 19.8 | −11.2 |

TABLE 23

|  | Placebo | 50 mg | 100 mg | 200 mg |
|---|---|---|---|---|
| Day 1 | — | — | — | — |
| Day 4 | −15 | −30 | −16.7 | −6.3 |
| Day 8 | −5.6 | −31.2 | −36.3 | −33.8 |
| Day 12 | 3.0 | −26.4 | −32.1 | −46.8 |
| Day 15 | 18.0 | −10.2 | −22.9 | −36.3 |
| Day 22 | 12.5 | −19.4 | −23.1 | −18.1 |
| Day 29 | 26.7 | −19.4 | −28.4 | −4.4 |
| Day 36 | 33.3 | −20.7 | −33.3 | −5.3 |
| Day 43 | 12.5 | −5.2 | −24.9 | −13.5 |

Safety was assessed by measuring neutrophils (Table 24) and alanine aminotransferase (ALT) (Table 25).

TABLE 24

| Neutrophil Range | Treatment Group | | | | |
|---|---|---|---|---|---|
| | MTX (n = 8) | 50 mg mAb1 + MTX (n = 8) | 100 mg mAb1 + MTX (n = 8) | 200 mg mAb1 + MTX (n = 8) | Combined mAb1 + MTX (n = 24) |
| <1.5 × 10³/μL | 0 | 1 (12.5%) | 3 (37.5%) | 2 (25%) | 6 (25%) |
| <1.0 × 10³/μL | 0 | 0 | 2 (25%) | 0 | 2 (8.3%) |
| <0.5 × 10³/μL | 0 | 0 | 0 | 0 | 0 |

TABLE 25

| ALT Range | Treatment Group | | | | |
|---|---|---|---|---|---|
| | MTX (n = 8) | 50 mg mAb1 + MTX (n = 8) | 100 mg mAb1 + MTX (n = 8) | 200 mg mAb1 + MTX (n = 8) | Combined mAb1 + MTX (n = 24) |
| >1 × ULN | 3 (37.5%) | 2 (25%) | 6 (75%) | 5 (62.5%) | 13 (54.2%) |
| >2 × ULN | 1 (12.5%) | 0 | 2 (25%) | 2 (25%) | 4 (16.7%) |
| >3 × ULN | 1 (12.5%) | 0 | 0 | 2 (25%) | 2 (8.3%) |
| >5 × ULN | 0 | 0 | 0 | 1 (12.5%) | 1 (4.17%) |
| >8 × ULN | 0 | 0 | 0 | 0 | 0 |

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

What is claimed is:

1. A method for treating rheumatoid arthritis in a patient, the method comprising:
   (a) administering to the patient a first dose of a human antibody or antigen-binding fragment thereof which specifically binds to human interleukin-6 receptor (hIL6-R), and
   (b) administering to the patient at least one subsequent dose of the human antibody or antigen-binding fragment;
   wherein the human antibody or antigen-binding fragment comprises the complementarity determining regions (CDRs) of a heavy chain variable region (HCVR) comprising the amino acid sequence of SEQ ID NO:19, and the CDRs of a light chain variable region (LCVR) comprising the amino acid sequence of SEQ ID NO:27.

2. The method of claim 1, wherein the first dose and the subsequent dose of the human antibody or antigen-binding fragment are each administered to the patient subcutaneously.

3. The method of claim 1, wherein the first dose and the subsequent dose are each about 50 mg to about 200 mg of the human antibody or antigen-binding fragment.

4. The method of claim 1, wherein the first dose and the subsequent dose are administered 1 week to 6 weeks apart.

5. The method of claim 3, wherein the first dose and the subsequent dose are each 50 mg, 100 mg, 150 mg or 200 mg and administered 1 week apart or 2 weeks apart.

6. The method of claim 5, further comprising administering to the patient one or more subsequent doses of the human antibody or antigen-binding fragment at 50 mg, 100 mg, 150 mg, or 200 mg, weekly or biweekly.

7. The method of claim 1, wherein the human antibody or antigen-binding fragment comprises a HCVR and a LCVR, wherein the HCVR comprises heavy chain CDRs (HCDR1, HCDR2 and HCDR3) comprising the amino acid sequences of SEQ ID NOS:21, 23 and 25, respectively, and the LCVR comprises light chain CDRs (LCDR1, LCDR2 and LCDR3) comprising the amino acid sequences of SEQ ID NOS:29, 31 and 33, respectively.

8. The method of claim 7, wherein the antibody or antigen-binding fragment comprises a HCVR comprising the amino acid sequence of SEQ ID NO:19.

9. The method of claim 7, wherein the antibody or antigen-binding fragment comprises a LCVR comprising the amino acid sequence of SEQ ID NO:27.

10. The method of claim 7, wherein the antibody or antigen-binding fragment comprises a HCVR comprising the amino acid sequence of SEQ ID NO:19 and a LCVR comprising the amino acid sequence of SEQ ID NO:27.

* * * * *